US011459557B2

(12) United States Patent
Platt et al.

(10) Patent No.: US 11,459,557 B2
(45) Date of Patent: Oct. 4, 2022

(54) USE AND PRODUCTION OF CHD8+/− TRANSGENIC ANIMALS WITH BEHAVIORAL PHENOTYPES CHARACTERISTIC OF AUTISM SPECTRUM DISORDER

(71) Applicants: The Broad Institute, Inc., Cambridge, MA (US); Massachusetts Institute of Technology, Cambridge, MA (US)

(72) Inventors: Randall Jeffrey Platt, Basel (CH); Feng Zhang, Cambridge, MA (US); Ian Slaymaker, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/467,949

(22) Filed: Mar. 23, 2017

(65) Prior Publication Data
US 2018/0044662 A1 Feb. 15, 2018

Related U.S. Application Data

(63) Continuation-in-part of application No. PCT/US2015/051691, filed on Sep. 23, 2015.

(60) Provisional application No. 62/181,002, filed on Jun. 17, 2015, provisional application No. 62/180,859, filed on Jun. 17, 2015, provisional application No. 62/054,675, filed on Sep. 24, 2014.

(51) Int. Cl.
| | |
|---|---|
| C12N 15/10 | (2006.01) |
| C12N 15/63 | (2006.01) |
| C12N 9/22 | (2006.01) |
| A01K 67/027 | (2006.01) |
| C12N 15/11 | (2006.01) |
| C12N 15/85 | (2006.01) |
| C12N 15/86 | (2006.01) |
| C12N 15/90 | (2006.01) |

(52) U.S. Cl.
CPC ...... *C12N 15/1024* (2013.01); *A01K 67/0275* (2013.01); *C12N 9/22* (2013.01); *C12N 15/1082* (2013.01); *C12N 15/111* (2013.01); *C12N 15/63* (2013.01); *C12N 15/8509* (2013.01); *C12N 15/86* (2013.01); *C12N 15/907* (2013.01); *A01K 2217/072* (2013.01); *A01K 2227/105* (2013.01); *A01K 2267/0306* (2013.01); *A01K 2267/0318* (2013.01); *C12N 2015/8536* (2013.01); *C12N 2310/10* (2013.01); *C12N 2310/20* (2017.05); *C12N 2310/3519* (2013.01); *C12N 2310/531* (2013.01); *C12N 2320/11* (2013.01); *C12N 2320/32* (2013.01); *C12N 2330/51* (2013.01); *C12N 2740/16043* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 4,186,183 | A | 1/1980 | Alving et al. |
| 4,217,344 | A | 8/1980 | Handjani et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,774,085 | A | 9/1988 | Fidler |
| 4,797,368 | A | 1/1989 | Carter et al. |
| 4,837,028 | A | 6/1989 | Allen |
| 4,873,316 | A | 10/1989 | Meade et al. |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |
| 5,846,946 | A | 12/1998 | Huebner et al. |
| 6,750,059 | B1 | 6/2004 | Blakesley et al. |
| 7,259,015 | B2 | 8/2007 | Kingsman et al. |
| 7,745,651 | B2 | 6/2010 | Heyes et al. |
| 7,776,321 | B2 | 8/2010 | Cascalho et al. |
| 7,799,565 | B2 | 9/2010 | Maclachlan et al. |
| 7,803,397 | B2 | 9/2010 | Heyes et al. |

(Continued)

FOREIGN PATENT DOCUMENTS

| | | |
|---|---|---|
| EP | 0264166 A1 | 4/1988 |
| EP | 1519714 A1 | 4/2005 |

(Continued)

OTHER PUBLICATIONS

State et al., "The Emerging Biology of Autism Spectrum Disorders" 337 Science 1301-1303 (2012).*

(Continued)

*Primary Examiner* — Nancy J Leith
(74) *Attorney, Agent, or Firm* — F. Brent Nix, Esq.; Johnson, Marcou, Isaacs & Nix, LLC

(57) ABSTRACT

Methods and compositions for inducing a plurality of mutations in transgenic Cas9 eukaryotes to model a neuronal disease or disorder. The invention further comprehends testing putative treatments with such models, e.g., testing putative chemical compounds that may be pharmaceutically relevant for treatment or gene therapy that may be relevant for treatment, or combinations thereof. The invention allows for the study of genetic diseases and putative treatments to better understand and alleviate a genetic disease or a condition, e.g., autism, autism-spectrum disease or disorder, obsessive-compulsive disorder, or psychiatric disorders.

19 Claims, 10 Drawing Sheets
Specification includes a Sequence Listing.

(56) References Cited

U.S. PATENT DOCUMENTS

| | | |
|---|---|---|
| 7,838,658 B2 | 11/2010 | Maclachlan et al. |
| 7,901,708 B2 | 3/2011 | Maclachlan et al. |
| 7,915,399 B2 | 3/2011 | Maclachlan et al. |
| 7,982,027 B2 | 7/2011 | Maclachlan et al. |
| 8,044,019 B2 | 10/2011 | Uno et al. |
| 8,058,069 B2 | 11/2011 | Yaworski et al. |
| 8,188,263 B2 | 5/2012 | Maclachlan et al. |
| 8,236,943 B2 | 8/2012 | Lee et al. |
| 8,283,333 B2 | 10/2012 | Yaworski et al. |
| 8,372,951 B2 | 2/2013 | Chang et al. |
| 8,404,658 B2 | 3/2013 | Hajjar et al. |
| 8,454,972 B2 | 6/2013 | Nabel et al. |
| 8,575,305 B2 | 11/2013 | Gait et al. |
| 8,614,194 B1 | 12/2013 | Chen et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2004/0013648 A1 | 1/2004 | Kingsman et al. |
| 2004/0171156 A1 | 9/2004 | Hartley et al. |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0111106 A1 | 4/2009 | Mitrophanous et al. |
| 2010/0317109 A1 | 12/2010 | Maden et al. |
| 2011/0059502 A1 | 3/2011 | Chalasani |
| 2011/0117189 A1 | 5/2011 | Mazzone et al. |
| 2011/0265198 A1 | 10/2011 | Gregory et al. |
| 2011/0293571 A1 | 12/2011 | Widdowson et al. |
| 2011/0293703 A1 | 12/2011 | Mahon et al. |
| 2012/0003201 A1 | 1/2012 | Nicholas et al. |
| 2012/0017290 A1 | 1/2012 | Cui et al. |
| 2012/0251618 A1 | 10/2012 | Schrum et al. |
| 2013/0236946 A1 | 9/2013 | Gouble |
| 2013/0244279 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2017/0349894 A1 | 6/2017 | Dahlman et al. |
| 2017/0349914 A1 | 12/2017 | Cox et al. |

FOREIGN PATENT DOCUMENTS

| | | |
|---|---|---|
| EP | 1664316 A1 | 6/2006 |
| EP | 1766035 A1 | 3/2007 |
| EP | 1781593 A2 | 5/2007 |
| EP | 2771468 A1 | 9/2014 |
| EP | 2784162 A1 | 10/2014 |
| EP | 2764103 B1 | 8/2015 |
| WO | 9116024 A1 | 10/1991 |
| WO | 9117424 A1 | 11/1991 |
| WO | 9324641 A2 | 12/1993 |
| WO | 9426877 A1 | 11/1994 |
| WO | 9639154 A1 | 12/1996 |
| WO | 9703211 A1 | 1/1997 |
| WO | 2011028929 A3 | 3/2011 |
| WO | 2013138585 A1 | 9/2013 |
| WO | 2014018423 A2 | 1/2014 |
| WO | 2014093595 | 6/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093694 A1 | 6/2014 |
| WO | 2014093701 A1 | 6/2014 |
| WO | 2014093709 A1 | 6/2014 |
| WO | 2014093712 A1 | 6/2014 |
| WO | 2014093718 A1 | 6/2014 |
| WO | 2014204723 A1 | 12/2014 |
| WO | 2014204724 A1 | 12/2014 |
| WO | 2014204725 A1 | 12/2014 |
| WO | 2014204726 A1 | 12/2014 |
| WO | 2014204727 A1 | 12/2014 |
| WO | 2014204728 A1 | 12/2014 |
| WO | 2014204729 A1 | 12/2014 |
| WO | 2015065964 A1 | 5/2015 |
| WO | 2016049024 A1 | 3/2016 |
| WO | 2016049163 A2 | 3/2016 |
| WO | 2016049258 A2 | 3/2016 |

OTHER PUBLICATIONS

Moretti et al., "MeCP2 dysfunction in Rett syndrome and related disorders" 16 Current Opinion in Genetics & Development 276-281 (2006).*

International Search Report dated Mar. 31, 2016, which issued during prosecution of International Application No. PCT/US2015/051691.

Cong, et al. "Multiplex Genome Engineering Using CRISPR/Cas Systems", Science, 2013, 819-823.

Jao, et al. "Efficient multiplex biallelic zebrafish genome editing using a CRISPR nuclease system", Proceedings of the National Academy of Sciences, 2013, including Supporting Information,110:13904-13909, www.pnas.org/cgi/doi/10.1073/pnas/1308335110.

Ran, et al. "Double Nicking by RNA-Guided CRISPR Cas9 for Enhanced Genome Editing Specificity", Cell, 2013, 154:1380-1389.

Shalem, et al. "Genome-Scale CRISPR-Cas9 Knockout Screening in Human Cells", Science, 2014, 343:84-87.

Yang, et al. "One-Step Generation of Mice Carrying Reporter and Confidintial Alleles by CRISPR/Cas-Mediated Genome Engineering", Cell, 2013, 154:1370-1379.

Ran, et al., "In Vivo Genome Editing using *Staphylococcus aureau* Cas9", Nature, vol. 520, No. 7546, Apr. 9, 2015, 186-191.

Ronemus, et al., "The Role of De Novo Mutations in the Genetics of Autism Spectrum Disorders", Nature Reviews Genetics, vol. 15, No. 2, Feb. 2014, 133-141.

Rothwell, et al., "Autism-Associated Neuroligin-3 Mutations Commonly Impair Striatal Circuits to Boost Repetitive Behaviors", Cell, vol. 158, No. 1, Jul. 3, 2014, 198-212.

Sanders, et al., "De Novo Mutations Revealed by Whole-Exome Sequencing are Strongly Associated with Autism", Nature, vol. 485, No. 7397, Apr. 4, 2012, 237-241.

Sanjana, et al., "Improved Vectors and Genome-Wide Libraries for CRISPR Screening", Nature Methods, vol. 11, No. 8, Aug. 2014, 783-784.

(56) References Cited

OTHER PUBLICATIONS

Schmeisser, et al., "Autistic-Like Behaviours and Hyperactivity In Mice Lacking Prosap1/Shank2", Nature. vol. 486, No. 7402, Jun. 2012, 256-260.
Shanks, et al., "Chromodomain Helicase Binding Protein 8 (Chd8) is a Novel A-Kinase Anchoring Protein Expressed During Rat Cardiac Development", PLoS One, vol. 7, No. 10, 2012, 14 pages.
Shen, et al., "Generation of gene-modified mice via Cas9/RNA-mediated gene targeting", Cell Research, vol. 23, No. 5, 2013, 720-723.
Swiech, et al., "In Vivo Interrogation of Gene Function in the Mammalian Brain using CRISPR-Cas9", Nature Biotechnology, vol. 33, No. 1, Oct. 19, 2014, 102-106.
Tabuchi, et al., "A Neuroligin-3 Mutation Implicated in Autism Increases Inhibitory Synaptic Transmission in Mice", Science, vol. 318, No. 5847, 2007, 71-76.
Talkowski, et al., "Sequencing Chromosomal Abnormalities Reveals Neurodevelopmental Loci that Confer Risk Across Diagnostic Boundaries", Cell, vol. 149, No. 3, 2012, 525-237.
Terriente-Felix, "A Conserved Function of the Chromatin Atpase Kismet in the Regulation of Hedgehog Expression", Developmental Biology, vol. 350, Issue 2, Feb. 15, 2011, 382-392.
Tian, et al., "Contribution Of Mglur5 To Pathophysiology in a Mouse Model of Human Chromosome 16p11.2 Microdeletion", Nature Neuroscience, 2015, 182-184.
Wang, et al., "Genetic Screens in Human Cells Using the CRISPR/Cas9 System", Science, vol. 343, No. 6166, Jan. 3, 2014, 80-84.
Wang, et al., "One-Step Generation of Mice Carrying Mutations in Multiple Genes by CRISPR/Cas-Mediated Genome Engineering", Cell, vol. 153, No. 4, May 9, 2013, 910-918.
Welch, et al., "Cortico-Striatal Synaptic Defects and OCD-like Behaviours in Sapap3-Mutant Mice", Nature, vol. 448, Aug. 23, 2007, 894-900.
Won, et al., "Autistic-Like Social Behaviour in Shank2-Mutant Mice Improved by Restoring NMDA Receptor Function", Nature, vol. 486, No. 7402, Jun. 13, 2012, 261-265.
Wu, et al., "Genome-Wide Binding of the CRISPR Endonuclease Cas9 in Mammalian Cells", Nature Biotechnology, vol. 32, No. 7, Jul. 2014, 670-676.
Xiao, et al., "Chromosomal deletions and inversions mediated by TALENs and CRIPPR/Cas in zebrafish", Nucleic Acids Research, vol. 14, No. 14, 2013, 42 pages.
Zahir, et al., "Novel Deletions of 14q11.2 Associated with Developmental Delay, Cognitive Impairment and Similar Minor Anomalies in Three Children", Journal of Medical Genetics, vol. 44, No. 9, Sep. 2007, 556-561.
Zetsche, et al., "A split-Cas9 architecture for inducible genome editing and transcription modulation", Nature biotechnology, vol. 33, No. 2, 2015, 139-142.
Cong et al., "Multiplex genome engineering using CRISPR/Cas systems," Science, vol. 339, No. 6121, pp. 819-823, 2013.
Ran et al., "Double Nicking by RNA-Guided CRISPR Cas9 for Enhanced Genome Editing Specificity," Cell, vol. 154, No. 6, pp. 1380-1389, 2013.
Courtine et al., "Can experiments in nonhuman primates expedite the translation of treatments for spinal cord injury in humans?" Nat Med., 13, pp. 561-566, 2007.
Shengdar et al., "Dimeric CRISPR RNA-guided FokI nucleases for highly specific genome editing," Nature Biotechnology, 32(6), pp. 569-576, 2014.
Harno et al., "Metabolic Pitfalls of CNS Cre-Based Technology," Cell Metabolism, vol. 18, issue 1, pp. 21-28, Jul. 2013.
Berkovic et al., "Human epilepsies: interaction of genetic and acquired factors," Trends in Neuroscience , 29(7), pp. 391-397, 2006.
Yang et al., "One-step generation of mice carrying reporter and conditional alleles by CRISPR/Cas-mediated genome engineering," Cell 154, 1370-1379, 2013.

Jansen, et al., "Identification of a Novel Family of Sequence Repeats among Prokaryote," OMICS A Journal of Integrative Biology, vol. 6, No. 1, pp. 23-33, 2002.
Mojica et al., "Biological significance of a family of regularly spaced repeats in the genomes of Archaea, Bacteria and mitochondria," Mol. Microbiol., 36(1), pp. 244-246, 2000.
Xue et al., "CRISPR-mediated direct mutation of cancer genes in the mouse liver," Nature, 514(7522), pp. 380-384, Oct. 2014.
Yin et al., "Genome editing with Cas9 in adult mice corrects a disease mutation and phenotype," Nat Biotechnol. Jun. 2014;32(6):551-553.
Heckl, et al., "Generation of mouse models of myeloid malignancy with combinatorial genetic lesions using CRISPR-Cas9 genome editing," Nature Biotechnology vol. 32, pp. 941-946, 2014.
Shalem et al., "Genome-Scale CRISPR-Cas9 Knockout Screening in Human Cells," Science, vol. 343, No. 6166, pp. 84-87, 2014.
Chesselet et al., "Animal Models of Neurological Disorders," Neurotherapeutics, 9, pp. 241-244, 2012.
Auvin et al., "Novel Animal Models of Pediatric Epilepsy," Neurotherapeutics, 9, pp. 245-261, 2012.
Fremont et al., "Alternative Approaches to Modeling Hereditary Dystonias," Neurotherapeutics, 9, pp. 315-322, 2012.
Ehrlich, "Huntington's Disease and the Striatal Medium Spiny Neuron: Cell-Autonomous and Non-Cell-Autonomous Mechanisms of Disease," Neurotherapeutics, 9, pp. 270-284, 2012.
Gould, "Mouse Models of Spinocerebellar Ataxia Type 3 (Machado-Joseph Disease)," Neurotherapeutics, 9, pp. 285-296, 2012.
Bubier et al., "Accelerating Discovery for Complex Neurological and Behavioral Disorders Through Systems Genetics and Integrative Genomics in the Laboratory Mouse," Neurotherapeutics, 9, pp. 338-348, 2012.
Back et al., "The Instrumented Fetal Sheep as a Model of Cerebral White Matter Injury in the Premature Infant," Neurotherapeutics, 9, pp. 359-370, 2012.
Cook et al., "Nonhuman Primate Models of Stroke for Translational Neuroprotection Research," Neurotherapeutics, 9, pp. 371-379, 2012.
Rosenzweig, et al., "Extensive spontaneous plasticity of corticospinal projections after primate spinal cord injury," Nature Neuroscience vol. 13, pp. 1505-1510 (2010).
Campeau et al., "RNA interference in mammals: behind the screen," Briefings in Functional Genomics. vol 10. No. 4, pp. 215-226, 2011.
Iossifov et al., "The contribution of de novo coding mutations to autism spectrum disorder," Nature vol. 515, pp. 216-221, Nov. 13, 2014.
Iossifov et al., "De Novo Gene Disruptions in Children on the Autistic Spectrum," Neuron, vol. 7, No. 2, pp. 285-299, Apr. 2012.
Abrahams, "Advances in Autism Genetics: On the Threshold of a New Neurobiology", Nature Reviews Genetics, vol. 9, No. 5, May 2008, 341-355.
The Broad Institute, Inc., "International Preliminary Report on Patentability issued in International Application No. PCT/US2015/051691", dated Mar. 28, 2017, 11 pages.
Baudouin, et al., "Shared Synaptic Pathophysiology in Syndromic and Nonsyndromic Rodent Models of Autism", Science, vol. 338, Oct. 5, 2012, 128-132.
Bernier, et al., "Disruptive CHD8 Mutations Define A Subtype of Autism Early in Development", Cell, vol. 158, No. 2, Jul. 17, 2014, 263-276.
Chadman, et al., "Minimal Aberrant Behavioral Phenotypes of Neuroligin-3 R451C Knockin Mice", Autism Research, vol. 1, No. 3, Jun. 2008, 147-158.
Chen, et al., "Genome-Wide CRISPR SPCT/US2014/62558creen in a Mouse Model of Tumor Growth and Metastasis", Cell, vol. 160, No. 6, Mar. 12, 2015, 1246-1260.
De Rubeis, et al., "Synaptic, Transcriptional and Chromatin Genes Disrupted in Autism", Nature, vol. 515, No. 7526, Nov. 2014, 209-215.
Deltcheva, et al., "CRISPR RNA Maturation by Trans-Encoded Small RNA and Host Factor Rnase III", Nature, vol. 471, No. 7340, Mar. 31, 2011, 602-607.

(56) References Cited

OTHER PUBLICATIONS

Ding, et al., "Semaphorin 3E-Plexin-D1 Signaling Controls Pathway-Specific Synapse Formation in the Striatum", Nature Neuroscience, vol. 15, No. 2, Dec. 2018, 215-223.

Doench, et al., "Rational Design of Highly Active Sgrnas for CRISPR-Cas9-Mediated Gene Inactivation", Nature Biotechnology, vol. 32, No. 12, Sep. 3, 2014, 1262-1267.

Etherton, et al., "Mouse Neurexin-1 alpha Deletion Causes Correlated Electrophysiological and Behavioral Changes Consistent with Cognitive Impairments", Proceedings of the National Academy of Sciences, vol. 106, No. 42, Oct. 20, 2009, 17998-18003.

Fromer, et al., "De Novo Mutations in Schizophrenia Implicate Synaptic Networks", Nature, vol. 506, No. 7487, Feb. 13, 2014, 179-184.

Gasiunas, et al., "Cas9-CrRna Ribonucleoprotein Complex Mediates Specific DNA Cleavage for Adaptive Immunity in Bacteria", Proceedings of the National Academy of Sciences, vol. 109, No. 39, Sep. 25, 2012, E2579-E2586.

Guy, et al., "A Mouse Mecp2-Null Mutation Causes Neurological Symptoms that Mimic Rett Syndrome", Nature Genetics, vol. 27, 2001, 322-326.

Guy, et al., "Reversal of Neurological Defects in a Mouse Model of Rett Syndrome", Science, vol. 315, No. 5815, Mar. 2007, 1143-1147.

Hsu, et al., "Development and Applications of CRISPR-Cas9 for Genome Engineering", Cell, vol. 157, No. 6,,] Jun. 5, 2014, 1262-1278.

Hsu, et al., "DNA Targeting Specificity of RNA-Guided Cas9 Nucleases", Nat. Biotechnol. vol. 31, No. 9, Sep. 3, 2013, 827-832.

Jamain, et al., "Reduced Social Interaction and Ultrasonic Communication in a Mouse Model of Monogenic Heritable Autism", Proceedings of the National Academy of Sciences, vol. 105, No. 5, Feb. 2008, 1710-1715.

Jiang, et al., "CRISPR-assisted Editing of Bacterial Genomes", Nature Biotechnology, vol. 31, Issue 3, Mar. 2013, 233-239.

Jinek, et al., "A Programmable Dual-RNA-Guided DNA Endonuclease in Adaptive Bacterial Immunity", Science, vol. 337, No. 6096,, Aug. 17, 2012, 816-821.

Karginov, et al., "The CRISPR System: Small RNA-Guided Defense in Bacteria and Archaea", Molecular Cell, vol. 37, Issue 1, Jan. 15, 2010, 23 pages.

Kibar, et al., "Mutations in VANGL1 Associated with Neural-Tube Defects", New England Journal of Medicine, vol. 356, No. 14, May 2007, 1432-1437.

Kim, et al., "Genetic and Expressional Alterations of CHD Genes in Gastric and Colorectal Cancers", Histopathology, vol. 58, No. 5, Mar. 2011, 660-668.

Konermann, et al., "Genome-Scale Transcriptional Activation by an Engineered CRISPR-Cas9 Complex", Nature, vol. 517, No. 7536, Dec. 10, 2014, 583-588.

Konermann, et al., "Optical Control of Mammalian Endogenous Transcription and Epigenetic States", Nature, vol. 500, No. 7463, Aug. 22, 2013, 472-476.

Krumm, et al., "Excess of Rare, Inherited Truncating Mutations in Autism", Nature Genetics, vol. 47, No. 6, Jun. 2015, 582-588.

Kwon, et al., "Pten Regulates Neuronal Arborization and Social Interaction in Mice", Neuron, vol. 50, No. 3, May 4, 2006, 377-388.

Lewandoski, et al., "Analysis of Fgf8 Gene Function in Vertebrate Development", Cold Spring Harb Symp Quant Biol., vol. 62, 1997, 159-168.

Long, et al., "Prevention of Muscular Dystrophy in Mice by CRISPR/Cas9-Mediated Editing of Germline DNA", Science, vol. 345, No. 6201, Sep. 5, 2014, 1184-1188.

Madisen, et al., "A Robust and High-Throughput Cre Reporting and Characterization System for the Whole Mouse Brain", Nature Neuroscience, vol. 13, No. 1, Jan. 2010, 133-140.

Mali, et al., "RNA-Guided Human Genome Engineering via Cas9", Science, vol. 339, No. 6121, Feb. 15, 2013, 823-826.

Michalon, et al., "Chronic Pharmacological Mglu5 Inhibition Corrects Fragile X in Adult Mice", Neuron, vol. 74, No. 1, Apr. 12, 2012, 49-56.

Nakatani, et al., "Abnormal Behavior in a Chromosome-Engineered Mouse Model for Human 15q11-13 Duplication Seen in Autism", Cell, vol. 137, No. 7, Jun. 26, 2009, 1235-1246.

Neale, et al., "Patterns and Rates of Exonic De Novo Mutations in Autism Spectrum Disorders", Nature, vol. 485, No. 7397, Apr. 2012, 242-245.

Nestler, et al., "Animal Models of Neuropsychiatric Disorders", Nature Neuroscience, vol. 13, No. 10, Oct. 2010, 1161-1169.

Nishimasu, et al., "Crystal Structure of Cas9 in Complex with Guide RNA and Target DNA", Cell, vol. 156, No. 5, Feb. 27, 2014, 935-949.

Nishiyama, et al., "CHD8 Suppresses P53-Mediated Apoptosis through Histone H1 Recruitment During Early Embryogenesis", Nature Cell Biology, vol. 11, No. 2, Feb. 2009, 172-182.

Nishiyama, et al., "Histone H1 Recruitment by CHD8 is Essential for Suppression of the Wnt-B-Catenin Signaling Pathway", Molecular and Cellular Biology, vol. 32, No. 2, Jan. 2012, 501-512.

O'Roak, et al., "Exome Sequencing in Sporadic Autism Spectrum Disorders Identifies Severe De Novo Mutations", Nature Genetics, vol. 43, No. 6, Jun. 2011, 585-589.

O'Roak, et al., "Multiplex Targeted Sequencing Identifies Recurrently Mutated Genes in Autism Spectrum Disorders", Science, vol. 338, No. 6114, Dec. 21, 2012, 1619-1622.

O'Roak, et al., "Sporadic Autism Exomes Reveal a Highly Interconnected Protein Network of De Novo Mutations", Nature, vol. 485, No. 7397, Apr. 4, 2012, 246-250.

Osterweil, et al., "Lovastatin Corrects Excess Protein Synthesis and Prevents Epileptogenesis in a Mouse Model Of Fragile X Syndrome", Neuron, vol. 77, No. 2, Jan. 23, 2013, 243-250.

Pan, et al., "Association of Genetic Variants of GRIN2B with Autism", Scientific Reports, vol. 5, No. 8296, 2015, 5 pages.

Parikshak, et al., "Integrative Functional Genomic Analyses Implicate Specific Molecular Pathways and Circuits in Autism", Cell, vol. 155, No. 5, Nov. 21, 2013, 1008-1021.

Peca, et al., "Shank3 Mutant Mice Display Autistic-Like Behaviours and Striatal Dysfunction", Nature, vol. 472, No. 7344, 2011, 437-442.

Penagarikano, "Absence of CNTNAP2 Leads to Epilepsy, Neuronal Migration Abnormalities and Core Autism-Related Deficits", Cell, vol. 147, No. 1, Sep. 30, 2011, 235-246.

Platt, et al., "CRISPR-Cas9 Knockin Mice for Genome Editing and Cancer Modelling", Cell, vol. 159, Issue 2, Oct. 9, 2014, 440-455.

Pouladi, et al., "Choosing an Animal Model for the Study of Huntington's Disease", Nature Reviews Neuroscience, vol. 14, 2013, 708-721.

Ran, et al., "Genome Engineering using the CRISPR-Cas9 System", Nature Protocols, vol. 8, No. 11, Nov. 2013, 2281-2308.

* cited by examiner

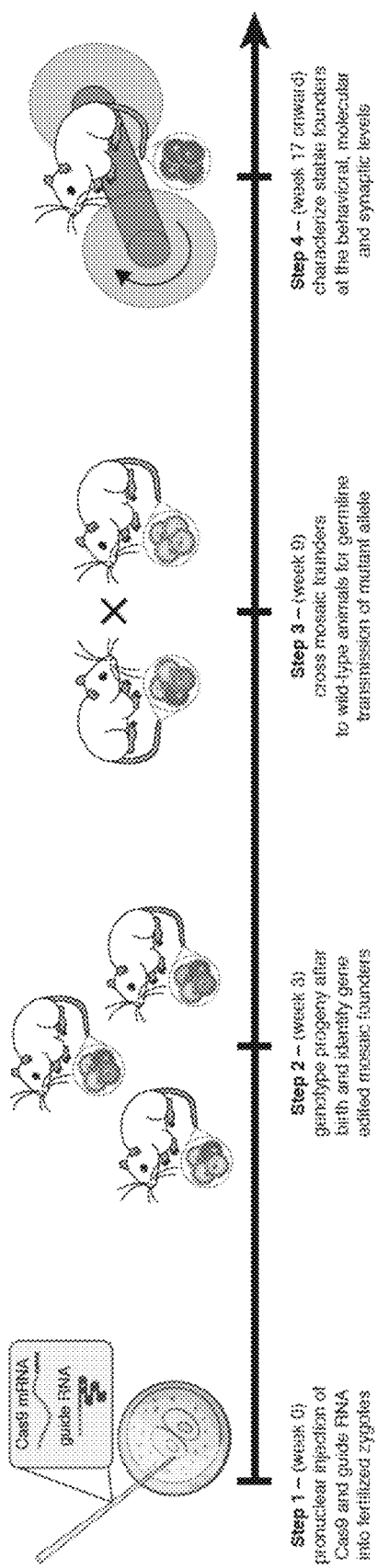
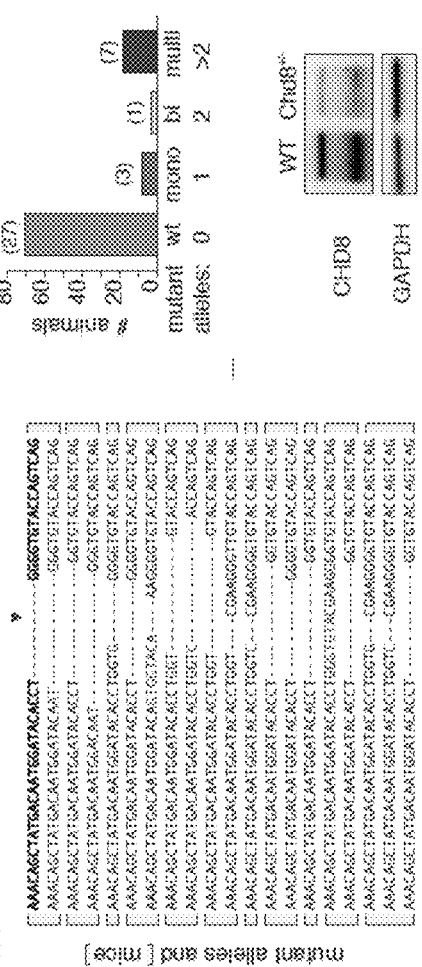
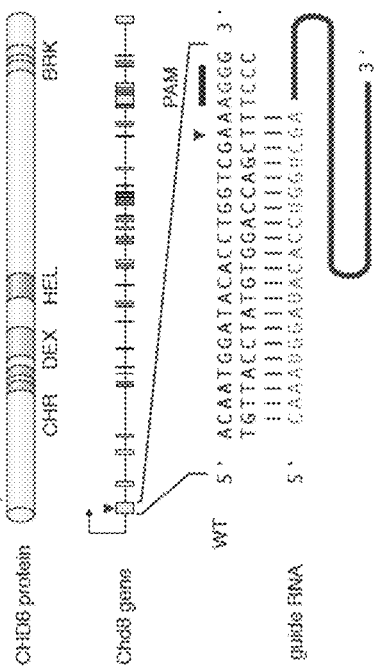

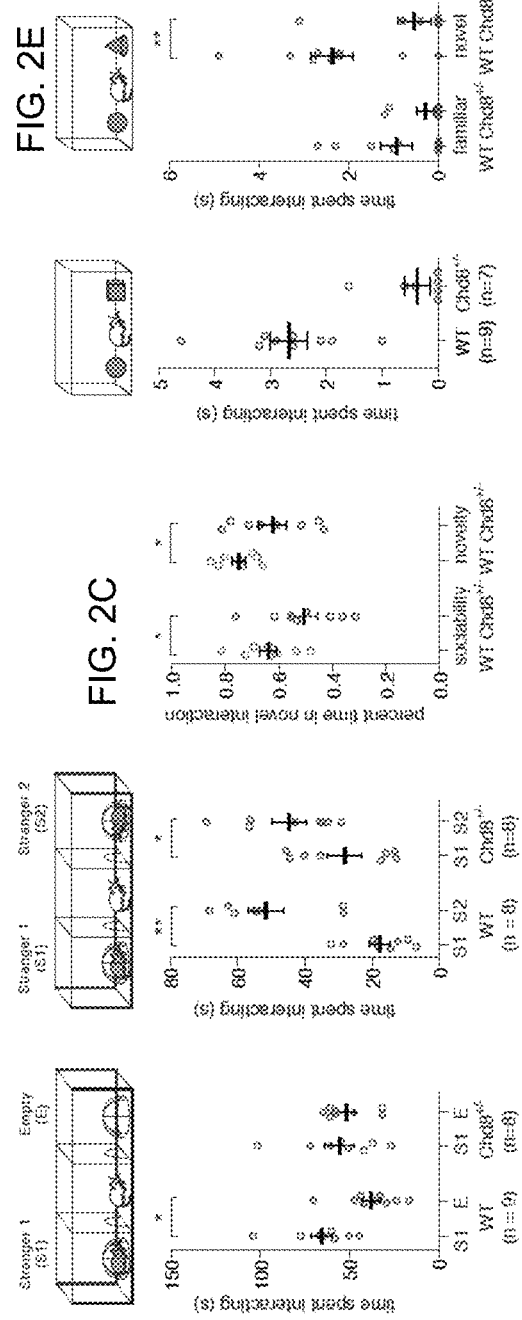
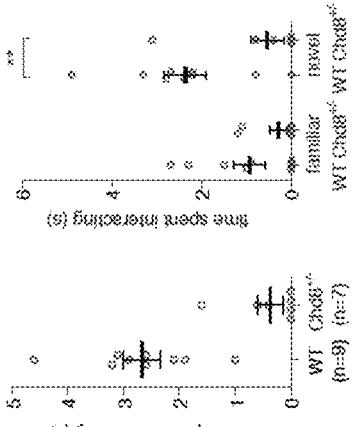
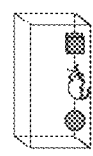
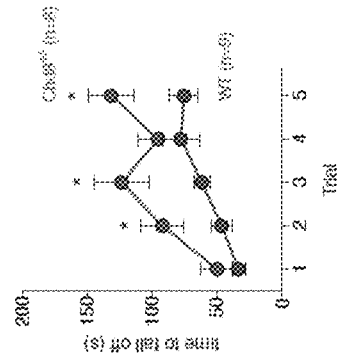
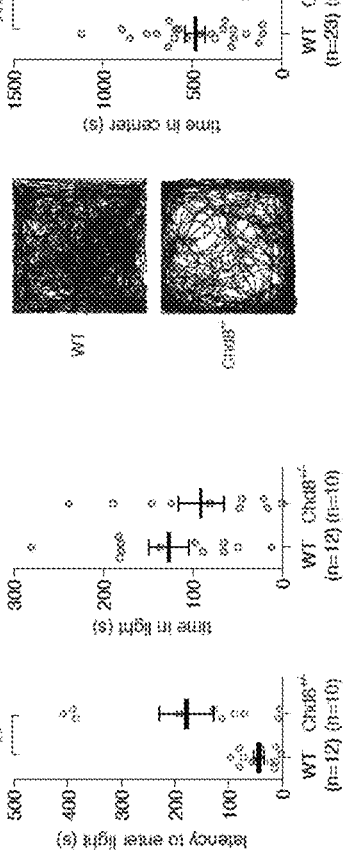
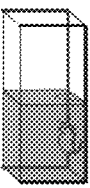

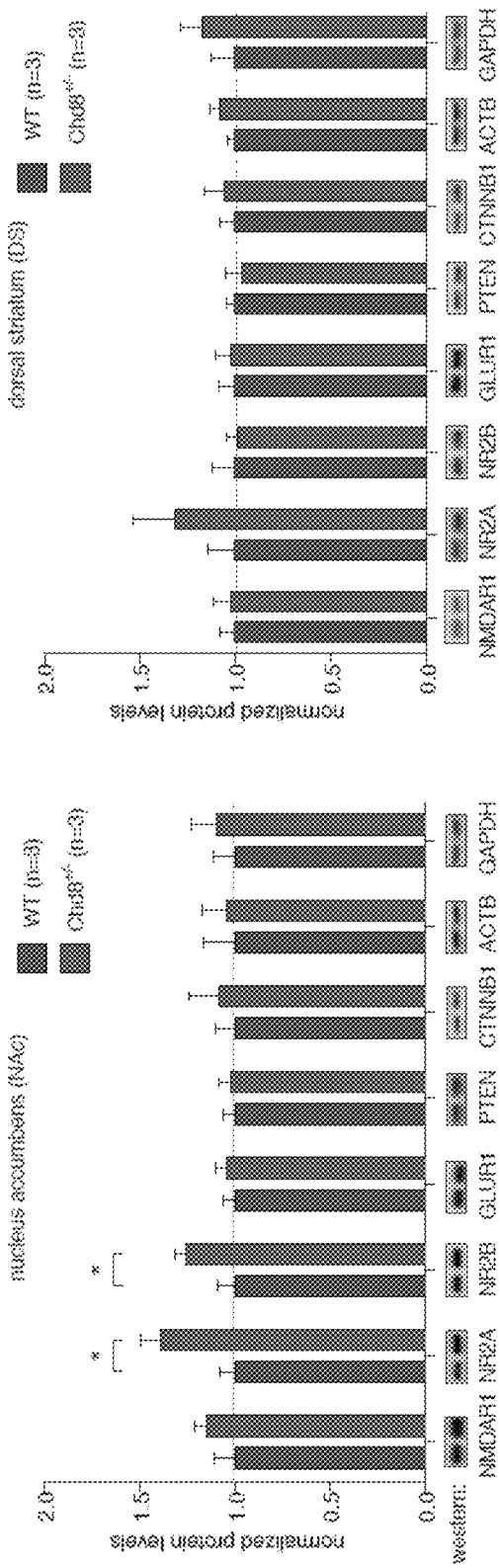
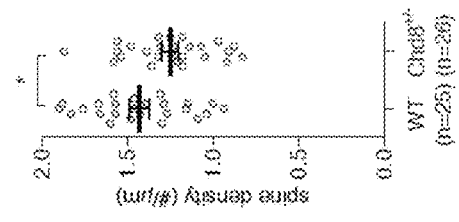
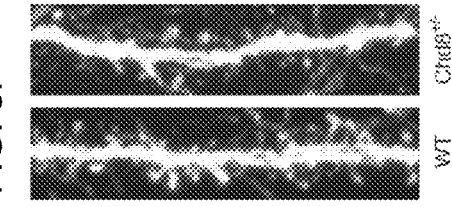
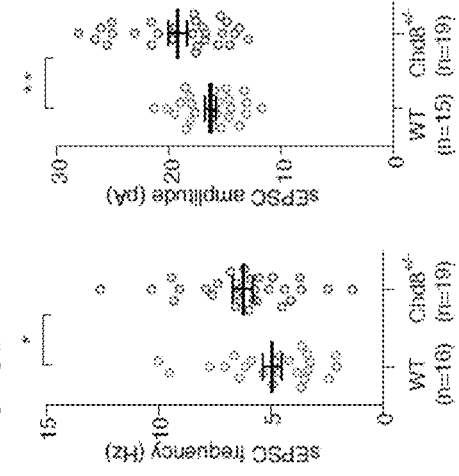
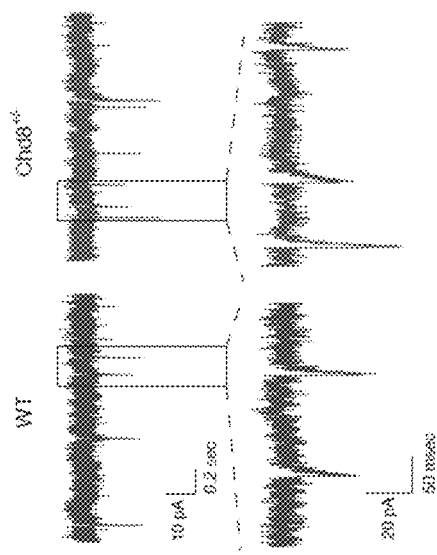

USE AND PRODUCTION OF CHD8+/− TRANSGENIC ANIMALS WITH BEHAVIORAL PHENOTYPES CHARACTERISTIC OF AUTISM SPECTRUM DISORDER

RELATED APPLICATIONS AND/OR INCORPORATION BY REFERENCE

This application is a Continuation-In-Part of International Application Number PCT/US2015/051691 filed on Sep. 23, 2015, which published as WO2016/049163 on Mar. 31, 2016 and claims benefit of and priority to U.S. provisional patent application Ser. No. 62/054,675, filed Sep. 24, 2014, and U.S. provisional patent application Ser. Nos. 62/181,002 and 62/180,859, both filed Jun. 17, 2015.

STATEMENT AS TO FEDERALLY SPONSORED RESEARCH

This invention was made with government support under Grant No. OD009552 awarded by the National Institutes of Health. The government has certain rights in the invention.

The foregoing application and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created Mar. 23, 2017 is named 47627992080 SL.txt and is 11,342 bytes in size.

FIELD OF THE INVENTION

The present invention generally relates to the Clustered Regularly Interspaced Short Palindromic Repeats (CRISPR)-Cas System and components thereof. More specifically, the present invention relates to the delivery, use and therapeutic applications of the CRISPR-Cas systems and compositions in a eukaryotic cell or organism and especially regarding their use in neuronal cells and tissues (including brain) ex vivo and/or in vivo using a transgenic CRISPR-Cas9 animal (e.g., mouse) model. The present invention also relates to mouse models that present phenotypes consistent with autism. The mouse models have loss-of-function mutations in the CHD8 gene. The present invention further relates to systems, methods, compositions, and kits for and uses thereof in research, diagnosis, drug discovery and therapy.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications.

CRISPR-Cas9 is a powerful technology for genome editing and is being widely adopted due to its efficiency and versatility. While Cas9-mediated genome editing applications are compelling, applying them in vivo and ex vivo is challenging, since commonly used delivery systems are inefficient and limit accessible cell types. Moreover, certain cell types, e.g., neuronal cells present challenges due to their particular sensitivity to perturbations, and are often not accessible for genetic manipulation due to delivery challenges.

A major challenge facing the continued study of genetics is distinguishing which mutations are drivers from those that are not ("passengers") (Garraway and Lander, 2013; Lawrence et al. 2013). The difficulty of elucidating these distinctions in animal models lies in precisely generating such mutation(s) and measuring the influence of specific mutations throughout the subject's condition. These challenges apply to other areas of genetic and tissue-specific biological studies as well.

Autism spectrum disorder (ASD) is a complex neurodevelopmental disorder characterized by impairments in social interaction, communication and behavioral flexibility ASD is defined by two hallmark diagnostic behavioral criteria: (i) persistent deficits in social interaction across multiple contexts and (ii) restrictive and repetitive patterns of behavior, interests, or activities (American Psychiatric Association. DSM-5 Task Force., 2013; Rosenberg et al., 2009).

Autism spectrum disorder (ASD) remains an ill-defined psychiatric disorder despite decades of research and significant advances towards uncovering its genetic and molecular underpinnings. This is due, in part, to a scarcity of tools and methodologies available to quickly test molecular hypotheses for causally linking genotype to phenotype. Although ASD has high heritability and concordance rates, significant genotypic and phenotypic diversity exists (Abrahams and Geschwind, 2008; American Psychiatric Association. DSM-5 Task Force., 2013; Geschwind, 2009; Rosenberg et al., 2009). Recent sequencing-based studies have identified more than 100 ASD risk alleles and implicate an additional 700 genes, highlighting the complexity of this condition (Abrahams and Geschwind, 2008; Iossifov et al., 2012; Krumm et al., 2015; O'Roak et al., 2011; O'Roak et al., 2012a; O'Roak et al., 2012b; Parikshak et al., 2013). The rate of sequencing has outstripped the pace at which the causality of the variants can be tested, highlighting the need for rapid generation of appropriate models to assess risk alleles identified in patients.

Despite the intricacy of ASD, mouse models have been created that carry single mutations in some of these genes and have been shown to exhibit ASD-relevant behaviors (Etherton et al., 2009; Jamain et al., 2008; Peca et al., 2011; Tabuchi et al., 2007). The establishment of such models, which show construct (i.e., the mouse mutation mirrors a mutation found in a patient) and face (i.e., the mutant mouse has similar phenotypes to those observed in a patient) validity (Nestler and Hyman, 2010), offer an entry point to studying the impact of risk alleles that have been identified through genome sequencing. Indeed, investigations into these mice have lead to mechanistic insight into the molecular, cellular, circuit, and behavioral basis of ASD.

Moreover, many of these genes share similar localization (synapse) and/or function (glutamatergic neurotransmission) but the others have broader functions, such as chromatin modification, DNA methylation and transcriptional regulation. While the understanding of how these latter genes mediate ASD neuropathology is limited, an emerging body of work suggests a convergent molecular circuitry among the many epigenetic and synaptic structure and function proteins. ASD has a strong genetic basis, although the genetics of autism are complex, it is unclear whether ASD is explained more by rare mutations with major effects or by rare multigene interactions of common genetic variants (Abrahams B S, Geschwind D H (2008). "Advances in autism genetics: on the threshold of a new neurobiology". *Nature Reviews Genetics* 9 (5): 341-55; and Buxbaum J D (2009). "Multiple rare variants in the etiology of autism spectrum disorders". *Dialogues Clin Neurosci* 11 (1): 35-43). Complexity arises due to interactions among multiple genes, the environment, and epigenetic factors which do not change DNA but are heritable and influence gene expression (Rapin I, Tuchman R F (2008). "Autism: definition, neurobiology, screening, diagnosis". *Pediatr Clin North Am* 55 (5): 1129-46). Thus, there is a need for models of Autism for understanding the disease and to develop novel therapies.

Citation or identification of any document in this application is not an admission that such document is available as prior art to the present invention.

SUMMARY OF THE INVENTION

It is an object of the present invention to provide vectors useful in generating an in vivo animal model for autism. It is another object of the present invention to provide a novel animal model that presents behavioral phenotypes reflective of ASD symptoms. It is another object of the present invention to provide methods of screening of drugs that alleviate ASD symptoms.

Chromodomain helicase DNA-binding protein 8 (CHD8) was identified as a leading autism spectrum disorder (ASD) candidate gene by whole-exome sequencing and subsequent targeted-sequencing studies (O'Roak B J, Vives L, Girirajan S, Karakoc E, Krumm N, Coe B P et al. Sporadic autism exomes reveal a highly interconnected protein network of de novo mutations. Nature 2012; 485: 246-250). A critical role of CHD8 in development is revealed by the embryonic lethality of CHD8 knockout mice (Nishiyama M, Oshikawa K, Tsukada Y, Nakagawa T, Iemura S, Natsume T et al. CHD8 suppresses p53-mediated apoptosis through histone H1 recruitment during early embryogenesis. Nat Cell Biol 2009; 11: 172-182). However, the function of CHD8 in neural cell lineages has been largely unexplored and mouse models targeting this gene have not been shown to exhibit ASD phenotypes.

CHD8 is an ATP-dependent chromatin remodeler (Thompson et al., 2008), has an atypical function compared to well-characterized monogenic ASD risk alleles and therefore holds promise to elucidate new aspects of ASD pathology. CHD8 appears to be involved in a range of developmental processes (Nishiyama et al., 2009; Nishiyama et al., 2012; Shanks et al., 2012; Terriente-Felix et al., 2011) and has been implicated in cancer (Kim et al., 2011; Subtil-Rodriguez et al., 2014). Early work into the function of CHD8 revealed that Chd8 homozygous null mice are embryonic lethal but heterozygous mice develop without any apparent abnormalities (Nishiyama et al., 2004). The first evidence of its role in ASD stemmed from identification of disruptive mutations within CHD8 in the minimal region within the 14q11.2 microdeletions found within two unrelated children with cognitive impairment and developmental delay (Zahir et al., 2007). Further evidence highlighting the importance of CHD8 in the brain was provided by investigations into balanced chromosomal abnormalities (Talkowski et al., 2012) and de novo exome sequencing (Iossifov et al., 2012; Neale et al., 2012; O'Roak et al., 2012a; O'Roak et al., 2012b; Sanders et al., 2012) of ASD patients. Interestingly, subsequent functional analysis utilizing shRNA-mediated knockdown of CHD8 in vitro in human cells indicated that CHD8 regulates many ASD risk genes involved in neurodevelopment and synaptic function (Tawalkski 2014, Cotney 2015, Wilkinson, 2015). Based on these lines of evidence, Bernier et al. performed targeted resequencing of 3,730 children with ASD or developmental delay and defined a subtype of ASD patients with mutations in CHD8 and specific phenotypes (Bernier et al., 2014).

There exists a pressing need for alternative and robust systems and techniques for experimental modeling of developmental (normal and pathological) events, conditions, disorders or diseases associated with multiple genetic loci or elements in animals to enable the study of the effects of specific, multiple genetic perturbations and/or mutagenic events in a step-wise (sequential) and/or simultaneous manner. Such events can include developmental steps such as those which specify lineage commitment steps in neuronal cells or any other cell type. Aspects of the present invention provide for ex vivo or in vivo modeling of developmental (normal and pathological) events or pathways, conditions, disorders or diseases associated with neuronal cells or tissues. Mutagenic events can include knock out events. Aspects of the present invention may address herein discussed challenges and need in the art by advantageously providing a CRISPR-based screening strategy ex vivo and/or in vivo to delineate gene networks that specify neuronal-specific pathways including pathways for development of the nervous system (including both central and peripheral nervous systems) and development of neuronal synapses, including e.g, assembly of scaffolding proteins in synapses. Aspects of the present invention further relate to systems, methods and compositions for delineating molecular components of neuronal synapses (e.g., scaffolding proteins and their assembly) and regulatory networks associated with human disorders and/or disease (e.g., autism, autism-spectrum disorders, obsessive compulsive disorder (OCD), psychiatric disorders or diseases), and uses thereof in research, diagnosis and therapy. Aspects of the present invention further relate to systems, methods and compositions for identifying novel target genes and novel pathways with respect to neuronal disorders and/or diseases such as autism, autism-spectrum disorders, OCD, psychiatric disorders or diseases. Further aspects relate to the association between neuronal development and onset or progression of such diseases or disorders. Aspects of the present invention provide systems, methods and compositions for experimentally inducing e.g., autism, autism-spectrum disorders, OCD, psychiatric disorders or diseases. Aspects of the present invention provide for elucidating or measuring various aspects of neurology relevant to any neuronal-cell or tissue associated developmental event, condition, disease or disorder.

Autism spectrum disorder (ASD) is associated with hundreds of genetic variants, but determining the causal mutations has been difficult due to the challenge of rapidly generating model systems to test risk alleles. It is an object of the present invention to provide for the rapid development of mouse models using CRISPR-Cas9. Applicants generated germline mutant mice with loss-of-function (LOF) mutations in Chd8, a de novo mutation strongly associated with ASD, and identified hallmark ASD-like behaviors as well as physiological and molecular abnormalities in medium spiny neurons of the nucleus accumbens (NAc), a ventral striatum subregion. It is another object of the present invention to provide cell type specific LOF animal models. To interrogate the underlying molecular mechanism of these behaviors Applicants genetically perturbed Chd8 in specific cells and brain regions in adult Cas9 mice. The results implicate loss of CHD8 expression in the NAc in the acquisition of repetitive behavior. Finally, it is an object of the present invention to demonstrate an important role of CHD8 in neurophysiology and establish a causal link between Chd8 mutations and hallmark ASD-like behavior in an animal model.

Aspects of the present invention provide methods, systems, compositions and models for ex vivo and in vivo genome editing of neuronal cells (e.g., in the brain), including editing simultaneously or sequentially two or more neuronal-associated genetic elements via a CRISPR-Cas based multiplexed genome editing approach. Aspects of the present invention provide methods, systems, compositions and models for ex vivo and in vivo genome modeling of multiple genetic, or tissue-specific genetic perturbations. Aspects of the invention provide methods for enabling rapid and direct in vivo and ex vivo modeling of the dynamics of multiple genetic, or tissue-specific developmental (normal or pathological) events, in particular those associated with neuronal cells or tissues. Aspects of the invention provide methods for neuronal cell or tissue replenishment in an animal or human subject in need thereof using neuronal cells modified using the CRISPR-Cas system. In certain non-limiting embodiments, a plurality of sgRNAs are delivered (e.g., via various means including a vector (e.g., AAV vector, lentiviral vector), a particle (e.g., nanoparticle) into neural stem cells (NSC) derived from Cas9 transgenic mice, and so obtained are transplanted into neuronal cell-deficient recipient animals or human. Aspects of the invention provide for use of mapping of neuronal cells, nervous system development studies, studying neuronal and related diseases/pathologies, and as research models/tools for prognostic, diagnostic and therapeutic purposes. Aspects of the invention provide methods for studying genetic loci associated with neurological conditions, e.g., screening host genes involved in psychiatric diseases, autism, autism-spectrum disorders, OCD, etc. Aspects of the invention provide methods for screening for regulatory networks controlled by transcription factors, neuronal-cell type-specific promoters/enhancers, and super-enhancers associated with human development and/or disease. Aspects of the invention provide for methods for elucidating fate mapping strategies in vivo, e.g., neuronal cell lineage studies. Aspects of the invention provide for studying neuronal function, including e.g., assembly of scaffolding proteins, synapse creation, signaling, and/or elimination, etc. Aspects of the invention provide for studying genes involved in predisposition to neuronal-associated diseases or disorders (e.g., psychiatric disorders). Aspect of the invention provide methods, systems, compositions for prophylaxis and/or treatment of neuronal-associated diseases or disorders (e.g., psychiatric diseases, autism, autism-spectrum disorders, OCD). Aspects of the present invention involve sequence targeting, such as genome perturbation or induction of multiple mutations using the Clustered Regularly Interspaced Short Palindromic Repeats (CRISPR) system or components thereof. The invention provides systematic reverse engineering of causal genetic variations, including through selective perturbation of individual, and moreover, multiple genetic elements. For instance, in non-human eukaryote, e.g., animal, such as fish, e.g., zebra fish; mammal, e.g., primate, e.g., ape, chimpanzee, macaque; rodent, e.g., mouse, rabbit, rat; canine or dog; livestock (cow/bovine, sheep/ovine, goat or pig); fowl or poultry, e.g., chicken; insect; arthropod or plant, e.g., dicot (e.g., nightshade such as tobacco, tuber such as potato) or monocot (e.g., corn) models, that constitutively or through induction or through administration or delivery, have cells that contain Cas9. The invention provides tools for studying genetic interaction between multiple individual genetic elements by allowing selective perturbation of, e.g., one or more neuronal/nervous system-associated or correlated gene(s)/genetic element(s). In an aspect, the invention provides methods for using one or more elements/components of a CRISPR-Cas system via a vector and/or particle and/or nanoparticle delivery formulation or system as a means to modify a target polynucleotide. In preferred embodiments, the delivery is via a viral vector (e.g., AAV, adenovirus, lentivirus). The CRISPR complex of the invention provides an effective means for modifying a target polynucleotide. The CRISPR complex of the invention has a wide variety of utilities including modifying (e.g., deleting, inserting, recombining, translocating, inactivating, activating) a target polynucleotide in a multiplicity of cell types in various tissues and organs, e.g., neuronal cells. As such the CRISPR complex of the invention has a broad spectrum of applications in modeling of multiple genetic, or tissue-specific mutations, and hence gene therapy, drug discovery, drug screening, disease diagnosis, and prognosis.

It will be appreciated that in the present methods, where the non-human transgenic Cas9 organism is multicellular, e.g., an animal or plant, the modification may occur ex vivo or in vitro, for instance in a cell culture and in some instances not in vivo. In other embodiments, it may occur in vivo. In an aspect, the invention provides a method of modifying an organism or a non-human organism by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition. The composition can comprise: A) I. RNA(s) having polynucleotide sequence(s), e.g., a CRISPR-Cas system chimeric RNA (chiRNA) having polynucleotide a sequence, wherein the polynucleotide sequence comprises: (a) a guide sequence capable of hybridizing to a target sequence in a eukaryotic cell, (b) a tracr mate sequence, and (c) a tracr sequence; wherein (a), (b) and (c) are arranged in a 5' to 3' orientation. The composition can also comprise A) II. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridizable to the target sequence, and (2) the tracr mate sequence that is hybridizable to the tracr sequence. The polynucleotide sequence encoding a CRISPR enzyme is DNA or RNA. When the Cas9 is already present in the cell, e.g., through the cell having already been provided (A) II. or through the cell expressing Cas9, e.g., through the cell having been transformed to express Cas9, e.g., Cas9 is expressed constitutively or conditionally or inducibly—for instance when the cell is part of or from a non-human transgenic eukaryote, e.g., animal, mammal, primate, rodent, etc as herein discussed—then (A) I. is provided as the CRISPR complex is formed in situ or in vivo. In an aspect, the invention provides a method of modifying an organism or a non-human organism by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition. The composition can comprise (B) I. polynucleotides comprising: (a) a guide sequence capable of hybridizing to a target sequence in a eukaryotic cell, and (b) at least one or more tracr mate sequences. The composition can also comprise (B) II. a polynucleotide sequence comprising a tracr sequence. The composition can also comprise (B) III. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence. The CRISPR complex comprises the CRISPR enzyme complexed with (1) the guide sequence that is hybridizable to the target sequence, and (2) the tracr mate sequence that is hybridizable to the tracr sequence, and the polynucleotide sequence encoding a CRISPR enzyme is DNA or RNA. When the Cas9 is already present in the cell, e.g., through the cell having already been provided (B) III. or through the cell expressing Cas9, e.g., through the cell having been transformed to express Cas9, e.g., Cas9 is expressed constitutively or conditionally or inducibly—for instance when the cell is part of or from a non-human transgenic eukaryote, e.g., animal, mammal, primate, rodent, etc as herein discussed—then (B) I. and (B) II. are provided as the CRISPR complex is formed in situ or in vivo. Accordingly, components I and II or I, II and III or the foregoing embodiments can be delivered separately; for instance, in embodiments involving components I, II and III, components I and II can be delivered together, while component II can be delivered separately, e.g., prior to components I and II, so that the cell or eukaryote expresses Cas9. It will be further appreciated that heretofore it could not be expected that multiple, specific mutations, especially in the numbers herein discussed, e.g., 3-50 or more, or 3, 16, 32, 48 or 50 or more, could be able to be achieved. In undertaking embodiments of the invention, the Applicants have indeed divined that such multiple mutations are present in significant numbers of cells of the non-human eukaryote. For instance, it was surprising and unexpected that cells and tumors of the non-human transgenic organisms of the invention could have multiple mutations of the delivered RNA(s) (sgRNAs); indeed, all of the multiple mutations.

In some embodiments the invention comprehends delivering a CRISPR enzyme comprising delivering to a cell mRNA encoding the CRISPR enzyme, e.g., via nanoparticle complex(es). In some of these methods the CRISPR enzyme is a Cas9. In certain preferred embodiments the Cas9 enzyme is constitutively present, e.g., through knock-in. Thus, in a preferred embodiment of the invention, the Cas9 enzyme is constitutively present in vivo (e.g, a non-human transgenic eukaryote, animal, mammal, primate, rodent, etc) or ex vivo (cells comprising a vector containing nucleic acid molecule(s) for in vivo expression of the Cas9). The CRISPR enzyme is a type I or III CRISPR enzyme, preferably a type II CRISPR enzyme. This type II CRISPR enzyme may be any Cas enzyme. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, SpCas9 or SaCas9. It will be appreciated that SpCas9 or SaCas9 are those from or derived from *S. pyogenes* or *S. aureus* Cas9. By derived, Applicants mean that the derived enzyme is largely based, in the sense of having a high degree of sequence homology with, a wildtype enzyme, but that it has been mutated (modified) in some way as described herein It will be appreciated that the terms Cas and CRISPR enzyme are generally used herein interchangeably, unless otherwise apparent. The Cas enzyme can be for instance any naturally-occurring bacterial Cas9 as well as any chimaeras, mutants, homologs or orthologs. Many of the residue numberings used herein refer to the Cas9 enzyme from the type II CRISPR locus in *Streptococcus pyogenes* (annotated alternatively as SpCas9 or spCas9). However, it will be appreciated that this invention includes many more Cas9s from other species of microbes, e.g., orthologs of SpCas9, or Cas9s derived from microbes in addition to *S. pyogenes*, e.g., SaCas9 derived from *S. aureus*, St1Cas9 derived from *S. thermophilus* and so forth. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence. The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Francisella novicida* type II CRISPR locus), and the conserved Asp residue (D10) is mutated to alanine to convert Cas9 into a complementary-strand nicking enzyme. Similarly, the conserved His and Asn residues in the HNH domains are mutated to Alanine to convert Cas9 into a non-complementary-strand nicking enzyme. In some embodiments, both sets of mutations may be made, to convert Cas9 into a non-cutting enzyme. Thus, the Cas9 may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the CRISPR enzyme or has a mutation as otherwise as discussed herein. In one aspect of the invention, the Cas9 enzyme may be fused to a protein, e.g., a TAG, and/or an inducible/controllable domain such as a chemically inducible/controllable domain. The Cas9 in the invention may be a chimeric Cas9 proteins; e.g., a Cas9 having enhanced function by being a chimera. Chimeric Cas9 proteins may be new Cas9 containing fragments from more than one naturally occurring Cas9. These may comprise fusions of N-terminal fragment(s) of one Cas9 homolog with C-terminal fragment(s) of another Cas9 homolog. The Cas9 can be delivered into the cell in the form of mRNA. The expression of Cas9 can be under the control of an inducible promoter.

The tracrRNA and direct repeat sequences can be mutant sequences or the invention can encompass RNA of the CRISPR-Cas system that includes mutant chimeric guide sequences that allow for enhancing performance of these RNAs in cells. A suitable promoter, such as the Pol III promoter, such as a U6 promoter, can be added onto the guide RNA that is advantageously delivered via AAV or particle or nanoparticle. Aspects of the invention also relate to the guide RNA being transcribed in vitro or ordered from a synthesis company and directly transfected. Expression of RNA(s), e.g., guide RNAs or sgRNA under the control of the T7 promoter driven by the expression of T7 polymerase in the cell is also envisioned. In an advantageous embodiment, the cell is a eukaryotic cell. In a preferred embodiment the eukaryotic cell is a human cell. In a more preferred embodiment the cell is a patient-specific cell, e.g., a cell in which 3-50 or more mutations associated or correlated with a patient's genetic disease, e.g., a neuronal/neurological disease, are expressed in the cell, e.g., via Cas9 being present in the cell and RNA(s) for such mutations delivered to the cell (e.g., any whole number between 3 and 50 of mutations, with it noted that in some embodiments there can be up to 16 different RNA(s), e.g., sgRNAs, e.g., each having its own a promoter, in a vector, such as AAV, adenovirus or lentivirus, and that when each sgRNA does not have its own promoter, there can be twice to thrice that amount of different RNA(s), e.g., sgRNAs, e.g., 32 or even 48 different guides delivered by one vector, whereby the CRISPR-Cas complexes result in the cells having the mutations and the cells and the eukaryote, e.g., animal, containing the cells being a model for the patient's genetic disease.

Multiple mutations may thus be introduced using any number of sgRNAs, e.g. the vector may comprise at least 3 sgRNAs, at least 8 sgRNAs, at least 16 sgRNAs, at least 32 sgRNAs, at least 48 sgRNAs, or at least 50 sgRNAs. Alternatively, the vector may comprise 1-2 sgRNAs, 1-3 sgRNAs, 1-4 sgRNAs, 1-5 sgRNAs, 3-6 sgRNAs, 3-7 sgRNAs, 3-8 sgRNAs, 3-9 sgRNAs, 3-10 sgRNAs, 3-16 sgRNAs, 3-30 sgRNAs, 3-32 sgRNAs, 3-48 sgRNAs or 3-50 sgRNAs. The mutation(s) can include the introduction, deletion, or substitution of one or more nucleotides at each target sequence of cell(s) via the guide(s) or RNA(s) or sgRNA(s) resulting in loss-of-function and/or gain-of-function of the target(s). The mutations can include the introduction, deletion, or substitution of 1-75 nucleotides at each target sequence of said cell(s) via the guide(s) or RNA(s) sgRNA(s) resulting in loss-of-function or gain-of-function of the target(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations can include the introduction, deletion, or substitution of 40, 45, 50, 75, 100, 200, 300, 400 or 500 nucleotides at each target sequence of said cell(s) via the guide(s) or RNA(s) or sgRNA(s) resulting in loss-of-function or gain-of-function of the target.

A codon optimized sequence can be a sequence optimized for a eukaryote, or for specific organs or cell types such as neuronal cells. It will be appreciated that where reference is made to a polynucleotide, where that polynucleotide is RNA and is said to 'comprise' a feature such as a tracr mate sequence, the RNA sequence includes the feature. Where the polynucleotide is DNA and is said to comprise a feature such as a tracr mate sequence, the DNA sequence is or can be transcribed into the RNA that comprises the feature at issue. Where the feature is a protein, such as the CRISPR enzyme, the DNA or RNA sequence referred to is, or can be, translated (and in the case of DNA transcribed first). Furthermore, in cases where an RNA encoding the CRISPR enzyme is provided to a cell, it is understood that the RNA is capable of being translated by the cell into which it is delivered. By manipulation of a target sequence, Applicants mean the alteration of the target sequence, which may include the epigenetic manipulation of a target sequence. This epigenetic manipulation may be of the chromatin state of a target sequence, such as by modification of the methylation state of the target sequence (i.e. addition or removal of methylation or methylation patterns or CpG islands), histone modification, increasing or reducing accessibility to the target sequence, or by promoting 3D folding. It will be appreciated that where reference is made to a method of modifying an organism or mammal including human or a non-human mammal or organism by manipulation of a target sequence in a genomic locus of interest, this may apply to the organism (or mammal) as a whole or just a single cell or population of cells from that organism (if the organism is multicellular). Applicants envisage, inter alia, a single cell or a population of cells and these may preferably be modified ex vivo and then re-introduced, e.g., transplanted to make transgenic organisms that express Cas9 in certain cells. The invention in some embodiments comprehends a method of modifying a eukaryote, such as a Cas9 transgenic eukaryote comprising delivering, e.g., via vector(s) and/or particle(s) and/or nanoparticles a non-naturally occurring or engineered composition. The composition comprises: I. a first regulatory element operably linked to (a) a first guide sequence capable of hybridizing to a first target sequence, and (b) at least one or more tracr mate sequences, II. a second regulatory element operably linked to (a) a second guide sequence capable of hybridizing to a second target sequence, and (b) at least one or more tracr mate sequences, III. a third regulatory element operably linked to (a) a third guide sequence capable of hybridizing to a third target sequence, and (b) at least one or more tracr mate sequences, and IV. a fourth regulatory element operably linked to a tracr sequence. There can be additional regulatory element(s) operably linked to additional guide sequence(s). Optionally, the composition can involve V. a fifth regulatory element operably linked to an enzyme-coding sequence encoding a CRISPR enzyme (e.g., for establishing the Cas9 transgenic eukaryote). Components I, II, III and IV (as well as any other regulatory element(s) linked to additional guide sequence(s)) are located on the same or different vectors and/or particles and/or nanoparticles of the system. When transcribed, the tracr mate sequence hybridizes to the tracr sequence and the first, second and the third guide sequences direct sequence-specific binding of a first, second and a third CRISPR complexes to the first, second and third target sequences respectively, wherein the first CRISPR complex comprises the CRISPR enzyme complexed with (1) the first guide sequence that is hybridizable to the first target sequence, and (2) the tracr mate sequence that is hybridizable to the tracr sequence, wherein the second CRISPR complex comprises the CRISPR enzyme complexed with (1) the second guide sequence that is hybridizable to the second target sequence, and (2) the tracr mate sequence that is hybridizable to the tracr sequence, and wherein the third CRISPR complex comprises the CRISPR enzyme complexed with (1) the third guide sequence that is hybridizable to the third target sequence, and (2) the tracr mate sequence that is hybridizable to the tracr sequence, whereby in a Cas9 transgenic eukaryote or cell thereof, at least three (3) mutations may be induced, and advantageously the mutations are correlated or associated with a genetic disease condition, whereby the eukaryote or cell becomes a model of the disease, e.g., model for an neuronal/neurological disorder or disorder, e.g., autism, autism-spectrum disorders, obsessive compulsive disorder (OCD), psychiatric disorders or diseases. The invention also provides a vector system as described herein. The system may comprise one, two, three or four different vectors; and the system may comprise one, two, three or four different nanoparticle complex(es) delivering the component(s) of the system. Components I, II, III and IV may thus be located on one, two, three or four different vectors, and may be delivered by one, two, three or four different particle or nanoparticle complex(es) or AAVs or components I, II, III and IV can be located on same or different vector(s)/particle(s)/nanoparticle(s), with all combinations of locations envisaged. Complexes that target neuronal tissue or cells are advantageous.

In some methods of the invention any or all of the polynucleotide sequence encoding the CRISPR enzyme, the first and the second guide sequence, the first and the second tracr mate sequence or the first and the second tracr sequence, is/are RNA; and advantageously delivered via nanoparticle complex(es). Embodiments of the invention also comprehend the guide RNAs comprising a guide sequence fused to a tracr mate sequence and a tracr sequence. In an aspect of the invention the Cas protein is codon optimized for expression in a eukaryotic cell, preferably a mammalian cell or a human cell. The invention also comprehends an engineered, non-naturally occurring vector system. The system comprises one or more vectors comprising: (a) a first regulatory element operably linked to each of two or more e.g. three, CRISPR-Cas system guide RNAs that target a first strand, a second strand and a third strand respectively of a double stranded DNA molecule. The system can also comprise (b) a second regulatory element operably linked to a Cas protein. Components (a) and (b) are located on same or different vectors of the system, but advantageously separate vectors as it is preferred that cells receiving (a) contain Cas9, e.g., via the cells being those of a transgenic Cas9 eukaryote (whereby (b) may have been administered to cells that gave rise to the eukaryote). The guide RNAs target DNA and at least three mutations are induced in the cells, e.g., mutations correlated to or associated with a genetic disorder such as a neuronal/neurological disease or disorder (e.g., autism, autism-spectrum disorders, obsessive compulsive disorder (OCD), psychiatric disorders or diseases). In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence; and advantageously the complex or a component thereof has been delivered via nanoparticle complex(es). In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. The mutation can be a mutation correlated to or associated with a genetic disease condition, such as a neuronal/neurological disease or disorder, such as autism, autism-spectrum disorders, obsessive compulsive disorder (OCD), psychiatric disorders or diseases or with neuronal-associated developmental issues.

In some embodiments, said mutation results in one or more amino acid changes in a protein expressed from a gene comprising the target sequence. In some embodiments, vectors are delivered to the eukaryotic cell in a transgenic Cas9 eukaryote. In some embodiments, said modifying takes place in said eukaryotic cell in a cell culture. In one aspect, the invention provides a method of generating a model eukaryotic cell or a model Cas9 transgenic eukaryote comprising mutated disease gene(s), e.g., having 3-50 mutations correlated to or associated with a genetic disease such as a neuronal/neurological disorder, such autism, autism-spectrum disorders, obsessive compulsive disorder (OCD), psychiatric disorders or diseases. (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector). In some embodiments, a disease gene is any gene associated with an increase in the risk of having or developing a disease.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In certain embodiments, the target sequence is flanked or followed, at its 3' end, by a PAM suitable for the CRISPR enzyme, typically a Cas and in particular a Cas9. For example, a suitable PAM is 5'-NRG or 5'-NNGRR for SpCas9 or SaCas9 enzymes (or derived enzymes), respectively.

Delivery can be in the form of a vector which may be a plasmid or other nucleic acid molecule form, especially when the delivery is via a nanoparticle complex; and the vector also can be viral vector, such as a herpes, e.g., herpes simplex virus, lenti- or baculo- or adeno-viral or adeno-associated viral vectors, but other means of delivery are known (such as yeast systems, microvesicles, gene guns/means of attaching vectors to gold nanoparticles) and are provided, especially as to those aspects of the complex not delivered via a nanoparticle complex. A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell; and advantageously the complex or a component thereof is delivered via nanoparticle complex(es). Also envisaged is a method of delivering the present CRISPR enzyme comprising delivering to a cell mRNA encoding the CRISPR enzyme; and advantageously the complex or a component thereof has been delivered via nanoparticle complex(es). It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed. When not delivering via a nanoparticle complex, AAV is a preferred vector. In certain embodiments, multiple RNA(s) or guide RNAs or sgRNAs formulated in one or more delivery vehicles (e.g., where some guide RNAs are provided in a vector and others are formulated in nanoparticles); and these may be provided alone (e.g., when Cas9 is already in a cell) or with a Cas9 delivery system. In certain embodiments, the Cas9 is also delivered in a nanoparticle formulation. In certain instances the RNA(s) or guide RNA or sgRNA-vector and/or particle and/or nanoparticle formulation(s) and the Cas9 vector and/or particle and/or nanoparticle formulation(s) may be delivered separately or may be delivered substantially contemporaneously (i.e., co-delivery). Sequential delivery could be done at separate points in time, separated by days, weeks or even months. And as Cas9 is advantageously present in a transgenic organism in the practice of the invention, e.g., through being constitutively or conditionally or inducibly present, sequential delivery can include initially administering or delivering the Cas9 vector and/or particle and/or nanoparticle formulation(s) to cells that give rise to the non-human Cas9 transgenic eukaryote, and thereafter, at a suitable time in the life of the transgenic eukaryote, administering the RNA(s) or guide RNA or sgRNA-vector and/or particle and/or nanoparticle formulation(s), e.g., so as to give rise to one or more, advantageously 3-50 mutations in the transgenic eukaryote (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), and advantageously the mutations are associated or correlated with a genetic disease, whereby the transgenic eukaryote is a model of the genetic disease, e.g., a neuronal-associated developmental issue or a neuronal/neurological disease or disorder, such as autism, autism-spectrum disorders, obsessive compulsive disorder (OCD), psychiatric disorders or diseases. In certain embodiments, vector (e.g., AAV, adenovirus, lentivirus) and/or particle and/or nanoparticle formulations comprising one or more RNA(s) e.g. guide RNAs or sgRNA are adapted for delivery in vitro, ex vivo or in vivo in the context of the CRISPR-Cas system, e.g., so as to form CRISPR-Cas complexes in vitro, ex vivo or in vivo, to different target genes, different target cells or different target different tissues/organs, with different target genes and/or cells of a neuronal/neurological disease or disorder, such as autism, autism-spectrum disorders, obsessive compulsive disorder (OCD), psychiatric disorders or diseases. Multiplexed gene targeting using nanoparticle formulations comprising one or more guide RNAs are also envisioned. In an embodiment, a nanoparticle formulation comprising one or more components of the CRISPR-Cas system is provided. In an embodiment, a RNA(s) or gRNA or sgRNA-nanoparticle formulation comprising one or more guide RNAs or sgRNA is provided. In certain embodiments, a composition comprising a nanoparticle formulation comprising one or more components of the CRISPR-Cas system is provided. In certain embodiments, a composition, e.g., a pharmaceutical or veterinary composition, comprising a vector (e.g., AAV, adenovirus, lentivirus) and/or particle and/or nanoparticle formulation comprising one or more components of the CRISPR-Cas system and/or nucleic acid molecule(s) coding therefor, advantageously with such nucleic acid molecule(s) operably linked to promoter(s) is provided. Accordingly, in certain embodiments, it may be useful to deliver the RNA(s) or guide RNA or sgRNA, e.g., vector and/or particle and/or nanoparticle formulations separately from the Cas9 or nucleic acid molecule(s) coding therefor. A dual-delivery system is envisaged such that the Cas 9 may be delivered via a vector and the RNA(s), e.g., guide RNAs or sgRNA are/is provided in a particle or nanoparticle formulation, for example, first Cas9 vector is delivered via a vector system followed by delivery of sgRNA-nanoparticle formulation. Vectors may be considered in the broadest light as simply any means of delivery, rather than specifically viral vectors.

In one aspect, the present invention provides a Cas9 transgenic eukaryote, e.g., mouse. In certain preferred embodiments, the Cas 9 transgenic eukaryote, e.g., mouse comprises a Cas9 transgene knocked into the Rosa26 locus. In one aspect, the present invention provides a Cas9 transgenic eukaryote, e.g., mouse wherein Cas9 transgene is driven by the ubiquitous CAG promoter thereby providing for constitutive expression of Cas9 in all tissues/cells/cell types of the mouse. In one aspect, the present invention provides a Cas9 transgenic eukaryote, e.g., mouse wherein the Cas9 transgene driven by the ubiquitous CAG promoter further comprises a Lox-Stop-polyA-Lox (LSL) cassette (Rosa26-LSL-Cas9 mouse) thereby rendering Cas9 expression inducible by the Cre recombinase. In one aspect, the present invention provides a constitutive Cas9 expressing eukaryote, e.g., mouse line obtained by crossing of the Rosa26-LSL-Cas9 mouse with a beta-actin-Cre eukaryote, e.g., mouse line. In certain embodiments, progeny (or progenies) derived from said Cas9 expressing eukaryote, e.g., mouse line, may be successfully bred over at least five generations without exhibiting increased levels of genome instability or cellular toxicity. In one aspect, the present invention provides a modular viral vector construct comprising a plurality of sgRNAs driven by a single RNA polymerase III promoter (e.g., U6), wherein the sgRNAs are in tandem, or where each of the sgRNAs is driven by one RNA polymerase III promoter. In one aspect, the present invention provides a modular viral vector construct comprising one or more cassettes expressing Cre recombinase, a plurality of sgRNAs to guide Cas9 cutting, and optionally including a Homology Directed Repair (HDR) template to model the dynamics of a complex pathological disease or disorder involving two or more genetic elements simultaneously using a single vector construct (in embodiments where the HDR template is not involved, the cutting creates the mutation to model the dynamics of a complex pathological disease or disorder (e.g., loss-of-function or gain-of-function). In certain non-limiting embodiments, the complex pathological disease or disorder is a neuronal/neurological disease or disorder, such as autism, autism-spectrum disorders, obsessive compulsive disorder (OCD), psychiatric disorders or diseases. It can be appreciated that any kind of genetic perturbation of any tissue type are within the scope of the present invention. In a preferred embodiment, the present invention provides for modeling of a neuronal/neurological disease or disorder, such as autism, autism-spectrum disorders, obsessive compulsive disorder (OCD), psychiatric disorders or diseases. In one aspect, the present invention provides a modular viral vector construct to model the dynamics of a neuronal/neurological disease or disorder such as autism, autism-spectrum disorders, obsessive compulsive disorder (OCD), psychiatric disorders or diseases simultaneously using a single vector. In certain embodiments, the modular viral vector construct comprises one or more cassettes expressing Cre recombinase, a plurality of sgRNAs to guide Cas9 cutting, and optionally one or more Homology Directed Repair (HDR) template(s) to introduce specific gain-of-function mutations or precise sequence substitution in target loci. In one aspect, the present invention provides a method for simultaneously introducing multiple mutations ex vivo in a tissue, organ or a cell line, or in vivo in the same animal comprising delivering a single viral vector construct, wherein the viral vector construct comprises one or more cassettes expressing Cre recombinase, a plurality of sgRNAs to guide Cas9 cutting, and optionally HDR template(s) for achieving targeted insertion or precise sequence substitution at specific target loci of interest. It can be readily appreciated that mutations in any gene(s), including genetic control elements (promoters, enhancers)) associated with a neuronal/neurological disease or disorder e.g., autism, autism-spectrum disorders, obsessive compulsive disorder (OCD), psychiatric disorders or diseases is within the scope of the present invention. In one aspect, the present invention provides a method for delivering ex vivo or in vivo of any of the constructs disclosed herein using a viral vector.

In certain preferred embodiments, AAV is used for delivery to neuronal cells or tissues (e.g., brain). In one aspect, the present invention provides a method for ex vivo and/or in vivo genome editing comprising delivering any of the above modular viral vector constructs, which comprise one or more cassettes expressing Cre recombinase, a plurality of sgRNAs to guide Cas9 cutting, and optionally one or more HDR template(s), into a Cas9 transgenic mouse (e.g., Rosa26-LSL-Cas9). In certain embodiments, the viral vector is AAV, adenovirus or lentivirus. In one aspect, the present invention provides a Cas9 transgenic non-human eukaryote, e.g., animal model for neuronal development and/or for a neuronal/neurological disease or disorder, such as autism, autism-spectrum disorders, obsessive compulsive disorder (OCD), psychiatric disorders or diseases said model having loss-of-function mutations in neuronal cells and/or gain-of-function mutation in neuronal cells. It can be appreciated that using the novel CRISPR-Cas9 tools disclosed herein, Cas9 transgenic non-human eukaryote, e.g., animal model with multiple mutations in any number of loci can be envisioned and are within the scope of the present invention. It will be appreciated that such a transgenic non-human eukaryote, e.g., animal model provides a valuable tool for research purposes, e.g., to delineate specific roles/contribution of individual mutations to a neuronal/neurological development, disease or disorder, such as autism, autism-spectrum disorders, obsessive compulsive disorder (OCD), psychiatric disorders or diseases progression, to recapitulate specific combinations of mutations in a given disorder type, and opens the door for developing and testing new therapeutic interventions for disorders involving mutations at multiple loci. Such uses are within the scope of the present invention. In one aspect, the present invention provides a method of treating or inhibiting the development of a genetic disease in a subject in need thereof, comprising providing individualized or personalized treatment (or an individualized or personalized model or patient specific-modeling) comprising: delivering RNA(s), e.g., sgRNA, that targets a genetic locus correlated or associated with the genetic disease, e.g., a neuronal/neurological disease or disorder, such as autism, autism-spectrum disorders, obsessive compulsive disorder (OCD), psychiatric disorders or diseases to a Cas9 non-human transgenic eukaryote (e.g., animal, mammal, primate, rodent, fish etc as herein discussed), e.g., via vector such as AAV, adenovirus, lentivirus, or particle(s) or nanoparticle(s), whereby mutation(s), advantageously a plurality, e.g., 3-50 mutations (e.g., any whole number between 3 and 50 of mutations, with it noted that in some embodiments there can be up to 16 different RNA(s), e.g., sgRNAs each having its own a promoter, in a vector, such as AAV, adenovirus or lentivirus, and that when each sgRNA does not have its own promoter, there can be twice to thrice that amount of different RNA(s), e.g., sgRNAs, e.g., 32 or even 48 different guides delivered by one vector), are induced in the eukaryote and the eukaryote is a model for the disease; and obtaining and/or extrapolating data from the Cas9 non-human transgenic eukaryote to humans to provide individualized or personalized treatment. The obtaining and/or extrapolating data can be subjecting the eukaryote to putative treatment(s) and/or therapy(ies), e.g., gene therapy, ascertaining whether such putative treatment(s) and/or therapy(ies) give rise to remission or treatment or alleviation or mitigation or stasis of the disease, and if so, then administering in dosing scaled to a 70 kg individual or subject, the putative treatment(s) and/or therapy(ies). The invention thus allows for one to ascertain whether a particular treatment and/or therapy may be effective as to a particular individual's disease.

In certain aspects the invention provides vector(s), particle(s) or nanoparticle(s) containing nucleic acid molecule(s), whereby in vivo in a eukaryotic cell containing or conditionally or inducibly expressing Cas9: the vector(s) express(es) a plurality of RNAs to guide the Cas9 and optionally delivers donor templates (e.g., HDR templates, and in certain embodiments advantageously includes and delivers such donor templates), and optionally in the event Cas9 is conditionally or inducibly expressed in the cell that which induces Cas9, e.g., Cre recombinase; whereby a plurality of specific mutations or precise sequence substitutions in a plurality of target loci are introduced. The donor template(s) may introduce one or more sequence alterations, wherein the sequence alteration(s) are selected from mutations and repair to wild type, in one or more target genetic loci in the target cell, thereby modulating expression of one or more genes in the target cell. The vector(s) can be a viral vector such as lentivirus, adenovirus, or adeno-associated virus (AAV), e.g., AAV6 or AAV9. The Cas9 can be from *S. thermophiles*, *S. aureus*, or *S. pyogenes*. The eukaryotic cell can comprise a Cas9 transgene is functionally linked to a constitutive promoter, or a tissue specific promoter, or an inducible promoter; and, the eukaryotic cell can be part of a non-human transgenic eukaryote, e.g., a non-human mammal, primate, rodent, mouse, rat, rabbit, canine, dog, cow, bovine, sheep, ovine, goat, pig, fowl, poultry, chicken, fish, insect or arthropod; advantageously a mouse. The isolated eukaryotic cell or the non-human transgenic eukaryote can express an additional protein or enzyme, such as Cre; and, the expression of Cre can be driven by coding therefor functionally or operatively linked to a constitutive promoter, or a tissue specific promoter, or an inducible promoter.

The RNAs to guide Cas9 can comprise CRISPR RNA and transactivating (tracr) RNA. The tracr mate and the tracr sequence can be connected to form a transactivating (tracer) sequence. The tracr mate and the tracr sequence can optionally be designed to form a single guide RNA (sgRNA). Indeed, it is advantageous that the RNAs to guide Cas9 can comprise chimeric single guide RNA (sgRNA). The tracr sequence and tracr mate sequence along the length of the shorter of the two when optimally aligned can be about or more than about 25%, 30%, 40%, 50%, 60%, 70%, 80%, 90%, 95%, 97.5%, 99%, or higher. The tracr sequence can be about or more than about 5, 6, 7, 8, 9, 10, 11, 12, 13, 14, 15, 16, 17, 18, 19, 20, 25, 30, 40, 50, or more nucleotides in length. The degree of complementarity between a guide sequence and its corresponding target sequence can be about or more than about 50%, 60%, 75%, 80%, 85%, 90%, 95%, 97.5%, 99%, or 100%. A guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. A guide or RNA or sgRNA can be less than about 75, 50, 45, 40, 35, 30, 25, 20, 15, 12, or fewer nucleotides in length.

The vector(s) can include the regulatory element(s), e.g., promoter(s). The vector(s) can comprise at least 3 or 8 or 16 or 32 or 48 or 50 RNA(s) (e.g., sgRNAs), such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences.

And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html)

In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters—especially as to the numbers of RNAs or guides or sgRNAs discussed herein, without any undue experimentation.

The RNA(s), e.g., sgRNA(s), can be functionally or operatively linked to regulatory element(s) and hence the regulatory element(s) drive expression. The promoter(s) can be constitutive promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Advantageously, each RNA (e.g., sgRNA) is specific to a different target sequence. Each different target sequence can be associated with or correlated to a form of a neuronal/neurological disease or disorder. Each sgRNA can be driven by an independent promoter, e.g., U6 promoter. The vector can be viral vector, e.g., AAV, adenovirus or lentivirus. Each of the sgRNAs can target a different genetic locus associated with a multigenic disease or disorder, e.g., a neuronal/neurological disease or disorder, such as autism, autism-spectrum disorders, obsessive compulsive disorder (OCD), psychiatric disorders or diseases. The sgRNAs can target one or more genes involved in a neuronal/neurological disease or disorder, such as autism, autism-spectrum disorders, obsessive compulsive disorder (OCD), psychiatric disorders or diseases etc. so as to introduce loss-of-function mutations. The sgRNAs can target one or more genes involved in a neuronal/neurological disease or disorder, such as autism, autism-spectrum disorders, obsessive compulsive disorder (OCD), psychiatric disorders or diseases as to introduce a loss-of-function mutation. The sgRNAs can target one or more of loci involved in genes involved in a neuronal/neurological disease or disorder, such as autism, autism-spectrum disorders, obsessive compulsive disorder (OCD), psychiatric disorders or diseases. From 3 to 50 specific mutations or precise sequence substitutions in from 3 to 50 target loci can be introduced. The eukaryotic cell can be a mammalian cell, e.g., a mouse cell, such as a mouse cell that is part of a transgenic mouse having cells that express Cas9. The invention also comprehends a method for introducing multiple mutations ex vivo in a tissue, organ or a cell line comprising Cas9-expressing eukaryotic cell(s), or in vivo in a transgenic non-human mammal having cells that express Cas9, comprising delivering to cell(s) of the tissue, organ, cell or mammal the vector as herein-discussed. The method can comprise delivering to cells of the transgenic non-human mammal, and the transgenic non-human mammal is a transgenic mouse having cells that express Cas9, e.g., a mouse that has had a Cas9 transgene knocked into the Rosa26 locus. The Cas9 transgene can further comprise a Lox-Stop-polyA-Lox (LSL) cassette thereby rendering Cas9 expression inducible by Cre recombinase. The invention additionally comprehends a method for modeling a genes involved in a neuronal/neurological disease or disorder, such as autism, autism-spectrum disorders, obsessive compulsive disorder (OCD), psychiatric disorders or diseases comprising introducing multiple mutations ex vivo in a tissue, organ or a cell line comprising Cas9-expressing eukaryotic cell(s), or in vivo in a transgenic non-human mammal having cells that express Cas9, comprising delivering to cell(s) of the tissue, organ, cell or mammal the vector as herein-discussed, wherein the specific mutations or precise sequence substitutions are or have been correlated to genes involved in a neuronal/neurological disease or disorder, such as autism, autism-spectrum disorders, obsessive compulsive disorder (OCD), psychiatric disorders or diseases. This method can comprise delivering to cells of the transgenic non-human mammal the vector, and the transgenic non-human mammal is a transgenic mouse having cells that express Cas9, e.g., a mouse that has had a Cas9 transgene knocked into the Rosa26 locus; and, the Cas9 transgene can further comprise a Lox-Stop-polyA-Lox (LSL) cassette thereby rendering Cas9 expression inducible by Cre recombinase. The invention also envisions an individualized or personalized treatment of genes involved in a neuronal/neurological disease or disorder, such as autism, autism-spectrum disorders, obsessive compulsive disorder (OCD), psychiatric disorders or diseases in a subject in need of such treatment comprising: (a) introducing multiple mutations ex vivo in a tissue, organ or a cell line comprising Cas9-expressing eukaryotic cell(s), or in vivo in a transgenic non-human mammal having cells that express Cas9, comprising delivering to cell(s) of the tissue, organ, cell or mammal the vector as herein-discussed, wherein the specific mutations or precise sequence substitutions are or have been correlated to genes involved in a neuronal/neurological disease or disorder, such as autism, autism-spectrum disorders, obsessive compulsive disorder (OCD), psychiatric disorders or diseases; (b) testing treatment(s) for genes involved in a neuronal/neurological disease or disorder, such as autism, autism-spectrum disorders, obsessive compulsive disorder (OCD), psychiatric disorders or diseases on the cells to which the vector has been delivered that have the genes involved in a neuronal/neurological disease or disorder, such as autism, autism-spectrum disorders, obsessive compulsive disorder (OCD), psychiatric disorders or diseases specific mutations or precise sequence substitutions correlated to genes involved in a neuronal/neurological disease or disorder, such as autism, autism-spectrum disorders, obsessive compulsive disorder (OCD), psychiatric disorders or diseases and; (c) treating the subject based on results from the testing of treatment(s) of step (b). The method can comprise delivering to cells of the transgenic non-human mammal the vector, and the transgenic non-human mammal is a transgenic mouse having cells that express Cas9, and the disease is genes involved in a neuronal/neurological disease or disorder, such as autism, autism-spectrum disorders, obsessive compulsive disorder (OCD), psychiatric disorders or diseases. The invention further envisions an individualized or personalized treatment of genes involved in abnormal neuronal/neurological development in a subject in need of such treatment comprising: (a) introducing multiple mutations ex vivo in a tissue, organ or a cell line comprising Cas9-expressing eukaryotic cell(s), or in vivo in a transgenic non-human mammal having cells that express Cas9, comprising delivering to cell(s) of the tissue, organ, cell or mammal the vector as herein-discussed, wherein the specific mutations or precise sequence substitutions are or have been correlated to genes involved in abnormal neuronal/neurological development; (b) testing treatment(s) for modifying genes involved in abnormal neuronal/neurological development on the cells to which the vector has been delivered that have the genes involved in abnormal neuronal/neurological development specific mutations or precise sequence substitutions correlated to genes involved in abnormal neuronal/neurological development and; (c) treating the subject based on results from the testing of treatment(s) of step (b). The method can comprise delivering to cells of the transgenic non-human mammal the vector, and the transgenic non-human mammal is a transgenic mouse having cells that express Cas9, and the disease is genes involved in abnormal neuronal/neurological development.

In another aspect, the present invention provides transgenic animals that are generated where at least one autism associated gene is mutated. The gene may be SHANKS, SAPAP3, MECP2, CHD8, DYRK1A, GRIN2B, KATNAL2, RIMS1, SCN2A, POGZ, ADNP, ARID1B, TBR1, NLRC5, STAC2, CRYBG3, SLC4A8, RAD54L2, MUC5B, MK167, POGZ, NEB, MYH9, TANC2, SCN2A, PIK3R3, ACO1, CAPN9, CTNNA2, GRIN2A, ASH1L, LRP1, STAG1, SYNGAP1 or any combination of genes is mutated. Preferably, CHD8 is mutated. A single allele may be mutated. Both alleles may be mutated. Preferably, the eukaryotic cell or transgenic animal is a heterozygote for an mutated gene. Preferably the mutation is a loss-of-function mutation. Preferably, the mutation generates a transgenic animal that is heterozygous for a loss-of-function mutation in CHD8. In one embodiment, the transgenic animal displays ASD behavioral phenotypes.

In another aspect, the present invention provides for vectors used to generate the transgenic animal of the present invention. The vectors can be of any described herein and comprise at least on guide RNA targeting the CHD8 gene. More than one guide RNA can target the gene. Any exon, splice site, promoter, regulatory element or intron may be targeted.

In another aspect, the present invention provides for a method of generating a transgenic animal that displays ASD behavioral phenotypes.

In another aspect, the present invention provides for a method of drug screening for therapeutic molecules or agents that alleviate symptoms of ASD. In one embodiment, the transgenic animal is a heterozygote with loss-of-function of at least CHD8. In one embodiment, the transgenic animal is treated with a drug candidate, molecule, or agent and changes in phenotype are observed. Wishing not to be bound by a theory, drug candidates are selected that alleviate symptoms.

In another aspect, the present invention provides for a method of selecting candidate drug targets. In one embodiment, at least one gene in addition to CHD8 is mutated in a transgenic animal and the phenotype is observed. Not being bound by a theory mutated genes that lead to enhanced ASD phenotypes may be potential drug targets for therapy.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C.

§ 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1A-E illustrates the production and characterization of transgenic mice heterozygous for the CHD8 gene. 1A illustrates the workflow for generating and characterizing germline edited mice. 1B illustrates the Chd8 targeting strategy and guide RNA design (SEQ ID NOS 29 and 30, respectively, in order of appearance). Also see FIG. 5. 1C illustrates the sequences of Chd8 edited alleles in mosaic founders (SEQ ID NOS 31-51, respectively, in order of appearance). Data represent all mutant alleles found within 38 animals from 6 recipient mothers. Bolded Chd8 allele with 7 nt deletion represents LOF mutation in established mouse line. 1D illustrates the classification and quantification of Chd8 targeted mosaic founder. Mice were classified as having zero (WT, n=27), one (monoallelic, n=3), two (biallelic, n=1), or >2 (multiallelic, n=7) mutant allele(s). Also see FIG. 5. 1E illustrates CHD8 protein expression in whole brain lysates from wild-type and Chd8$^{+/-}$ embryonic day 18 mice, showing approximately half the expression in heterozygous mutant mice. Each lane was loaded with 5 µg of protein with GAPDH as loading control.

FIG. 2A-I illustrates that Chd8$^{+/-}$ mice display ASD-like behaviors. 2A. In the social interaction test, Chd8$^{+/-}$ mice (blue dots, n=8) spent less time interacting with a social partner than an empty cup, compared to wild-type littermates (grey dots, n=9). 2B. In the social novelty test, Chd8$^{+/-}$ mice (n=8) spent less time interacting with a novel social partner than a familiar mouse, compared to wild-type littermates (n=8). 2C. Chd8$^{+/-}$ mice show (n=8), decreased preference for sociability (ratio of time interacting with a new mouse to total time from FIG. 2A) and social novelty (ratio of novel interaction time to total interaction time from FIG. 2B) compared to wild-type littermates (n=8). 2D. In the novel object recognition test, Chd8$^{+/-}$ mice (n=7) spent less time interacting with two novel objects during a habituation period compared to wild-type littermates (n=9). 2E. In the novel object recognition test, Chd8$^{+/-}$ mice (n=7) spent less time with a novel object compared to wild-type littermates (n=9). 2F. In the dark-light emergence test, Chd8$^{+/-}$ mice (n=10) and wild-type (n=12) littermates spent equal amounts of time in the light side of the arena. Also see FIG. 6. 2G. In the dark-light emergence test, Chd8$^{+/-}$ mice (n=10) spent more time in the dark side of the arena before crossing over to the light side of the arena compared to wild-type littermates (n=12). 2H. (Left) Open field traces for animals with median center time values. (Right) In the open field test, Chd8$^{+/-}$ mice (n=17) spent less time in the center compared to wild-type littermates (n=23). 2I. In the rotarod performance test, Chd8$^{+/-}$ mice (n=8) spent more time on the rotating rod before falling off compared to wild-type littermates (n=9). Three trials were performed per day for two days. Also see FIG. 6. Data are means±SEM; (A-I) two-tailed t-test and (J) two-way repeated measure ANOVA with post hoc two-tailed t-test. *p<0.05, p<0.01, *p<0.001.

FIG. 3A-G. illustrates phenotypes of Chd8$^{+/-}$ mice. 3A-B. illustrates that protein expression profiling shows NMDA receptor subunits NR2A and NR2B are increased in the (A) NAc but not the (B) DS of Chd8$^{+/-}$ mice (n=3) compared to wild-type littermates (n=3). Each lane was loaded with 5 µg of protein with GAPDH and ACTB as loading controls and normalized to wild-type levels. Also see FIG. 7. 3C. Representative sEPSC traces from MSNs in the core region of the NAc of Chd8$^{+/-}$ mice and wild-type littermates. 3D. sEPSC frequency increase in MSNs in the NAc of Chd8$^{+/-}$ mice compared to wild-type littermates. Data collected from Chd8$^{+/-}$ mice (n=28 cells from 3 mice) and wild-type littermates (n=24 cells from 3 mice). 3E. sEPSC amplitude increase in MSNs in the NAc of Chd8$^{+/-}$ mice compared to wild-type littermates. Data collected from Chd8$^{+/-}$ mice (n=28 cells from 3 mice) and wild-type littermates (n=24 cells from 3 mice). 3F. Representative MSN dendrites in the NAc of Chd8$^{+/-}$ mice and wild-type littermates. G. Spine density (number of spines per µm) in MSN dendrites in the NAc of Chd8$^{+/-}$ mice compared to wild-type littermates. Data collected from two animals for each Chd8$^{+/-}$ mice (n=26 cells) and wild-type littermates (n=25 cells). Data are means±SEM; two-tailed t-test. *p<0.05, **p<0.01.

DETAILED DESCRIPTION OF THE INVENTION

Figure 4A:
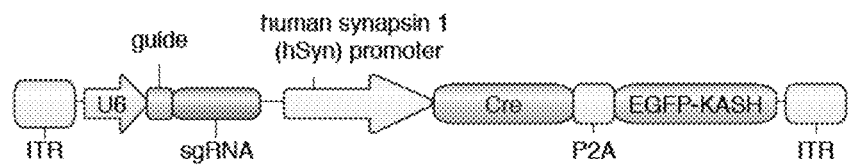
FIG. 4A-E. illustrates in vivo perturbation of Chd8 in adult mice recapitulates ASD-like behavior. 4A. Diagram of AAV vector for guide RNA expression, Cas9 induction, and nuclei labeling in neurons of the Cre-dependent Cas9 mice. 4B. Workflow for generating and characterizing somatically edited Cre-dependent Cas9 mice. 4C. (Left) Schematic representation of a brain slice with the nucleus accumbens (NAc) and dorsal striatum (DS) target regions indicated. (Right) Representative immunofluorescence images four weeks post-injection showing AAV infected, EGFP expressing neurons within the NAc and DS. Enclosed regions outline the targeted region. Also see FIG. 8 and FIG. 9. 4D. Indel analysis on Illumina sequencing reads from FACS sorted neuronal nuclei showing single cells with zero (wild-type, 10%), one (monoallelic, 57%), or two (biallelic, 33%) mutant alleles. 4E. In the rotarod performance test, AAV-sgChd8 NAc mice (n=15) spent more time on the rotating rod before falling off compared to AAV-sgChd8 DS (n=11) and AAV-sgLacZ NAc (n=15) control animals. Also see FIG. 9. Data are means±SEM; (D) two-way repeated measure ANOVA with post hoc two-tailed t-test were performed against AAV-sgChd8 NAc and AAV-sgLacZ NAc (grey asterisks) or AAV-sgChd8 NAc and AAV-sgChd8 DS (green asterisks). *p<0.05.
Figure 4B:
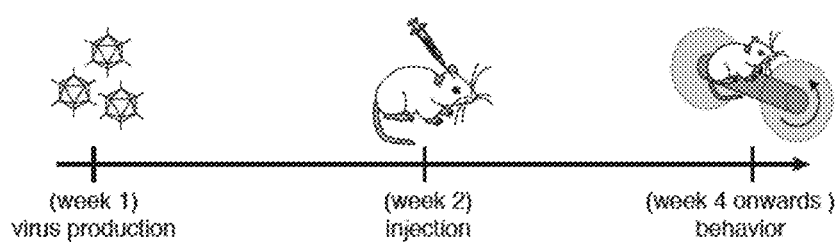
Figure 4C:
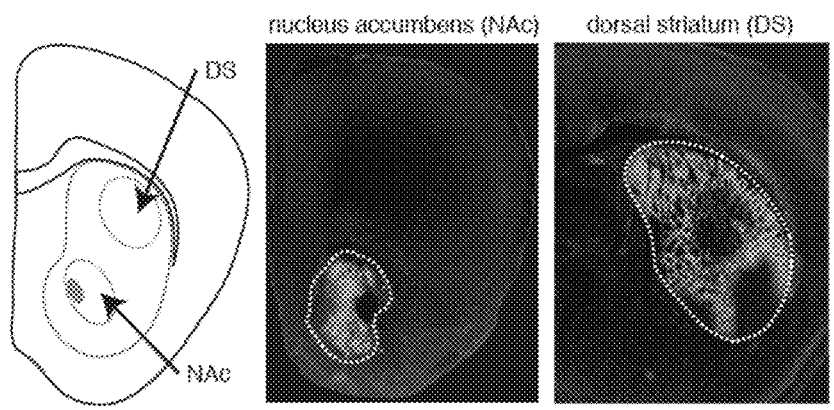

To facilitate an understanding of the present invention, a number of terms and phrases are defined herein:

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Unless specifically stated or obvious from context, as used herein, the term "or" is understood to be inclusive. Unless specifically stated or obvious from context, as used herein, the terms "a," "an," and "the" are understood to be singular or plural.

By "agent" is meant any small molecule chemical compound, antibody, nucleic acid molecule, or polypeptide, or fragments thereof.

As used herein, the terms "prevent," "preventing," "prevention," "prophylactic treatment," and the like, refer to reducing the probability of developing a disease or condition in a subject, who does not have, but is at risk of or susceptible to developing a disease or condition.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treat," "treated," "treating," "treatment," and the like are meant to refer to reducing or ameliorating a disorder and/or symptoms associated therewith (e.g., a neoplasia or tumor). "Treating" includes the concepts of "alleviating", which refers to lessening the frequency of occurrence or recurrence, or the severity, of any symptoms or other ill effects related to a disease, specifically ASD. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYS- TEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WIDE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR-Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546): 186-91 (2015).

Each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR-Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.source-forge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNN NNNNNNNNNN gttttttgtact ctcaagattt aGAAAtaaat cttgcagaag ctacaaagat aaggcttcat gccgaaatca acaccctgtc atttatggc agggtgtttt cgttatttaa TTTTTT (SEQ ID NO: 1); (2) NNNNNNNNNN NNNNNNNNNN gttttttgtac tctcaGAAAt gcagaagcta caaagataag gcttcatgcc gaaatcaaca ccctgtcatt ttatggcagg gtgttttcgt tatttaaTTT TTT (SEQ ID NO: 2); (3)

NNNNNNNNNN NNNNNNNNNN gttttgtac tctcaGAAAt gcagaagcta caaagataag gcttcatgcc gaaatcaaca ccctgtcatt ttatggcagg gtgtTTTTTT (SEQ ID NO: 3); (4) NNNNNNNNNN NNNNNNNNNN gttttagagc taGAAAtagc aagttaaaat aaggctagtc cgttatcaac ttgaaaagt ggcaccgagt cggtgcTTTT TT (SEQ ID NO: 4); (5) NNNNNNNNNN NNNNNNNNNN gttttagagc taGAAATAGc aagttaaaat aaggctagtc cgttatcaac ttgaaaaagt gTTTTTTT (SEQ ID NO: 5); and (6) NNNNNNNNNN NNNNNNNNNN gttttagagc tagAAATAGc aagttaaaat aaggctagtc cgttatcaTT TTTTTT (SEQ ID NO: 6). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 7) in the EMX1 gene of the human genome, deep sequencing can be used to assess the level of modification at the following two off-target loci, 1: 5'-GAGTCCTAGCAGGAGAAGAA-3' (SEQ ID NO: 8) and 2: 5'-GAGTCTAAGCAGAAGAAGAA-3' (SEQ ID NO: 9). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S. pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions. One can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/(visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO:

10); the NLS from nucleoplasmin (e.g. the nucleoplasmin bipartite NLS with the sequence KRPAATKKAGQAKKKK (SEQ ID NO: 11); the c-myc NLS having the amino acid sequence PAAKRVKLD (SEQ ID NO: 12) or RQRR-NELKRSP (SEQ ID NO: 13); the hRNPA1 M9 NLS having the sequence NQSSNFGPMKGGNFG-GRSSGPYGGGGQYFAKPRNQGGY (SEQ ID NO: 14); the sequence RMRIZFKNKGKDTAELRRRRVEVS-VELRKAKKDEQILKRRNV (SEQ ID NO: 15) of the IBB domain from importin-alpha; the sequences VSRKRPRP (SEQ ID NO: 16) and PPKKARED (SEQ ID NO: 17) of the myoma T protein; the sequence PQPKKKPL (SEQ ID NO: 18) of human p53; the sequence SALIKKKKKMAP (SEQ ID NO: 19) of mouse c-abl IV; the sequences DRLRR (SEQ ID NO: 20) and PKQKKRK (SEQ ID NO: 21) of the influenza virus NS1; the sequence RKLKKKIKKL (SEQ ID NO: 22) of the Hepatitis virus delta antigen; the sequence REKKKFLKRR (SEQ ID NO: 23) of the mouse Mx1 protein; the sequence KRKGDEVDGVDEVAKKKSKK (SEQ ID NO: 24) of the human poly(ADP-ribose) polymerase; and the sequence RKCLQAGMNLEARKTKK (SEQ ID NO: 25) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some aspects, the method may comprise one or more donor template(s), each of which may introduce one or more sequence alterations in one or more target genetic loci in the target cell, wherein the sequence alteration(s) are selected from the introduction of mutations and/or the repair to wild type, which upon expression thereby modulates the coding sequence or regulatory elements of one or more genes in the target cell. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

Transgenic non-human eukaryotic organisms, e.g., animals are also provided in an aspect of practice of the instant invention. Preferred examples include animals comprising Cas9, in terms of polynucleotides encoding Cas9 or the protein itself. In certain aspects, the invention involves a constitutive or conditional or inducible Cas9 non-human eukaryotic organism, such as an animal, e.g., a primate, rodent, e.g., mouse, rat and rabbit, are preferred; and can include a canine or dog, livestock (cow/bovine, sheep/ovine, goat or pig), fish, fowl or poultry, e.g., chicken, and an insect or arthropod, with it mentioned that it is advantageous if the animal is a model as to a human or animal genetic disease or condition, such as a neuronal/neurological disease or disorder, such as autism, autism-spectrum disorders, obsessive compulsive disorder (OCD), psychiatric disorders or diseases, as use of the non-human eukaryotic organisms in genetic disease or condition modeling, e.g., via inducing a plurality, e.g., 3 to 50 mutations correlated or associated with a genetic disease or condition, are preferred. To generate transgenic mice with the constructs, as exemplified herein one may inject pure, linear DNA into the pronucleus of a zygote from a pseudo pregnant female, e.g. a CB56 female. Founders may then be identified, genotyped, and backcrossed to CB57 mice. The constructs may then be cloned and optionally verified, for instance by Sanger sequencing. Knock-ins are envisaged (alone or in combination). Example 1 provides a knockin Cas9 mouse and to generate a Cas9 knock in mice one may target the same constitutive and conditional constructs to the Rosa26 locus, reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR-Cas system of the present invention. Methods of US Patent Publication No. 20130236946 assigned to Cellectis directed to targeting the Rosa locus may also be modified to utilize the CRISPR-Cas system of the present invention. In a particular embodiment Applicants disclose herein a novel in vivo CRISPR approach with a combination of novel Cas9 reagents, as well as demonstrate application in modeling the dynamics of mutations in genes involved in a neuronal/neurological disease or disorder, such as autism, autism-spectrum disorders, obsessive compulsive disorder (OCD), psychiatric disorders or diseases; and, that this system can be used to model three and even more than three genetic mutations, such as any number between three (3) and fifty (50) or more. And, this can include modeling in post-mitotic cells. In 293 cells the Cas9 conditional expression construct can be activated by co-expression with Cre. Correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. The conditional Cas9 mouse can be crossed with a mouse that ubiquitously expresses Cre (ACTB-Cre line) and may arrive at a mouse that expresses Cas9 in every cell. The delivery of RNA(s) to guide Cas9, e.g. CRISPR RNA and transactivating (tracr) RNA or a single guide RNA (sgRNA) (chimeric RNA) can induce genome editing in embryonic or adult mice. Interestingly, when the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue. Further, the conditional Cas9 mouse is broadly applicable for many areas of biology and its uses as described herein provide many utilities. More generally, while Cas9 provides an effective way to model multiple genetic lesions, Cas9 delivery has challenges, including limitations due to the significant size of Cas9, and possible extra biosafety practices. The Cas9 transgenic eukaryote, e.g., mouse provides a most effective method for genetic, e.g., neuronal/neurological disease or disorder modeling and other areas of tissue-specific biological studies. Applicants' approach provides a substantial packaging capacity for both sgRNAs as well as reporters and other modulators, etc. These features include efficient editing of cellular subtypes using Cre-driver lines, hard to transfect/transduce primary cells, and delivery of sgRNA using non-viral, nanotechnology-based methods. Applicants used lentivirus in their study disclosed herein in Examples 1 and 2. To demonstrate the significant utility of this transgenic eukaryote, e.g., animal, e.g., mammal, e.g., mouse line, Applicants used this conditional Cas9 transgenic eukaryote, e.g., animal, e.g., mammal, e.g., for direct genome editing in vivo of the brain in the Cre-dependent Cas9 mouse.

Mouse models are known for neurology models (see, e.g., Peca et al. 2011; Welch et al., 2007, Guy et al., 2001; discussed briefly below). For example, perspectives on neuronal development and pathology have emerged from the study of single and multiple gene-knockout animals, as well as from conditional knockout and 'knock-in' mutants. Analysis of these animals has clarified important intracellular signalling pathways and has shed light on the regulatory mechanisms that govern normal neuronal/neurological responses.

As used herein, the terms "neuronal," "neurological," "nervous system-related" are used interchangeably and intended to have the same meaning. With respect to diseases and/or disorders or conditions of neuronal/neurological/nervous-system related, the present invention relates to targeting genes and mutants thereof in, for example in, but not limited to, genes involved in, associated with or correlated with, autism, autism spectrum disorders (ASDs), psychiatric/neuropsychiatric diseases or disorders, obsessive compulsive disorders (OCD), Rett syndrome, schizophrenia, Huntington's disease, etc. In this regard, mention is made of the following exemplary publications which discuss certain aspects of such diseases or disorders, the text of each of which publication is incorporated herein in its entirety for all purposes.

Peça J. et al. Shank3 mutant mice display autistic-like behaviors and striatal dysfunction. *Nature* 2011 Apr. 28; 472(7344):437-42. doi: 10.1038/nature09965. Epub 2011 Mar. 20.

Welch J. M. et al. Cortico-striatal synaptic defects and OCD-like behaviors in Sapap3-mutant mice. Nature 2007 Aug. 23; 448(7156):894-900.

Guy J. et al. A mouse Mecp2-null mutation causes neurological symptoms that mimic Rett syndrome. Nature Genetics March 2001; 27: 322-326.

Pouladi M A et al. Choosing an animal model for the study of Huntington's disease. *Nat Rev Neurosci*. 2013 October; 14 (10):708-21. doi: 10.1038/nrn3570.

Ronemus M. et al. The role of de novo mutations in the genetics of autism spectrum disorders. *Nat. Rev. Genet.* 2014 February; 15(2):133-41. doi: 10.1038/nrg3585. Epub 2014 Jan. 16.

Fromer M. et al. De novo mutations in schizophrenia implicate synaptic networks. Nature 2014 Feb. 13; 506 (7487):179-84. doi: 10.1038/nature12929. Epub 2014 Jan. 22.

Van Rompay K. K. The use of nonhuman primate models of HIV infection for the evaluation of antiviral strategies. *AIDS Res Hum Retroviruses*. 2012 January; 28(1):16-35. doi: 10.1089/AID.2011.0234. Epub 2011 Oct. 19.

Peca et al. 2011, showed that mice with Shank3 gene deletions exhibit self-injurious repetitive grooming and deficits in social interaction. CHD8, DYRK1A, GRIN2B, KATNAL2, RIMS1, SCN2A, POGZ, ADNP, ARID1B, TBR1 is a postsynaptic protein, whose disruption at the genetic level is thought to be responsible for the development of 22q13 deletion syndrome (Phelan-McDermid syndrome) and other non-syndromic ASDs. Cellular, electrophysiological and biochemical analyses uncovered defects at striatal synapses and cortico-striatal circuits in Shank3 mutant mice. The authors' findings demonstrated a critical role for SHANK3 in the normal development of neuronal connectivity and established causality between a disruption in the Shank3 gene and the genesis of autistic-like behaviours in mice.

Welch et al. 2007, showed that mice with genetic deletion of Sapap3 exhibit increased anxiety and compulsive grooming behaviour leading to facial hair loss and skin lesions.

SAP90/PSD95-associated protein 3 (SAPAP3; also known as DLGAP3) is a postsynaptic scaffolding protein at excitatory synapses that is highly expressed in the striatum. Electrophysiological, structural and biochemical studies of Sapap3-mutant mice reveal defects in cortico-striatal synapses. Furthermore, the author showed that lentiviral-mediated selective expression of Sapap3 in the striatum rescued the synaptic and behavioural defects of Sapap3-mutant mice. The authors' findings demonstrated a critical role for SAPAP3 at cortico-striatal synapses and emphasized the importance of cortico-striatal circuitry in OCD-like behaviours.

Guy et al. 2001, generated mice lacking Mecp2 using Cre-loxP technology. The authors observed that both Mecp2-null mice and mice in which Mecp2 was deleted in brain showed severe neurological symptoms at approximately six weeks of age. Rett syndrome (RTT) is an inherited neurodevelopmental disorder of females that occurs once in 10,000-15,000 births. Affected females develop normally for 6-18 months, but then lose voluntary movements, including speech and hand skills. Most RTT patients are heterozygous for mutations in the X-linked gene MECP2, encoding a protein that binds to methylated sites in genomic DNA and facilitates gene silencing.

Ronemus et al. 2014, provide a review of the recent advances in identification of the genetic components of autism spectrum disorders (ASDs), particularly the demonstration of de novo mutations as an important source of causality. The authors review these developments in light of genetic models for ASDs. The authors consider the number of genetic loci that underlie ASDs and the relative contributions from different mutational classes, and discuss possible mechanisms by which these mutations might lead to dysfunction.

The present invention relates to targeting genes and mutants thereof involved in autism spectrum disorders, for example, but not limited to, genes with recurrent de novo loss-of-function mutations (such as CHD8, DYRK1A, GRIN2B, KATNAL2, RIMS1, SCN2A, POGZ, ADNP, ARID1B, TBR1) (see e.g., Ronemus et al. 2014).

Fromer et al. 2014, discuss insights into aetiological mechanisms for schizophrenia and reveal pathophysiology shared with other neurodevelopmental disorders. The authors showed that in schizophrenia, small de novo mutations, affecting one or a few nucleotides, are overrepresented among glutamatergic postsynaptic proteins comprising activity-regulated cytoskeleton-associated protein (ARC) and N-methyl-D-aspartate receptor (NMDAR) complexes. The authors further discuss that mutations are additionally enriched in proteins that interact with these complexes to modulate synaptic strength, namely proteins regulating actin filament dynamics and those whose messenger RNAs are targets of fragile X mental retardation protein (FMRP). Genes affected by mutations in schizophrenia overlap those mutated in autism and intellectual disability, as do mutation-enriched synaptic pathways.

Epilepsy, spina bifida, anencephaly, encephalocele and other developmental problems are associated with genetic defects, or certain genetic alleles or mutations have been associated with increased risk of such neuronal-related developmental issues. For instance, certain mutations in the gene VANGL1 are implicated as a risk factor for spina bifida in some families. See e.g., Kibar et al. (2007). "Mutations in VANGL1 associated with neural-tube defects" N. Engl. J. Med. 356 (14): 1432-7. Genetics is believed to be involved in the majority of epilepsy cases, either directly or indirectly. Some epilepsies are due to a single gene defect. Most others are due to the interaction of multiple genes and environmental factors. Genes discovered to be involved in human epilepsies include those that encode subunits of ion channels, both voltage-gated and ligand-gated, and in various enzymes, GABA, and G protein-coupled receptors. See, e.g., Berkovic S F I, Mulley J C, Scheffer I E, Petrou S (2006) Trends Neurosci 29 (7): 391-7. PMID 16769131; Pandolfo, M. (November 2011) Semin Neurol 31 (5): 506-18. doi:10.1055/s-0031-1299789. PMID 22266888.

The present invention relates to targeting genes and mutants thereof, in genes which overlap between neurological and psychiatric disorders, e.g., genes which overlap between schizophrenia, autism spectrum disorder and intellectual disability; for example, certain non-limiting exemplary genes include: NLRC5, STAC2, CRYBG3, SLC4A8, RAD54L2, MUC5B, MKI67, POGZ, NEB, MYH9, TANC2, SCN2A, PIK3R3, ACO1, CAPN9, CTNNA2, GRIN2A, ASH1L, LRP1, STAG1, SYNGAP1 (see e.g., Fromer et al. 2014).

Accordingly, the invention involves a non-human eukaryote, animal, mammal, primate, rodent, etc or cell thereof or tissue thereof that may be used as a disease model. As used herein, "disease" refers to a disease, disorder, or indication in a subject. For example, a method of the invention may be used to create a non-human eukaryote, e.g., an animal, mammal, primate, rodent or cell that comprises a modification, e.g., 3-50 modifications, in one or more nucleic acid sequences associated or correlated with a disease, e.g., a neuronal/neurological disease or disorder, such as autism, autism-spectrum disorders, obsessive compulsive disorder (OCD), psychiatric disorders or diseases of such. Such a mutated nucleic acid sequence be associated or correlated with a neuronal/neurological disease or disorder, such as autism, autism-spectrum disorders, obsessive compulsive disorder (OCD), psychiatric disorders or diseases and may encode a disease associated protein sequence or may be a disease associated or correlated control sequence. The cell may be in vivo or ex vivo in the cases of multicellular organisms. In the instance where the cell is in cultured, a cell line may be established if appropriate culturing conditions are met and preferably if the cell is suitably adapted for this purpose (for instance a stem cell). Hence, cell lines are also envisaged. In some methods, the disease model can be used to study the effects of mutations on the animal or cell and development and/or progression of the disease using measures commonly used in the study of the disease. Alternatively, such a disease model is useful for studying the effect of a putatively pharmaceutically active compound or gene therapy on the disease. A disease-associated gene or polynucleotide can be modified to give rise to the disease in the model, and then putatively pharmaceutically active compound and/or gene therapy can be administered so as to observe whether disease development and/or progression is inhibited or reduced. In particular, the method comprises modifying so as to produce, one or more, advantageously 3-50 or more disease-associated or correlated gene(s) or polynucleotide(s). Accordingly, in some methods, a genetically modified animal may be compared with an animal predisposed to development of the disease, such that administering putative gene therapy, or pharmaceutically acceptable compound(s), or any combination thereof can be performed to assess how such putative therapy(ies) or treatment(s) may perform in a human. The invention can involve contacting a test compound with a cell or administering to a eukaryote a test compound, wherein the eukaryote or cell comprises one or more, e.g., 3-50 or more mutations from the CRISPR-Cas system, e.g., in an animal that expresses Cas9 and to which RNA(s) generating the mutations has/have been administered; and detecting a reduction or an augmentation of a cell signaling event associated with the mutation(s) or lack thereof. Screening of such putative pharmaceutically active compound(s) and/or gene therapy(ies) can be by cellular function change and/or intracellular signaling or extracellular signaling change. Such screening can involve evaluating for dosages or dose curves, as well as combinations of potential drugs and/or therapies. An altered expression of one or more genome sequences associated with a signaling biochemical pathway can be determined by assaying for a difference in the mRNA levels of the corresponding genes between the disease model eukaryote or animal or cell or tissue thereof and a normal eukaryote, animal, tissue or cell, and to ascertain whether when the disease model is administered or contacted with a candidate chemical agent or gene therapy it reverts to or towards normal. An assay can be for mutation(s)-induced alteration in the level of mRNA transcripts or corresponding polynucleotides in comparison with such level(s) in a normal eukaryote or animal and whether such level(s) are placed towards or to normal when a therapy or treatment or agent is employed. Screening can also involve evaluating whether the multiple mutations give rise to fibers. Accordingly, the invention comprehends delivery of multiple RNA(s), e.g., sgRNA(s), e.g., 3-50 or more, e.g., 3, 16, 32, 48, 50 or more to the transgenic Cas9 eukaryote and thereafter screening cells, tissue, tumors or the eukaryote for fibers or formation of fibers (with it understood that "eukaryote" is as herein discussed to include animal, mammal, etc). Inducing multiple mutations also enables the skilled person to divine new combinations of mutations that give rise to abnormal neuronal/neurological development or to genetic disorders such as a neuronal/neurological disease or disorder, such as autism, autism-spectrum disorders, obsessive compulsive disorder (OCD), psychiatric disorders or diseases. The ability to induce multiple mutations that accelerate or change the rate of a neuronal/neurological disease or disorder, such as autism, autism-spectrum disorders, obsessive compulsive disorder (OCD), psychiatric disorders or diseases accordingly provides many advantages heretofore unknown in research and development of pharmaceuticals, therapies and treatments for such disorders.

The present invention encompasses treating a neuronal/neurological disease or disorder. Advantageously, the neuronal/neurological disease or disorders are autism, autism-spectrum disorders, obsessive compulsive disorder (OCD), and psychiatric disorders or diseases.

In an aspect the invention can involve cells, e.g., non-human eukaryotic, e.g., animal, such as mammal, e.g., primate, rodent, mouse, rat, rabbit, etc., or even human cells, transformed to contain Cas9, e.g., such cells as to which a vector that contains nucleic acid molecule(s) encoding a Cas9, e.g., with nucleic acid(s) encoding a promoter and at least one NLS, advantageously two or more NLSs, or such cells that have had their genome altered, e.g., through the vector being an integrating virus or through such cells being stem cells or cells that give rise to a cell line or a living organism (but wherein such an organism is advantageously non-human), that contains and expresses nucleic acid molecule(s) encoding Cas9. Such cells are then transplanted into or onto an animal suitable for being a model for probing the function or effects of genes involved in abnormal neuronal/neurological development or in a neuronal/neurological disease or disorder, such as autism, autism-spectrum disorders, obsessive compulsive disorder (OCD), psychiatric disorders or diseases, model, e.g., fish, a rodent such as a mouse, chickens or chicken embryo or chicken embryo membrane. The cells proliferate on or in the non-human eukaryote, e.g., animal model. The non-human eukaryote, e.g., animal model, having the proliferated heterologous transplanted Cas9-containing cells, is then administered RNA(s) or vector(s), e.g., AAV, adenovirus, lentivirus containing or providing RNA(s), e.g., under the control of a promoter such as a U6 promoter and/or particle(s) and/or nanoparticle(s) containing the RNA(s) and/or vector(s), whereby the RNA(s) direct the Cas9 in the cells to provide mutation, e.g., a plurality of mutation(s) such as from 3 to 50 mutations, advantageously mutation(s) associated or correlated with genes involved in abnormal neuronal/neurological development or in a neuronal/neurological disease or disorder, such as autism, autism-spectrum disorders, obsessive compulsive disorder (OCD), psychiatric disorders or diseases, whereby the non-human eukaryote, e.g., animal model is transformed into being a non-human eukaryote, e.g., animal model for a neuronal/neurological disease or disorder, such as autism, autism-spectrum disorders, obsessive compulsive disorder (OCD), psychiatric disorders or diseases. The non-human eukaryote, e.g., animal model can then be used for testing, e.g., as to potential therapy and/or putative treatment via a possibly pharmaceutically active compound. The administering can be at or to or for body delivery to the proliferated heterologous transplanted Cas9-containing cells, e.g., direct injection at or near such proliferated heterologous transplanted Cas9-containing cells, or injection or other administration in such a way that the RNA(s) are delivered into the proliferated heterologous transplanted Cas9-containing cells, e.g., injection into the bloodstream whereby bodily functions transport to the proliferated heterologous transplanted Cas9-containing cells. In an aspect of the invention, barcoding techniques of WO/2013/138585 A1 can be adapted or integrated into the practice of the invention. WO/2013/138585 A1 provides methods for simultaneously determining the effect of a test condition on viability or proliferation of each of a plurality of genetically heterogeneous cell types. The methods include: providing a unitary sample comprising a plurality of, e.g., five, ten, twenty, twenty-five, or more, genetically heterogeneous cell types (each individual cell type is genetically homogeneous within itself, but differs from the others in the plurality), wherein each cell type further comprises: (i) an exogenous nucleic acid tag stably integrated into the genome of the cells, e.g., a tag comprising a core sequence that is unique to each cell type, and flanking amplification primer binding sequences that are the same in all of the cells of the plurality, and (ii) optionally, a marker, e.g., a selectable or detectable marker; and a known number of cells of each cell type is present in the sample; exposing the sample to a test condition for a selected time; and detecting a level of the exogenous nucleic acid tag in each cell type, wherein the level of the exogenous nucleic acid tag is proportional to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type. WO/2013/138585 A1 also provides methods for simultaneously determining the effect of a test condition on viability or proliferation of each of a plurality of genetically heterogeneous cell types, wherein the methods include providing a unitary sample comprising a plurality of, e.g., five, ten, twenty, twenty-five, or more, genetically heterogeneous cell types, wherein each cell type further comprises: (i) an exogenous nucleic acid tag stably integrated into the genome of the cells, e.g., comprising a core sequence that is unique to each cell type, and flanking amplification primer binding sequences that are the same in all of the cells of the plurality, and (ii) optionally, a selectable or detectable marker; and a known number of cells of each cell type is present in the sample; implanting the sample into a living animal; exposing the sample to a test condition for a selected time; harvesting the sample from the animal; and detecting a level of the exogenous nucleic acid tag in each cell type of the sample, wherein the level of the exogenous nucleic acid tag correlates to the number of living cells in the sample after exposure to the test condition; and comparing the number of living cells in the sample after exposure to the test condition to a reference number of cells. The number of living cells in the sample after exposure to the test condition as compared to the reference number of cells indicates the effect of the test condition on viability or proliferation of each cell type. The tag can be Cas9 or another TAG or marker that is integrated into the genome of cells to be transplanted into or onto a non-human eukaryote, e.g., animal model, or that is integrated into the genome of the non-human transgenic eukaryote, e.g., animal, mammal, primate, rodent, mouse, rat, rabbit, etc (along with coding for Cas9). The test condition can be the administration or delivery of the RNA(s) to guide the Cas9 to induce one or more or a plurality, e.g., 3-50 or more, mutations. The test condition can be the administration, delivery or contacting with a putative chemical agent treatment and/or gene therapy treatment. The tag can also be the one or more or a plurality, e.g., 3-50 or more mutations, and the test condition can be the administration, delivery or contacting with a putative chemical agent treatment and/or gene therapy treatment.

The invention comprehends delivering the CRISPR-Cas system and/or component(s) thereof to the transgenic non-human eukaryote, e.g., mammal; for instance, to neuronal cells of a mammal, e.g., a non-human mammal. In general, delivery of the CRISPR-Cas system and/or component(s) thereof and/or coding for component(s) thereof can be as in WO 2014/093622 (PCT/US2013/074667), with AAV, lentivirus, and adenovirus vectors or particles or nanoparticles (including particle bombardment techniques that can include gold or other elemental, e.g., tungsten particles) preferred, and use thereof in the practice of the invention is within the ambit of the skilled artisan from this disclosure and the knowledge in the art, e.g., WO 2014/093622 (PCT/US2013/074667), incorporated herein by reference. The invention involves at least one component of the CRISPR complex, e.g., RNA, delivered via at least one vector or particle or nanoparticle complex. In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994). Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA. There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep. The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV. In addition to 293 cells, other cells that can be used in the practice of the invention and the relative infectivity of certain AAV serotypes in vitro as to these cells; see Grimm, D. et al, J. Virol. 82: 5887-5911 (2008) The invention provides rAAV that contains or consists essentially of an exogenous nucleic acid molecule encoding a CRISPR (Clustered Regularly Interspaced Short Palindromic Repeats) system or component(s) or coding therefor, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

If a Cas9-expressing model provided for herein is used, then only delivery of guide(s) is necessary. In some embodiments, one or more vectors described herein are used to produce a non-human transgenic Cas9 eukaryote, e.g., animal, mammal, primate, rodent, mouse, rat, rabbit. In some embodiments, the transgenic animal is a mammal, such as a mouse, rat, or rabbit. Guides or RNA(s) can be delivered via the same vector types as Cas9. When both guides or RNA(s) and Cas9 are being delivered a dual-vector system where the Cas9 is delivered via in vivo expression from an AAV vector and the guide(s) are delivered by a separate AAV vector. This can be done substantially contemporaneously (i.e.

co-delivery), but it could also be done at separate points in time, separated even by weeks or months. Of course, the ultimate separation is where the transgenic Cas9 eukaryote is generated and thereafter the guide(s) or RNA(s) are delivered. Alternatively a first round of CRISPR-Cas9 systems can be delivered, and subsequently further guides or RNA(s) are delivered as the original Cas9 is still functional in the target cells may be re-used. If the Cas9 is under the control of an inducible promoter, then induction of transcription of new Cas9 in the target cells is preferred.

Aerosolized delivery is preferred for AAV or adenovirus delivery in general. An adenovirus or an AAV particle may be used for delivery. Suitable gene constructs, each operably linked to one or more regulatory sequences, may be cloned into the delivery vector. In this instance, Cbh or EF1a promoter for Cas9, U6 or H1 promoter for chimeric guide RNA may be advantageous. Cas9 and/or RNA(s) can be delivered using particles, adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The vectors can be injected into the tissue of interest. For cell-type specific genome modification, the expression of Cas9 can be driven by a cell-type specific promoter.

Among vectors that may be used in the practice of the invention, integration in the host genome is possible with the retrovirus, lentivirus, and adeno-associated virus gene transfer methods, often resulting in long term expression of the inserted transgene. Additionally, high transduction efficiencies have been observed in many different cell types and target tissues. The tropism of a retrovirus can be altered by incorporating foreign envelope proteins, expanding the potential target population of target cells. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Zou et al. administered about 10 µl of a recombinant lentivirus having a titer of $1 \times 10^9$ transducing units (TU)/ml by an intrathecal catheter. These sorts of dosages can be adapted or extrapolated to use of a retroviral or lentiviral vector in the present invention.

Also useful in the practice of the invention is a minimal non-primate lentiviral vector, such as a lentiviral vector based on the equine infectious anemia virus (EIAV) (see, e.g., Balagaan, J Gene Med 2006; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Intracameral, subretinal, intraocular and intravitreal injections are all within the ambit of the instant invention (see, e.g., Balagaan, J Gene Med 2006; 8: 275-285, Published online 21 Nov. 2005 in Wiley InterScience (www.interscience.wiley.com). DOI: 10.1002/jgm.845). In this regard, mention is made of RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for practice of the present invention. Dosing of RetinoStat® (e.g., $1.1 \times 10^5$ transducing units per eye (TU/eye) in a total volume of 100 µl) can be applied or extrapolated from in practicing the present invention with a lentivirus.

The invention also can be practiced with an adenovirus vector, e.g., an E1-, partial E3-, E4-deleted adenoviral vector may be used in the practice of the invention. Such vectors are safe as twenty-eight patients with advanced neovascular age-related macular degeneration (AMD) were given a single intravitreous injection of an E1-, partial E3-, E4-deleted adenoviral vector expressing human pigment epithelium-derived factor (AdPEDF.11) (see, e.g., Campochiaro et al., Human Gene Therapy 17:167-176 (February 2006)); and previous adenovirus doses ranging from $10^6$ to $10^{9.5}$ particle units (PU) can be adapted to or employed in the practice of the instant invention (see, e.g., Campochiaro et al., Human Gene Therapy 17:167-176 (February 2006)). Adenoviral vector-mediated RNA transfer appears to be a viable approach for delivery of RNA(S). For adenoviral vector injections into a rat, $2 \times 10^9$ infectious particles were injected in 3 ml of normal saline solution (NSS). This can be adapted to or extrapolated from in the practice of the present invention. For siRNA, a rat was injected into the great saphenous vein with 12.5 µg of a siRNA and a primate was injected into the great saphenous vein with 750 µg of a siRNA. This can be adapted to or extrapolated from in the practice of the present invention.

Accordingly, the invention contemplates amongst vector(s) useful in the practice of the invention: viral vectors, including retroviral vectors, lentiviral vectors, adenovirus vectors, or AAV vectors.

Several types of particle and nanoparticle delivery systems and/or formulations are known to be useful in a diverse spectrum of biomedical applications; and particle and nanoparticle delivery systems in the practice of the instant invention can be as in WO 2014/093622 (PCT/US13/74667). In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm. As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm. Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semi-conducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants. Doses of about 5 mg/kg are contemplated, with single or multiple doses, depending on the target tissue. It is mentioned herein experiments involving mice involve 20 g mammals and that dosing can be scaled up to a 70 kg human. With regard to nanoparticles that can deliver RNA, see, e.g., Alabi et al., Proc Natl Acad Sci USA. 2013 Aug. 6; 110 (32):12881-6; Zhang et al., Adv Mater. 2013 Sep. 6; 25(33): 4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93. Lipid Nanoparticles, Spherical Nucleic Acid (SNA™) constructs, nanoplexes and other nanoparticles (particularly gold nanoparticles) are also contemplate as a means for delivery of CRISPR/Cas system or component(s) thereof or vector(s) to intended targets. Particles, nanoparticles, and the like and vectors are advantageous for delivering the RNA(s) of the CRISPR-Cas9 system and particles and nanoparticles and the like may be advantageous for delivery of vector containing nucleic acid(s) encoding or comprising RNA(s) of the invention. In certain instances, e.g., where Cas9 is constitutively or inducibly or conditionally expressed by an organism or cells thereof, it is useful to deliver the RNA(s) (also herein sometimes termed "guides") of the CRISPR-Cas9 system separately from the Cas9. It is considered as advantageous that the Cas9 may be delivered via a viral vector or be constitutively or inducibly or conditionally expressed and that guides specific to genomic targets are delivered separately. A recent publication, entitled "In vivo endothelial siRNA delivery using polymeric nanoparticles with low molecular weight" by James E. Dahlman and Carmen Barnes et al. Nature Nanotechnology (2014) published online 11 May 2014, doi:10.1038/nnano.2014.84, incorporated herein in its entirety, showed that polymeric nanoparticles made of low-molecular-weight polyamines and lipids can deliver siRNA to endothelial cells with high efficiency, thereby facilitating the simultaneous silencing of multiple endothelial genes in vivo. The authors reported that unlike lipid or lipid-like nanoparticles, the nanoparticle formulation they used (termed 7C1), differed from traditional lipid-based nanoparticle formulations because it can deliver siRNA to lung endothelial cells at low doses without substantially reducing gene expression in pulmonary immune cells, hepatocytes or peritoneal immune cells. Successful in vivo use of a nanoparticle formulation in the context of CRISPR-Cas to achieve functional gene silencing is possible with the 7C1 nanoparticle. The 7C1 nanoparticle can be formulated to mediate delivery of sgRNA to constitutively active Cas9 mouse. Synthesis of the 7C1 nanoparticle is described in Dahlman et al., 2014, Nature Nanotechnology.

Kits: In an aspect, the invention provides kits containing any one or more of the elements discussed herein. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow the provision of all elements of the systems of the invention. Kits can involve vector(s) and/or particle(s) and/or nanoparticle(s) containing or encoding RNA(s) for 3-50 or more mutations to be administered to a non-human transgenic Cas9 eukaryote, e.g., animal, mammal, primate, rodent, etc., with such a kit including instructions for administering to such a eukaryote; and such a kit can optionally include a transgenic Cas9 eukaryote, or when such a transgenic Cas9 eukaryote has Cas9 expression that is inducible or conditional, e.g., Cre-dependent, the kit may also include a mate that expresses the compound that induces or is the trigger or condition for Cas9 expression, e.g., Cre, either throughout all cells or in only certain cells or tissue, whereby offspring of the eukaryotes express of Cas9, e.g., in specific tissues or throughout most or all or nearly all cells, whereby the kit can include instructions for mating and then administering. The kit may include any of the components above (e.g. vector(s) and/or particle(s) and/or nanoparticle(s) containing or encoding RNA(s) for 3-50 or more mutations) as well as instructions for use with any of the models or methods of the present invention.

Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$, is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$., allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A.; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C | Aromatic Aliphatic | F W Y H I L V |
| Polar | W Y H K R E D C S T N Q | Charged Positively charged Negatively charged | H K R E D H K R E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 26). This may be followed by the loop sequence GAAA as shown. Both of these are preferred examples. Applicants have demonstrated Cas9-mediated indels at the human EMXI and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736, 465 and U.S. 61/721,283, which is hereby incorporated by reference in its entirety.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

In an aspect of the invention, Applicants provide a new method to investigate modules and factors applicable across diverse biological systems. In a further aspect of the invention, the methods provided are coupled with advances in single cell profiling that bridge the gap between genome-wide pooled screens and deep molecular readouts.

With respect to single cell genomic readouts, methods such as DROP-Seq may be employed. Drop-seq is a method which enables highly parallel analysis of individual cells by RNA-seq. Specifically, the RNA content of tens and hundreds of thousands of individual human cells are profiled quickly and inexpensively. In an embodiment of Drop-Seq, special microfluidic devices are used to encapsulate each cell in an individual drop, associate the RNA of each cell with a 'cell barcode' unique to that cell/drop, measure the expression level of each RNA with sequencing, and then use the cell barcodes to determine which cell each RNA molecule came from. (Macosko et al., 2015, Cell 161, 1202-1214)

Currently, techniques or instruments for single molecule or single cell analysis exist (e.g., digital polymerase chain reactions (PCR) or Fluidigm C1, respectively), however none currently allow a scalable method for dynamically delivering reagents and/or appending molecular "information" to individual reactions such that a large population of reactions/assays can be processed and analyzed en masse while still maintaining the ability to partition results by individual reactions/assays. It is an aspect of the present invention to provide a method to screen pathways and modules of interest in systems such as immune diseases coupled to current advances in DROP-Seq methodology.

In a further aspect, Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. (Klein et al., 2015, Cell 161, 1187-1201).

The present invention provides for the rapid generation of Chd8 loss-of-function (LOF) mice. The present invention provides advantages based on the novel discoveries that Chd8$^{+/-}$ mutant mice demonstrate hallmark autism-like behaviors. Additionally, loss-of-function Chd8 mutations cause synaptic dysfunction in the nucleus accumbens NAc and perturbation of Chd8 in the NAc of adult mice recapitulates ASD-like behavior. Thus, characterization of Chd8 LOF produced by genome engineering allows for novel animal models to use in drug target discovery and drug discovery. The animal model may be used as a tool that may be used to understand ASD.

To test the genotype-phenotype association between CHD8 mutations and ASD, Applicants advantageously used CRISPR-Cas9 to rapidly generate mice carrying Chd8 heterozygous loss-of-function (LOF) mutations, the predominant form found in ASD patients. Applicants characterized the behavior and brain function of these mice, focusing on traits relevant to ASD. Applicants found that Chd8$^{+/-}$ mice display ASD-like behavior as well as synaptic, morphological, and biochemical deficits within a certain cell type and brain region, thus supporting the notion that CHD8 is a bona fide risk allele. Moreover, the results, together with previously published studies, support the hypothesis of a convergent molecular mechanism of ASD involving striatal dysfunction (Peca et al., 2011; Penagarikano et al., 2011; Rothwell et al., 2014; Schmeisser et al., 2012; Won et al., 2012).

EXAMPLES

Although the present invention and its advantages have been described in detail, it should be understood that various changes, substitutions and alterations can be made herein without departing from the spirit and scope of the invention as defined in the appended claims.

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: A Cre-Dependent CRISPR-Cas9 Knockin Transgenic Mouse for Efficient Ex Vivo and In Vivo Genome Editing Reference is made to WO 2014/093622 (PCT/US13/74667), incorporated herein by reference.

CRISPR-Cas9 is a powerful technology for genome editing and is being widely adopted due to its efficiency and versatility. While Cas9-mediated genome editing applications are compelling, applying them in vivo and ex vivo is challenging, since commonly used delivery systems are inefficient and limit accessible cell types. To broaden the application of Cas9 Applicants established a Cre-dependent, Rosa26 *Streptococcus pyogenes* Cas9 knockin mouse and demonstrate its utility in diverse applications, which include gene editing in vivo in the brain by AAV-mediated delivery of an sgRNA expression cassettes and in vivo in endothelial cells by nanoparticle-mediated sgRNA delivery. Applicants also demonstrate efficient editing of key regulators ex vivo in hard to transfect/transduce primary immune cells resulting in an altered immune response. The ability to efficiently edit genes in diverse experimental systems ex vivo and in vivo in the conditional Cas9 mouse can be a valuable resource for many areas of biology.

A major potential benefit of genome engineering is the ability to directly perturb gene function in vivo or in primary cells ex vivo (Xue, W. et al. Nature advance on, (2014); Yin, H. et al. Nat. Biotechnol. 32, 551-3 (2014); Heckl, D. et al. Nat. Biotechnol. advance on, (2014)). However, before genetically perturbed cells can be investigated in many cell types in vivo or in primary cells ex vivo genome modifications must first be made in the germline, which can then be used to create a stable transgenic strain for experimentation. This process is time consuming and technically challenging, which increases exponentially as the number and complexity of genome modifications increases. Zinc finger nuclease (ZFN) and transcription activator-like effector nuclease (TALEN)-mediated genome engineering, mainly by viral-mediated delivery, have been used successfully to edit genes in vivo and ex vivo and are even being applied therapeutically (Perez, E. E. et al. Nat. Biotechnol. 26, 808-16 (2008); Miller, J. C. et al. Nat. Biotechnol. 29, 143-8 (2011)). However, these technologies are mostly inefficient and require the generation and validation of entirely new protein constructs for each desired target.

More recently the CRISPR (clustered regularly interspaced short palindromic repeat)-associated endonuclease Cas9 from *Streptococcus pyogenes* (SpCas9, abbreviated as Cas9 throughout this paper) has been applied for editing mammalian genomes by efficiently facilitating DNA double strand breaks (DSBs) (Cong, L. et al. Science (2013); doi:10.1126/science.1231143; Mali, P. et al. Science 339, 823-6 (2013)). Targeted DSBs provide an effective means for knocking out genes via non-homologous end joining (NHEJ)-mediated repair and for stimulating homologous recombination through homology directed repair (HDR) in the presence of a repair template. The Cas9 endonuclease is targeted to specific sequences by either a pair of crRNA and tracrRNA or a single guide RNA (sgRNA) (Deltcheva, E. et al. Nature 471, 602-7 (2011); Jinek, M. et al. Science 337, 816-21 (2012); Gasiunas, G. et al. Proc. Natl. Acad. Sci. U.S.A. 109, E2579-86 (2012)). A significant advantage of Cas9 over ZFNs and TALENs is that targeting a new sequence only requires designing an sgRNA and not a new protein. Moreover, Cas9 can be combined with multiple sgRNAs to perturb multiple genes simultaneously (Cong, L. et al. Science (2013); doi:10.1126/science.1231143; Mali, P. et al. Science 339, 823-6 (2013); Xiao, A. et al. Nucleic Acids Res. 41, e141 (2013)) or with a library of sgRNAs for functional genomic screens (Shalem, O. et al. Science 343, 84-7 (2014); Sanjana, N. E. et al. Nat. Methods 11, 783-784 (2014)).

While Cas9-mediated genome editing applications are compelling, applying them in vivo and ex vivo is challenging, mainly due to its large transgene size (4.1 kb). Commonly used delivery systems, such as viral vectors, have strict packaging limits and therefore as transgene size increases the available options for delivery decreases (Kumar, M. et al. Hum. Gene Ther. 12, 1893-905 (2001)). Moreover, as transgene size increases the ability to generate high titer virus, which is essential for efficiently transducing cells in vivo and ex vivo, is also significantly reduced (Kumar, M. et al. Hum. Gene Ther. 12, 1893-905 (2001)). Consequently, Cas9-containing viral vectors have a limited capacity for including additional genetic elements (i.e. sgRNAs, homologous recombination donor templates, fluorescent proteins, modulators, etc.) in a single vector and suffer from low titer, which together limit the flexibility of gene editing in a range of cell types.

To facilitate the broader application of Cas9, Applicants generated a Cre-dependent Rosa26 3×FLAG tagged Cas9-P2A-EGFP knockin transgenic mouse, which removes the significant Cas9 delivery burden and only requires the delivery of Cre and an sgRNA to achieve gene editing. However, a significant concern was that Cas9 expression, once induced, may cause toxicity due to non-specific nuclease activity. Therefore, as a broad way to test this Applicants generated a sub strain with constitutive Cas9 expression in all cells by crossing the Cre-dependent Cas9 mouse with a beta-actin Cre-driver strain (Lewandoski, M. et al. Cold Spring Harb. Symp. Quant. Biol. 62, 159-68 (1997)). Resulting progenies of this cross were viable and Cas9 expression was observed at the whole-organ-level as well as the protein-level in whole-brain lysates. This was not observed in the Cre-dependent Cas9 mice or wild-type controls. Additionally, the constitutively Cas9 expressing animals were fertile, had normal litter sizes, presented no morphological abnormalities, and could be bred to homozygosity. At the cellular-level Applicants also found no morphological abnormalities or upregulation in DNA damage and apoptosis markers. Taken together these data suggest that Cas9 expression is tightly controlled in Cre-dependent Cas9 mice, and constitutive expression can be maintained without causing detectible toxicity using several metrics.

To determine whether the Cas9 transgene within the genome was functional Applicants tested whether adeno-associated virus (AAV)-mediated delivery of HA-tagged Cre and sgRNA could mediate indel formation in the brain in vivo. Applicants constructed an AAV-U6-sgRNA-Cre vector (AAV-sgRNA) containing an sgRNA targeted to a highly expressed neuronal-specific RNA-splicing factor, NeuN (sgNeuN) and packaged the vector using AAV serotypes 1 and 2 (AAV1/2), for delivery by stereotactic injection into the prefrontal cortex of Cre-dependent Cas9 mice. Three weeks post injection Applicants acutely dissected the injected brain region and used the tissue for downstream assays. Deep sequencing of the NeuN locus showed indel formation near the predicted cleavage site; Cas9 was functional and facilitating DSBs. Furthermore, in these same samples Applicants observed NeuN protein depleted only in the injected region and not in controls (non-injected and LacZ-targeted sgRNA, termed sgLacZ). To quantify this effect Applicants performed immunoblots and deep sequencing on tissue from three mice and found that NeuN protein expression was reduced by nearly 80%, whereas indels were found at the target site in 85% of sequencing reads.

While immunoblot and whole-tissue indel analysis provides a global view of genome editing by Cas9, it does not capture the degree of modification at the single-cell-level. For example, without isolating single cells Applicants cannot identify whether one or both alleles are being edited within individual cells, which is important for understanding the genetic heterogeneity of this strategy. However, due to their complex morphology, isolation of individual intact neurons within the brain is challenging. To overcome this and facilitate single-cell genetic analysis Applicants set out to isolate individual neuronal nuclei, which has been shown previously (Okada, S. et al. J. Cell. Physiol. 226, 552-8 (2011)). Cytosolic expression of EGFP, originating from the Cas9-P2A-EGFP transgene, for isolating individual nuclei was insufficient so Applicants generated a single vector (AAV-sgRNA-hSyn-Cre-P2A-EGFP-KASH) and expressed sgRNA, Cre, and EGFP fused to the KASH (Klarsicht, ANC-1, Syne Homology) nuclear transmembrane domain. For downstream analysis Applicants used fluorescence activated cell sorting (FACS) to isolate single EGFP positive nuclei. Sequencing of 167 single nuclei showed that 84% (n=141) of transduced cells have both alleles edited (homozygous), while only 9% (n=15) of nuclei had single allele modification and 7% (n=11) remained unmodified. Of the 15 heterozygous nuclei all of the modified alleles contained missense (mis) mutations, whereas 141 homozygous nuclei contained both missense (mis) and sense (sen) mutations.

Viral-mediated expression of Cas9 is efficient for targeting heterogeneous cells within an injected tissue and is useful for a range of applications. However, a large diversity of cellular subtypes play fundamental roles in biological processes and need to be perturbed individually, which often cannot be done using viral-vectors. While tissue- and cell type-specific promoters for heterologous expression do exist they are often large or not tightly controlled, leading to reduced specificity (Lewandoski, M. et al. Cold Spring Harb. Symp. Quant. Biol. 62, 159-68 (1997)). A powerful way to achieve tissue- or cell type-specific expression is through the use of Cre-driver strains. Combining Cre-dependent Cas9 mice with the wide variety of available Cre-driver strains would provide a powerful means to achieve Cas9 expression in specific cell types and subsequent genome editing in these cells in vivo. Therefore, Applicants crossed the Cre-dependent Cas9 mouse with two Cre-driver strains to determine if Applicants could achieve neuronal subtype-specific Cas9 expression, namely the tyrosine hydroxylase (TH-IRES-Cre) driver for dopaminergic neurons and the parvalbumin (PV-Cre) driver for a subtype of inhibitory interneurons. As predicted, Cas9 expression was restricted to TH or PV positive cells.

While the morphology of Cas9 expressing neurons were no different than wild-type controls, neurons are particularly sensitive to transgene expression and thus may have abnormal physiological properties. Therefore, to ensure that constitutive Cas9 expression does not adversely affect cellular health and physiology Applicants used a panel of electrophysiological measurements to check the basal function of Cas9 expressing neurons. Applicants performed whole-cell patch clamp recordings in CA1 pyramidal neurons from acute hippocampal slices to examine firing threshold and rheobase current and found no significant changes between control and constitutively Cas9 expressing mice. In addition, there was no significant change in input resistance whole cell capacitance or membrane resting potential. Taken together these data suggest that fundamental properties of neurons, a particularly sensitive cell type, are not altered by the heterologous expression of Cas9.

Cell type-specificity achieved through the use of a Cre-driver is valuable but only possible when a cell type-specific promoter has been identified. Indeed, without a specific promoter genetic perturbation in specific cells is challenging. Therefore, to determine if Applicants could achieve cell type specificity without performing a genetic cross or viral delivery Applicants set out to test whether Applicants could combine constitutively expressing Cas9 mice with other targeting methods for in vivo sgRNA delivery.

In this Example, Applicants introduce Cre-dependent and constitutively Cas9 expressing mice, which further the reach of Cas9-mediated genome editing to include specific cell types in vivo and ex vivo. Applicants have demonstrated that Cas9 mice can be used to modify genes in the brain and restrict Cas9 expression to cellular subtypes. Each of these applications broadens the utility of Cas9 and address significant challenges facing its in vivo and ex vivo application. The flexibility for inducing Cas9 expression and delivering sgRNAs was demonstrated using a wide variety of targeting methods including AAV and lentiviral transduction, nanoparticle-mediated delivery, and genetic crosses with Cre-driver lines. The example applications demonstrated here enable a broader spectrum of biological experiments involving these Cas9 transgenic mouse lines.

Ethics Statement. All experimental protocols were approved by the CAC (Committee on Animal Care) of MIT and were in compliance with the Guidelines for the Care and Use of Laboratory Animals (Eighth edition, National Research Council of the National Academies).

Generation of the Cre-dependent Cas9 mouse. Cre-dependent Cas9 knockin mice were generated by homologous recombination in R1 embryonic stem cells and implanted in C57BL6/J blastocysts using standard procedures as described previously Heyer, M. P. et al. in Genomics 211-248 (John Wiley & Sons, Ltd, 2010); doi:10.1002/9780470711675.ch10. Briefly, a codon optimized 3xFLAG-NLS-SpCas9-NLS-P2A-EGFP expression cassette was cloned into the Ai9 Roas26 targeting vector Madisen, L. et al. Nat. Neurosci. 13, 133-40 (2010) and further verified by sequencing. Linearized targeting vector was electroporated into R1 embryonic stem cells followed by G418 and DTA selection for a week. Targeted single ES cell colonies were screened by PCR with primers amplifying both recombinant arms. PCR products were sequenced to further validate correct insertion. Correctly targeted colonies were injected into C57BL6/J blastocysts for generating chimeric mice. High percentage male chimeric mice were mated with C57 BL6/J female mice (Jackson laboratory) to establish germ-line-transmitted founders. Genotypes of Cas9 mice were determined by amplifying a 4.5 kb product from purified mouse tail DNA (Forward primer: GCAGCCTCTGTTC-CACATACAC (SEQ ID NO: 27); Reverse primer: ACCAT-TCTCAGTGGCTCAACAA (SEQ ID NO: 28)).

DNA vectors and sgRNA design. The AAV vectors used for stereotaxic injection into the mouse brain were cloned between AAV serotype 2 ITRs and also included the human U6 promoter for noncoding sgRNA transcription, the ubiquitous Cbh promoter, HA-tagged Cre recombinase for recombination of loxP-SV40polyA-LoxP, WPRE, and human growth hormone polyA sequence. For nuclei sorting a similar plasmid was cloned between AAV serotype 2 ITRs and also included the human U6 promoter for noncoding sgRNA transcription, the ubiquitous hSyn promoter, HA-tagged Cre recombinase for recombination of loxP-SV40polyA-LoxP, P2A, EGFP-KASH fusion for nuclei labeling, WPRE, and human growth hormone polyA sequence. SgRNAs were designed using the CRISPRtool (crispr.mit.edu) to minimize potential off-target effects. SgRNAs were validated in vitro by transient cotransfected (Lipofectamine 2000, Life Technologies) into the N2a mouse cell line with a plasmid constitutively expressing Cas9. Genomic DNA was harvested 72 hours post transfection.

AAV1/2 production. HEK293FT cells were transfected with the plasmid of interest, pAAV1 plasmid, pAAV2 plasmid, helper plasmid pDF6, and PEI Max (Polysciences, Inc. 24765-2) in Dulbecco's Modified Eagle Medium (DMEM from Life Technologies, 10569-010). 72 hours post transfection, the cell culture media was discarded. Then the cells were rinsed and pelleted via low speed centrifugation. Afterwards, the viruses were applied to HiTrap heparin columns (GE Biosciences 17-0406-01) and washed with a series of salt solutions with increasing molarities. During the final stages, the eluates from the heparin columns were concentrated using Amicon ultra-15 centrifugal filter units (Millipore UFC910024). Titering of viral particles was executed by quantitative PCR using custom Cre-targeted Taqman probes (Life Technologies).

Stereotactic injection of AAV. Before beginning surgery, pre-operative, operation, and post-operative areas were defined. Applicants ensured that all tools had been autoclaved and that reagents were sterile. Applicants administered a mixture of ketamine (100 mg/kg) and xylazine (10 mg/kg) intraperitoneally for anesthesia. Anesthesia levels were monitored by absence of corneal reflex, absence of foot withdrawal following pressure to the footpad, and by absence of startle from tail pinch. Applicants also administered buprenorphine HCl (0.1 mg/kg) intraperitoneally as a pre-emptive analgesic.

Once subject mice were in deep anesthesia, they were immobilized in a Kopf stereotaxic apparatus using intra-aural positioning studs and a tooth bar to immobilize the skull. Heat is provided for warmth by a standard heating pad. Then Applicants proceeded with the approved craniotomy procedures. Applicants drilled a hole on the surface of the skull at 1.94 mm anterior to Bregma and 0.39 mm lateral for injection into the prefrontal cortex. Using a 33 G Nanofil needle and World Precision Instrument Nanofil syringe at a depth of −2.95 mm, Applicants injected 1 uL AAV into the right hemisphere of the brain. Injection rates were monitored by the World Precision Instruments UltraMicroPump3. After injection, Applicants closed the incision site with 6-0 Ethilon sutures (Ethicon by Johnson & Johnson). Animal were postoperatively hydrated with 1 mL lactated Ringer's solution (subcutaneous) and housed in a temperature controlled (37° C.) environment until achieving ambulatory recovery. To relieve post-operative pain, Meloxicam (1-2 mg/kg) was also administered subcutaneously directly after surgery.

Electrophysiology. Data acquisition and analysis were performed with experimenter blinded to mice genotype as described in previous report (Han, K. et al. Nature 503, 72-7 (2013); Pep, J. et al. (2011) Nature, 472(7344), 437-42). Slices were prepared from 8-10 week old littermate-paired adult wild-type and homozygous constitutively Cas9 expressing mice. Mice were deeply anesthetized by intraperitoneal injection of avertin (1.25%, v/v) and transcardially perfused with carbogenated (95% O2, 5% CO2) ice-cold cutting solution that contained (in mM): 30 NaCl, 194 sucrose, 4.5 KCl, 10 glucose, 26 $NaHCO_3$, 1.2 $NaH_2PO_4$, 0.2 $CaCl_2$) and 8 $MgCl_2$. Acute coronal brain slices containing typical CA1 layer of media hippocampus were sliced using vibratome (leica VT 1200S) in a chamber filled with ice-cold sucrose based cutting solution. 300 μm slices were cut in sucrose cutting solution and then transferred to recovery chamber at 32° C. for 12 minutes in ACSF. The ACSF contained (in mM): 119 NaCl, 2.3 KCl, 11 glucose, 26.2 $NaHCO_3$, 1 $NaH_2PO_4$, 2.5 $CaCl_2$) and 1.3 $MgSO_4$. After recovery, slices were transferred to ACSF at room temperature (25° C.) for a least 1 hour before recording. Whole-cell recordings of CA1 pyramidal neurons were made under a DIC upright microscope (BX51WI, Olympus, Japan) using MultiClamp 700A amplifier (Molecular Device, USA). Recording electrodes with resistance of 3-4 MΩ were pulled from glass capillary (King Precision Glass, glass type 8250) using Flaming/Brown micropipette puller (model P-97, Sutter Instrument, USA), and filled with internal solution containing (in mM): 131 K-gluconate, 17.5 KCl, 1 $MgCl_2$, 1.1 EGTA, 10 HEPES, 9 NaCl, 2 ATP, 0.2 GTP, 10 phosphocreatine at pH 7.2 and osmolarity 280-290 mOsm/L. Series resistance typically ranging between 10~20 MΩ, was monitored and not compensated during the recording. Signals were sampled at frequencies of 10K Hz and filtered at 2K Hz using pClamp software (Clampex 10.2, Molecular Device) via a Digidata-1440A interface (Molecular Device). Data were presented as mean±S.E.M. Statistical significance was tested using unpaired two-tailed Student's t-test.

Genomic DNA extraction, captured sequencing, and indel analysis. Genomic DNA was extracted from both cells and tissue using Quick Extract DNA extraction solution (Epicentre) following the recommended protocol. Treated cells and tissues were used as a template for PCR for both captured sequencing and SURVEYOR nuclease assay using high fidelity polymerases (Thermo Scientific) as has been previously described (Hsu, P. D. et al. Nat. Biotechnol. 31, 827-32 (2013)). Low cycle, first round PCR was performed to amplify the target site. Second round PCR was performed to add generic adapters, which were then used for a third round of PCR for sample barcoding. Samples were pooled in equal amounts and purified using QiaQuick PCR Cleanup (Qiagen), quantified using Qubit (Life Technologies) and sequenced on a MiSeq (Illumina). Indel analysis was performed using custom scripts as previously described Hsu, P. D. et al. Nat. Biotechnol. 31, 827-32 (2013). Data were presented as mean±S.E.M. Statistical significance was tested using unpaired two-tailed Student's t-test.

SURVEYOR nuclease assay. PCR amplicons of target sites were purified and used as an input to the SURVEYOR nuclease assay (Transgenomics). The manufacturer's recommended protocol was followed. SURVEYOR nuclease assay-treated products were run on a 4-12% PA-TBE gel (Life Technologies), stained with Sybr Gold (Life Technologies) and imaged on a gel imager (Bio-Rad). Indel percent was quantified using relative band intensities.

Western blot analysis. Protein lysates were quantified using the BCA Protein Assay Kit (Pierce) and equally loaded onto a 4-20% Tris-HCL Criterion Gel (Bio-Rad). Proteins were transferred onto PVDF membrane (Bio-Rad), blocked solution (5% BLOT-QuickBlocker (G-Biosciences) in TBS-T (trisp buffered saline with 0.1% Tween-20)) and stained overnight at 4° C. on an orbital shaker using the following primary antibodies: anti-FLAG (1:1000, Sigma Aldrich, F1804), HRP conjugated anti-Gapdh (1:5000, Cell Signaling Technology, 3683), anti-beta-tubulin (1:1000, Cell Signaling Technology, 2128), and anti-HA (1:1000, Cell Signaling Technology, 3724 and 2367). Membranes were washed three times with TBS-T and stained with secondary antibodies for 1 hour at room temperature. Applicants used HRP-conjugated secondary antibodies (1:10000, Cell Signaling Technology, 7074 and 7076). Stained membranes were washed three times in TBS-T and then developed using SuperSignal West Femto Substrate (Pierce) and imaged on a gel imager (Bio-Rad).

Immunostaining and imaging. Mice were given a lethal dose of Ketamine/Xylazine in preparation for brain tissue collection. Mice were transcardially perfused with 0.9% saline followed by 4% paraformaldehyde using a peristaltic pump (Gilson). The collected brain tissue was fixed overnight and transferred to phosphate buffered saline the following day. Tissue sectioning was performed on a vibratome (Leica VT1000S) at a thickness of 40 μm. Sections were rinsed three times in phosphate buffered saline (PBS) with 0.1% Triton X-100 (PBS-Tx). Sections were blocked with 5% normal goat serum (NGS) (Cell Signaling Technology) in PBS-Tx for one hour. Sections were incubated with primary antibodies diluted in PBS-Tx with 5% NGS overnight at 4° C. on an orbital shaker. The following is a list of primary antibodies that were utilized: anti-cleaved caspase 3 (CC3) (1:1000, Cell Signaling Technology, 9664), anti-γH2AX (1:1000, Millipore, 05-636) anti-NeuN (1:800, Cell Signaling Technology, 12943), anti-GFP (1:1600, Nacalai Tesque, GF090R), anti-parvalbumin (1:1000, Sigma Aldrich, P3088) and anti-tyrosine hydroxylase (1:1000, Immunostar, 22941). The following day, sections are washed three times in PBS-Tx. The sections are then incubated in PBS-Tx with the appropriate AlexaFluor®405, 488, 568 and/or 647 secondary antibody (1:400, Life Technologies) for three hours at room temperature on an orbital shaker. After the incubation, sections are rinsed with PBS-Tx three times and then mounted onto superfrost microscope slides (VWR). The sections are then coverslipped with VECTASHIELD HardSet Mounting Medium with DAPI (VECTOR Laboratories) and visualized under a confocal microscope (Zeiss LSM 710, Ax10 ImagerZ2, Zen 2012 Software).

Purification and FACS of single neuronal nuclei. For labeling neuronal nuclei Applicants generated an AAV-U6-sgRNA-hSyn-Cre-P2A-EGFP-KASH vector. Three weeks post-injection Applicants performed acute dissection of the injection site in the prefrontal cortex. Tissue was gently homogenized in 2 ml ice-cold homogenization buffer (HB) (320 mM Sucrose, 5 mM CaCl, 3 mM $Mg(Ac)_2$, 10 mM Tris pH7.8, 0.1 mM EDTA, 0.1% NP40, 0.1 mM PMSF, 1 mM beta-mercaptoethanol) using 2 ml Dounce homogenizer (Sigma Aldrich); 25 times with pestle A, followed by 25 times with pestle B. An additional 3 ml of HB was added and the mixture was put on ice for 5 min. Gradient centrifugation was performed using 5 ml 50% OptiPrep™ density gradient medium (Sigma Aldrich) containing 5 mM CaCl, 3 mM Mg(Ac)$_2$, 10 mM Tris pH 7.8, 0.1 mM PMSF, 1 mM beta-mercaptoethanol. The nuclei-containing mixture was gently added on the top of a 29% iso-osmolar OptiPrep solution in a conical 30 ml centrifuge tube (Beckman Coulter, SW28 rotor). Samples were centrifuged at 10100×g (7,500 rpm) for 30 min at 4° C. The supernatant was removed and the nuclei pellet was gently resuspended in 65 mM beta-glycerophosphate (pH 7), 2 mM MgCl$_2$, 25 mM KCl, 340 mM sucrose and 5% glycerol. Intact nuclei were labeled with Vybrant DyeCycle™ Ruby Stain (Life Technologies) and sorted using a BD FACSAria III. EGFP$^+$ nuclei were sorted into individual wells of a 96 well-plate containing 5 µl of QuickExtract DNA Extraction Solution (Epicentre).

Nanostring nCounter expression measurement. DCs were processed and analyzed as previously described (Amit, I. et al. Science 326, 257-63. Briefly, 5×10$^4$ cells were lysed in TCL buffer (Qiagen) supplemented with β-mercaptoethanol. 5% of the lysate was hybridized for 16 hours with a previously described Nanostring Gene Expression CodeSet (Geiss, G. K. et al. Nat. Biotechnol. 26, 317-25 (2008)) and loaded into the nCounter Prep Station followed by quantification using the nCounter Digital Analyzer. Counts were normalized using control genes as previously described Amit, I. et al. Science 326, 257-63 (2009) and fold changes were calculated relative to cells transduced with sgRNA targeting GFP and non-targeted controls. Heat maps were created using GENE-E (www.broadinstitute.org/cancer/software/GENE-E/).

Example 2: Animal Models

Transgenic animals are also provided. Preferred examples include animals comprising Cas9, in terms of polynucleotides encoding Cas9 or the protein itself. Dogs, mice, pigs, rats, rabbits, sheep and non-human primates re preferred. To generate transgenic mice with the constructs, as exemplified herein one may inject pure, linear DNA into the pronucleus of a zygote from a pseudo pregnant female, e.g. a CB56 female. Founders may then be identified, genotyped, and backcrossed to CB57 mice. The constructs may then be cloned and optionally verified, for instance by Sanger sequencing. Knock outs are envisaged where for instance one or more genes are knocked out in a model. However, knockins are also envisaged (alone or in combination), with Cas9 knockins as preferred. To generate a Cas9 knock in mice one may target the same constitutive and conditional constructs to the Rosa26 locus. Animal models envisioning both inducible and constitutive Cas9 expression are contemplated. Methods of generating animals having inducible and constitutive Cas9 expression may be extrapolated from a transgenic mouse to another animal model. Methods of US Patent Publication Nos. 20120017290 and 20110265198 assigned to Sangamo BioSciences, Inc. directed to targeting the Rosa locus may be modified to utilize the CRISPR-Cas system of the present invention. In another embodiment, the methods of US Patent Publication No. 20130236946 assigned to Cellectis directed to targeting the Rosa locus may also be modified to utilize the CRISPR-Cas system of the present invention.

Animal models of neurological disorders are reviewed by Chesselet and Carmihael in Neurotherapeutics. April 2012; 9(2): 241-244 with many presented in the same issue, the disclosure of which is incorporated by reference along with all references cited therein, including, but not limited to, the below referenced disclosures. Auvin et al. [Neurotherapeutics 2012. doi:10.1007/s13311-012-0119-8] discuss rules in animal modeling of pediatric epilepsy syndromes. This is a challenging field for animal modeling, because it needs to include not just the model of a progressive pathology, but also needs to take account of early brain development in the disease and differences in brain developmental timelines between the rodent and humans. Auvin et al. [Neurotherapeutics 2012. doi:10.1007/s13311-012-0119-8] elaborate on a set of 5 principles for pediatric epilepsy models, but ones that also apply more generally to an animal model of CNS disease. Hoke [Neurotherapeutics 2012. doi:10.1007/s13311-012-0116] amplifies these animal modeling principles in a careful review of rodent models of peripheral neuropathy, with a focus on diabetic, chemotherapeutic, and human immunodeficiency virus peripheral neuropathies.

In single gene disease states, mouse transgenic modeling would seem to offer an ideal platform for exact molecular mimicry of the causal condition. In Huntington's disease, the genetic etiology of a cytosine-adenine-guanine (CAG) repeat expansion in the huntingtin gene has been known for some time [Neurotherapeutics 2012. doi:10.1007/s13311-012-0112-2]. However, models that broadly express the mutation have provided useful tools for understanding pathophysiology and testing drugs (more sophisticated genetic approaches that can be used to ask mechanistic questions about the role of specific cell populations in the disease process). Ehrlich [Neurotherapeutics 2012. doi: 10.1007/s13311-012-0112-2] review data from different animal models and derived cell culture studies, and how these can inform cell autonomous and noncell autonomous interactions in the development of Huntington's disease pathology. In many cases, animal models of single gene disorders have not been simple to generate. In Machado-Joseph disease (spinocerebellar ataxia 3) variations in triplet nucleotide expansion in the ataxin 3 gene along with 2 isoforms of the gene product (mjd1a and ataxin3) lead to a complex clinical presentation, including variations in cerebellar, basal ganglia, corticospinal tract, oculomotor, and muscle signs [Ann Neurol 1996; 39:490-499]. Colomer Gould [Neurotherapeutics 2012. doi:10.1007/s13311-012-0117-x] describes distinct transgenic strategies that vary the gene promoter, triplet repeats, isoform, and conditional expression to model high intermediate and low severity phenotypes in this disease. On the other hand, rare genetic mutations have provided an unexpected window into the understanding of the largely nongenetic illness, Parkinson's disease. As reviewed by Chesselet et al. [Lancet Neurol. 2011; 10:1108-1118] strong evidence implicates alpha-synuclein, a rarely mutated protein, in the sporadic forms of Parkinson's disease. Accordingly, some genetic mouse models based on alpha-synuclein over-expression reproduce a wide array of Parkinson's disease-like deficits, opening the door to a better understanding of pathophysiology and providing a tool for preclinical drug testing in a relevant model of sporadic Parkinson's disease.

Single gene alterations in transgenic mouse models, however, rarely model the full extent or presentation of the disease in humans. Fremont and Khodakhah [Nat Med. 2007; 13:561-566] describe the difficulties in modeling single gene disorders in focal dystonia in mice. However, a unique approach has produced a valid mouse model of dystonia by infusing an antagonist to the specific gene system in a genetically modified mouse: the sodium/potassium adenosine triphosphate-ase (ATPase) inhibitor ouabain infused into cerebellum or basal ganglia of the Dyt12, sodium potassium ATPase mutated mouse. This model uses pharmacogenetics and site specific targeting to recapitulate most aspects of a human disease with multiple etiologies. From the other end of the human disease spectrum, an acute brain injury clearly has no genetic predilection. Shoch et al. illustrate the power of serial molecular analysis with mouse transgenics applied to a pathologically complex event, such as traumatic brain injury, that produces mechanistic results in studies of cell death and neuroplasticity. Finally, in complex human behavioral traits, such as addiction or affective behaviors, gene by gene studies in mouse models are severely limiting. Bubier and Chesler [Neurotherapeutics 2012. doi:10.1007/s13311-012-0111-3] describe integrative genetics and genomics that use careful genetic mapping of inbred strain hybrids to determine gene regions and gene expression patterns that underlie these complex behavioral phenotypes. This approach combines newly realized mouse genetics through bioinformatics processing to develop insights into the molecular underpinnings of behavioral traits and psychiatric disease.

The issue of brain size and complexity in modeling human disease is a recurring topic, loosely related as big brains versus small brains in animal models [Nat Med. 2007; 13:561-566]. Neuroanatomical differences between humans and rodents make modeling some CNS diseases difficult. A principle example is in white matter structure and the organization of cortical projection systems. The amount of cerebral white matter in humans is roughly $4 \times 10^6$ mm$^3$, compared with 10 mm$^3$ in the mouse [Proc Natl Acad Sci USA. 2000; 97:5621-5626]. Certain diseases are particularly focused in white matter, such as subcortical stroke in the elderly, which leads to vascular dementia, and the white matter injury in the perinatal period, which leads to cerebral palsy. There is a lack of fundamental molecular data on these diseases because of previously poor animal modeling. With precise targeting, mouse white matter can serve as a locus for a focal stroke model that in many ways mimics human subcortical white matter stroke. Sozmen et al. describe a mouse subcortical white matter stroke, and review the field of white matter stroke models in rodents. A salient point from this review is that white matter stroke sets cellular events in motion that are clearly distinct from the more commonly modeled "grey matter" or cortical and striatal rodent strokes. However, there are such profound differences in white matter structure and brain development between the rodent and the human that specific elements of white matter disease require large animal models. Back et al. [Neurotherapeutics 2012. doi:10.1007/s13311-012-0108-y] describe the instrumented fetal sheep model of white matter injury and its ability to provide a platform for imaging, pathophysiology, and therapeutic trials as a relevant model for human perinatal white matter injury. This sheep model captures not only a complex and large subcortical white matter structure, but also a time course for white matter development that much more closely follows the human progression than does that of the rodent.

Large animal models of human CNS disease are most closely approximated in the nonhuman primate. The experimental infrastructure necessary to support such studies and the experimental models themselves require substantial resources and dedicated time and personnel. Yet the benefits in modeling biodistribution and mimicking the anatomical complexity of the human brain and spinal cord may justify such expense. Cook and Tymianski [Neurotherapeutics 2012. doi:10.1007/s13311-012-0115-z] review new primate models of stroke with a particular focus on the challenges in setting up such a model, and the benefits when imaging, tissue analysis, and long-term behavioral readouts can be synchronized in 1 single stroke model. The spinal cord injury field has seen the development of many different mouse and rat animal models. Several features of the human spinal cord are not seen in rodents. The corticospinal tract of course runs in a distinctly different site within the spinal cord of the rodent compared with humans, and the degree of motor neuron innervation, direct muscular versus intrinsic spinal network control, and postlesion plasticity differ between rodents versus primates [Nat Med. 2007; 13:561-566. doi: 10.1038/nm1595, Nat Neurosci. 2010; 13:1505-1510. doi: 10.1038/nn.2691]. Importantly, the primate spinal cord contains extensive bilateral axonal collaterals compared with the rodent [J Comp Neurol. 2009; 513:151-63], which are likely to contribute to both normal and postinjury control of limb function, which is not present in rodents [Nat Neurosci. 2010; 13:1505-1510]. Nout et al. [Neurotherapeutics 2012. doi:10.1007/s13311-012-0114-0] describe a novel model of cervical spinal cord injury and forelimb control in the nonhuman primate that provides a basis for studies of regeneration and functional recovery of arm and hand control.

The issue of brain size and complexity in modeling human disease also extends down phylogenetic orders of magnitude: little brains versus connected groups of neurons. Although lacking the complex central interactions of an actual brain, lower vertebrate animal models of disease provide tractable testing of neuronal, glial, and vascular interactions within a connected and functional network. The worm has provided crucial insights into normal and pathological aging, rapid molecular characterization of candidate gene systems, and registered behavioral readouts. Dexter et al describe *Caenorhabditis elegans* modeling of movement disorders and the further use of the nematode for high throughput drug screening in a process that positions the worm model in a level above that of cell culture: an in vivo system for drug discovery. The studies in this review illustrate how the fast-moving gain and loss-of-function studies in multiple molecular pathways of a candidate gene system serially and in parallel can determine causal interaction in disease pathology.

Example 3: Mutations

As used herein, the terms "neuronal," "neurological," "nervous system-related" are used interchangeably and intended to have the same meaning. With respect to diseases and/or disorders or conditions of neuronal/neurological/nervous-system related, the present invention relates to targeting genes and mutants thereof in, for example in, but not limited to, genes involved in, associated with or correlated with, autism, autism spectrum disorders (ASDs), psychiatric/neuropsychiatric diseases or disorders, obsessive compulsive disorders (OCD), Rett syndrome, schizophrenia, Huntington's disease, etc. In this regard, mention is made of the following exemplary publications which discuss certain aspects of such diseases or disorders, the text of each of which publication is incorporated herein in its entirety for all purposes.

Peça J. et al. Shank3 mutant mice display autistic-like behaviors and striatal dysfunction. *Nature* 2011 Apr. 28; 472(7344):437-42. doi: 10.1038/nature09965. Epub 2011 Mar. 20.

Welch J. M. et al. Cortico-striatal synaptic defects and OCD-like behaviors in Sapap3-mutant mice. *Nature* 2007 Aug. 23; 448(7156):894-900.

Guy J. et al. A mouse Mecp2-null mutation causes neurological symptoms that mimic Rett syndrome. Nature Genetics March 2001; 27: 322-326.

Pouladi Mass. et al. Choosing an animal model for the study of Huntington's disease. *Nat Rev Neurosci.* 2013 October; 14 (10):708-21. doi: 10.1038/nrn3570.

Ronemus M. et al. The role of de novo mutations in the genetics of autism spectrum disorders. *Nat Rev. Genet.* 2014 February; 15(2):133-41. doi: 10.1038/nrg3585. Epub 2014 Jan. 16.

Fromer M. et al. De novo mutations in schizophrenia implicate synaptic networks. *Nature* 2014 Feb. 13; 506 (7487):179-84. doi: 10.1038/nature12929. Epub 2014 Jan. 22.

Van Rompay K. K. The use of nonhuman primate models of HIV infection for the evaluation of antiviral strategies. *AIDS Res Hum Retroviruses.* 2012 January; 28(1):16-35. doi: 10.1089/AID.2011.0234. Epub 2011 Oct. 19.

Peca et al. 2011, showed that mice with Shank3 gene deletions exhibit self-injurious repetitive grooming and deficits in social interaction. CHD8, DYRK1A, GRIN2B, KATNAL2, RIMS1, SCN2A, POGZ, ADNP, ARID1B, TBR1 is a postsynaptic protein, whose disruption at the genetic level is thought to be responsible for the development of 22q13 deletion syndrome (Phelan-McDermid syndrome) and other non-syndromic ASDs. Cellular, electrophysiological and biochemical analyses uncovered defects at striatal synapses and cortico-striatal circuits in Shank3 mutant mice. The authors' findings demonstrated a critical role for SHANK3 in the normal development of neuronal connectivity and established causality between a disruption in the Shank3 gene and the genesis of autistic-like behaviours in mice.

Welch et al. 2007, showed that mice with genetic deletion of Sapap3 exhibit increased anxiety and compulsive grooming behaviour leading to facial hair loss and skin lesions. SAP90/PSD95-associated protein 3 (SAPAP3; also known as DLGAP3) is a postsynaptic scaffolding protein at excitatory synapses that is highly expressed in the striatum. Electrophysiological, structural and biochemical studies of Sapap3-mutant mice reveal defects in cortico-striatal synapses. Furthermore, the author showed that lentiviral-mediated selective expression of Sapap3 in the striatum rescued the synaptic and behavioural defects of Sapap3-mutant mice. The authors' findings demonstrated a critical role for SAPAP3 at cortico-striatal synapses and emphasized the importance of cortico-striatal circuitry in OCD-like behaviours.

Guy et al. 2001, generated mice lacking Mecp2 using Cre-loxP technology. The authors observed that both Mecp2-null mice and mice in which Mecp2 was deleted in brain showed severe neurological symptoms at approximately six weeks of age. Rett syndrome (RTT) is an inherited neurodevelopmental disorder of females that occurs once in 10,000-15,000 births. Affected females develop normally for 6-18 months, but then lose voluntary movements, including speech and hand skills. Most RTT patients are heterozygous for mutations in the X-linked gene MECP2, encoding a protein that binds to methylated sites in genomic DNA and facilitates gene silencing.

Ronemus et al. 2014, provide a review of the recent advances in identification of the genetic components of autism spectrum disorders (ASDs), particularly the demonstration of de novo mutations as an important source of causality. The authors review these developments in light of genetic models for ASDs. The authors consider the number of genetic loci that underlie ASDs and the relative contributions from different mutational classes, and discuss possible mechanisms by which these mutations might lead to dysfunction.

The present invention relates to targeting genes and mutants thereof involved in autism spectrum disorders, for example, but not limited to, genes with recurrent de novo loss-of-function mutations (such as CHD8, DYRK1A, GRIN2B, KATNAL2, RIMS1, SCN2A, POGZ, ADNP, ARID1B, TBR1) (see e.g., Ronemus et al. 2014).

Fromer et al. 2014, discuss insights into aetiological mechanisms for schizophrenia and reveal pathophysiology shared with other neurodevelopmental disorders. The authors showed that in schizophrenia, small de novo mutations, affecting one or a few nucleotides, are overrepresented among glutamatergic postsynaptic proteins comprising activity-regulated cytoskeleton-associated protein (ARC) and N-methyl-D-aspartate receptor (NMDAR) complexes. The authors further discuss that mutations are additionally enriched in proteins that interact with these complexes to modulate synaptic strength, namely proteins regulating actin filament dynamics and those whose messenger RNAs are targets of fragile X mental retardation protein (FMRP). Genes affected by mutations in schizophrenia overlap those mutated in autism and intellectual disability, as do mutation-enriched synaptic pathways.

The present invention relates to targeting genes and mutants thereof, in genes which overlap between neurological and psychiatric disorders, e.g., genes which overlap between schizophrenia, autism spectrum disorder and intellectual disability; for example, certain non-limiting exemplary genes include: NLRC5, STAC2, CRYBG3, SLC4A8, RAD54L2, MUC5B, MKl67, POGZ, NEB, MYH9, TANC2, SCN2A, PIK3R3, ACO1, CAPN9, CTNNA2, GRIN2A, ASH1L, LRP1, STAG1, SYNGAP1 (see e.g., Fromer et al. 2014).

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex. In particular, mutations in neurological and neuronal diseases and disorders are contemplated and include, but are not limited to, ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK5, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Daol)); Secretase Related Disorders (APH-1 (alpha and beta), Presenilin (Psenl), nicastrin, (Ncstn), PEN-2, Nosl, Parpl, Natl, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10).

Example 4: Cre-Based Models

Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. This same concept is what makes the conditional Cas9 mouse so useful. A cross of the conditional Cas9 mouse with a mouse that ubiquitously expresses Cre (ACTB-Cre line) may arrive at a mouse that expresses Cas9 in every cell. Delivery of chimeric RNA induces genome editing in embryonic or adult mice. Hence, the methods described herein comprising the delivery of chimeric RNA are within the scope of the invention where delivery is to any age or development stage, e.g., embryonic mice, post-natal pups and/or adult mice. Interestingly, if the conditional Cas9 mouse is crossed with a mouse expressing Cre under a tissue specific promoter, there is only be Cas9 in the tissues that also express Cre. This approach may be used to edit the genome in only precise tissues by delivering chimeric RNA to the same tissue.

Reference is made to Madisen et al., Nat Neurosci. 2010 January; 13(1): 133-140 which relates to a Cre/lox system utilizing the Rosa26 locus to develop a universal Cre-responder. The Cre-lox system, discovered in bacteriophage P1 uses the enzyme Cre recombinase to drive recombination of DNA between two loxP sites. Reference is also made to the Cre-driver Network (www.credrivermice.org/) which is an initiative to create a collection of mouse strains that offer scientists the ability to make precise alterations in brain-related genes as a way of exploring their impact on brain function. The technology used to create mice for the Cre-driver Network involves the targeted insertion in the mouse genome of a gene for Cre recombinase, an enzyme that triggers the swapping, or recombination, of stretches of DNA in chromosomes. Cre offers several levels of control over recombination: both the insertion site of Cre and the recombination events it triggers can be precisely targeted; and it can be inserted in the genome in a way that scientists can induce recombination at a desired time and in selected cell populations. It offers a versatile way to study how patterns of gene activity, or gene expression, affect brain development. Further, these Cre-drivers represent "genetic switches" that can turn on a growing variety of genetically encoded elements, enabling scientists to target specific neuron types in the analysis of neural circuit development, function, and dysfunction. The present invention contemplates utilizing a Cre-driver line for a backcross to a Cas9 mouse to create a further model.

However, there may be metabolic pitfalls of CNS-Cre-based technology, such as aberrant tissue expression, unintentional recombinase binding, recombination at unintentional sites, nonspecific expression of Cre recombinases, and unintended phenotypes (see, e.g., Harno et al., Cell Metabolism, Volume 18, Issue 1, p21-28, 2 Jul. 2013). Technological advances include, but are not limited to, targeted viruses (such as, AAV), inducible-Cre systems (such as self-deleting Cre), optogenetics, and DREADD (designer receptors exclusively activated by designer drugs) technology to modify gene expression (see, e.g., Harno et al., Cell Metabolism, Volume 18, Issue 1, p21-28, 2 Jul. 2013).

This approach may be extrapolated to other animal models in which a transgenic model contains an inducible Cas9 that may be activated by co-expression with Cre.

Example 5: Loss-of-Function and Functional Screens

The present invention also contemplates loss-of-function screens. The CRISPR-Cas system can be used to transiently silence or knock down gene expression. The screens may be performed in cell culture-based assays or experimental organisms (such as a transgenic animal of the present invention) can be used to systematically disrupt nearly every gene in a genome or subsets of genes (sub-genomes); possible functions of disrupted genes can be assigned based on observed phenotypes.

Multiple mutations may thus be introduced using any number of sgRNAs, e.g. the vector may comprise at least 3 sgRNAs, at least 8 sgRNAs, at least 16 sgRNAs, at least 32 sgRNAs, at least 48 sgRNAs, or at least 50 sgRNAs. Alternatively, the vector may comprise 1-2 sgRNAs, 1-3 sgRNAs, 1-4 sgRNAs, 1-5 sgRNAs, 3-6 sgRNAs, 3-7 sgRNAs, 3-8 sgRNAs, 3-9 sgRNAs, 3-10 sgRNAs, 3-16 sgRNAs, 3-30 sgRNAs, 3-32 sgRNAs, 3-48 sgRNAs or 3-50 sgRNAs. The mutation(s) can include the introduction, deletion, or substitution of one or more nucleotides at each target sequence of cell(s) via the guide(s) or RNA(s) or sgRNA(s) resulting in loss-of-function and/or gain-of-function of the target(s). The mutations can include the introduction, deletion, or substitution of 1-75 nucleotides at each target sequence of said cell(s) via the guide(s) or RNA(s) sgRNA(s) resulting in loss-of-function or gain-of-function of the target(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain-of-function of the target(s). The mutations can include the introduction, deletion, or substitution of 40, 45, 50, 75, 100, 200, 300, 400 or 500 nucleotides at each target sequence of said cell(s) via the guide(s) or RNA(s) or sgRNA(s) resulting in loss-of-function or gain-of-function of the target.

The techniques developed for RNAi loss-of-function screens is applicable to the CRISPR-Cas system of the present invention. For example, the methods reviewed by Campeau and Godeil (see, e.g., Briefings in Functional Genomics (2011)10(4): 215-226) for screening strategies involving RNAi may be applied to the CRISPR-Cas system of the present invention.

Several delivery methods are contemplated for guide(s) or RNA(s) or sgRNA(s) and are exemplified below.

Viral delivery. Guide(s) or RNA(s) or sgRNA(s) can be delivered using adeno associated virus (AAV), lentivirus, adenovirus or other viral vector types, or combinations thereof. Cas9 and one or more guide RNAs can be packaged into one or more viral vectors.

Lentivirus. Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquotted and immediately frozen at −80 C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285, Published online 21 Nov. 2005 in Wiley InterScience (www.interscience.wiley.com). DOI: 10.1002/jgm.845). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of $2.5 \times 10^6$ CD34+ cells per kilogram patient weight may be collected and prestimulated for 16 to 20 hours in X-VIVO 15 medium (Lonza) containing 2 mML-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm² tissue culture flasks coated with fibronectin (25 mg/cm²) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the train, see, e.g., US Patent Publication Nos. US20110293571; US20110293571, US20040013648, US20070025970, US20090111106 and U.S. Pat. No. 7,259,015.

RNA delivery. The guide(s) or RNA(s) or sgRNA(s) can also be delivered in the form of RNA. Cas9 mRNA can be generated using in vitro transcription. For example, Cas9 mRNA can be synthesized using a PCR cassette containing the following elements: T7_promoter-kozak sequence (GC-CACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce toxicity, the CRISPR enzyme and/or guide RNA can be modified using pseudo-U or 5-Methyl-C.

mRNA delivery methods are especially promising for liver delivery currently. In particular, for AAV8 is particularly preferred for delivery to the liver.

Nanoparticles. Guide(s) or RNA(s) or sgRNA(s) may be delivered using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular deliver of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used/and or adapted to the CRISPR-Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR-Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 0110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30.-100 C., preferably at approximately 50.-90 C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 0110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR-Cas system of the present invention.

In another embodiment, lipid nanoparticles (LNPs) are contemplated. In particular, an antitransthyretin small interfering RNA encapsulated in lipid nanoparticles (see, e.g., Coelho et al., N Engl J Med 2013; 369:819-29) may be applied to the CRISPR-Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering CRISPR-Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as siRNA oligonucleotides may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 µg/ml levels may be contemplated, especially for a formulation containing DLinKC2-DMA.

Preparation of LNPs and CRISPR-Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(w-methoxy-poly(ethylene glycol)2000) carbamoyl]-1,2-dimyristyloxypropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR-Cas RNA may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. siRNA encapsulation efficiency may be determined by removal of free siRNA using VivaPureD MiniH columns (Sartorius Stedim Biotech) from samples collected before and after dialysis. The encapsulated RNA may be extracted from the eluted nanoparticles and quantified at 260 nm. siRNA to lipid ratio was determined by measurement of cholesterol content in vesicles using the Cholesterol E enzymatic assay from Wako Chemicals USA (Richmond, Va.).

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an siRNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Spherical Nucleic Acid (SNA™) constructs and other nanoparticles (particularly gold nanoparticles) are also contemplate as a means to delivery CRISPR/Cas system to intended targets. Significant data show that AuraSense Therapeutics' Spherical Nucleic Acid (SNA™) constructs, based upon nucleic acid-functionalized gold nanoparticles, are superior to alternative platforms based on multiple key success factors, such as:

High in vivo stability. Due to their dense loading, a majority of cargo (DNA or siRNA) remains bound to the constructs inside cells, conferring nucleic acid stability and resistance to enzymatic degradation.

Deliverability. For all cell types studied (e.g., neurons, tumor cell lines, etc.) the constructs demonstrate a transfection efficiency of 99% with no need for carriers or transfection agents.

Therapeutic targeting. The unique target binding affinity and specificity of the constructs allow exquisite specificity for matched target sequences (i.e., limited off-target effects).

Superior efficacy. The constructs significantly outperform leading conventional transfection reagents (Lipofectamine 2000 and Cytofectin).

Low toxicity. The constructs can enter a variety of cultured cells, primary cells, and tissues with no apparent toxicity.

No significant immune response. The constructs elicit minimal changes in global gene expression as measured by whole-genome microarray studies and cytokine-specific protein assays.

Chemical tailorability. Any number of single or combinatorial agents (e.g., proteins, peptides, small molecules) can be used to tailor the surface of the constructs.

This platform for nucleic acid-based therapeutics may be applicable to numerous disease states, including inflammation and infectious disease, cancer, skin disorders and cardiovascular disease.

Citable literature includes: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, doi.org/10.1002/sml1.201302143.

Self-assembling nanoparticles with siRNA may be constructed with polyethyleneimine (PEI) that is PEGylated with an Arg-Gly-Asp (RGD) peptide ligand attached at the distal end of the polyethylene glycol (PEG), for example, as a means to target tumor neovasculature expressing integrins and used to deliver siRNA inhibiting vascular endothelial growth factor receptor-2 (VEGF R2) expression and thereby tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR-Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOT-NETS ester) was ordered from Macrocyclics (Dallas, Tex.). The amine modified RNA sense strand with a 100-fold molar excess of DOT-NETS ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a siRNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR-Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

Exosomes. Exosomes are endogenous nano-vesicles that transport RNAs and proteins which can deliver short interfering (si)RNA to the brain in mice. To reduce immunogenicity, Alvarez-Erviti et al. (2011, Nat Biotechnol 29: 341) used self-derived dendritic cells for exosome production. Targeting was achieved by engineering the dendritic cells to express Lamp2b, an exosomal membrane protein, fused to the neuron-specific RVG peptide3. Purified exosomes were loaded with exogenous siRNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MEW) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled siRNA was used for the empirical optimization of the electroporation protocol. The amount of encapsulated siRNA was assayed after ultracentrifugation and lysis of exosomes. Electroporation at 400 V and 125 µF resulted in the greatest retention of siRNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG pep tide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether siRNA-RVG exosomes induced immune responses in vivo by assessing IL-6, IP-10, TNFα and IFN-α serum concentrations. Following siRNA-RVG exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR-Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of siRNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading siRNA into exosomes. Finally, El-Andaloussi et al. outline how to use exosomes to efficiently deliver siRNA in vitro and in vivo in mouse brain. Examples of anticipated results in which exosome-mediated siRNA delivery is evaluated by functional assays and imaging are also provided. The entire protocol takes ~3 weeks. Delivery or administration according to the invention may be performed using exosomes produced from self-derived dendritic cells.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property might be useful in gene therapy.

Exosomes from plasma are prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Qiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR-Cas into exosomes may be conducted similarly to siRNA. The exosomes may be co-cultured with monocytes and lymphocytes isolated from the peripheral blood of healthy donors. Therefore, it may be contemplated that exosomes containing CRISPR-Cas may be introduced to monocytes and lymphocytes of and autologously reintroduced into a human. Accordingly, delivery or administration according to the invention may be performed using plasma exosomes.

Liposomes. Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

Conventional liposome formulation is mainly comprised of natural phospholipids and lipids such as 1,2-distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA may be contemplated for in vivo administration in liposomes.

In another embodiment, the guide(s) or RNA(s) or sgRNA(s) may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR-Cas targeted in a SNALP are contemplated. The daily treatment may be over about three days and then weekly for about five weeks. In another embodiment, a specific CRISPR-Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR-Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic siRNA during particle formation. When positively charged under increasingly acidic endosomal conditions, the ionizable lipid also mediates the fusion of SNALP with the endosomal membrane enabling release of siRNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALPsiRNA formulations. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid were solubilized in ethanol at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM Na2HPO4, 1 mM KH2PO4, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method may be extrapolated to the CRISPR-Cas system of the present invention.

Other Lipids. Other cationic lipids, such as amino lipid 2,2-dilinoleyl-4-dimethylaminoethyl-[1,3]-dioxolane (DLin-KC2-DMA) may be utilized to encapsulate guide(s) or RNA(s) or sgRNA(s) similar to SiRNA (see, e.g., Jayaraman, Angew. Chem. Int. Ed. 2012, 51, 8529-8533). A preformed vesicle with the following lipid composition may be contemplated: amino lipid, di stearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11_0.04 (n=56), the particles may be extruded up to three times through 80 nm membranes prior to adding the CRISPR-Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011) Published online 9 Jan. 2011) describes the use of lipid envelopes to deliver RNA. Use of lipid envelopes is also preferred in the present invention.

In another embodiment, lipids may be formulated with the CRISPR-Cas system of the present invention to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR-CasCRISPR-Cas instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid: siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 0.1766035; 1519714; 1781593 and 1664316), all of which may be used/and or adapted to the present invention.

The CRISPR-Cas system may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart. Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine and phosphorous containing compounds with a mixture of amine/amide or $N-P(O_2)S$ as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered."

Supercharged proteins. Supercharged proteins are a class of engineered or naturally occurring proteins with unusually high positive or negative net theoretical charge. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, siRNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of siRNA and plasmid DNA into mammalian cells are valuable both for research and therapeutic applications (Akinc et al., 2010, Nat. Biotech. 26, 561-569). Purified +36 GFP protein (or other superpositively charged protein) is mixed with siRNAs in the appropriate serum-free media and allowed to complex prior addition to cells. Inclusion of serum at this stage inhibits formation of the supercharged protein-siRNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and siRNA should be performed to optimize the procedure for specific cell lines.

(1) One day before treatment, plate $1 \times 10^5$ cells per well in a 48-well plate.

(2) On the day of treatment, dilute purified +36 GFP protein in serumfree media to a final concentration 200 nM. Add siRNA to a final concentration of 50 nM. Vortex to mix and incubate at room temperature for 10 min.

(3) During incubation, aspirate media from cells and wash once with PBS.

(4) Following incubation of +36 GFP and siRNA, add the protein-siRNA complexes to cells.

(5) Incubate cells with complexes at 37 C for 4 h.

(6) Following incubation, aspirate the media and wash three times with 20 U/mL heparin PBS. Incubate cells with serum-containing media for a further 48 h or longer depending upon the assay for knockdown.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1 \times 10^5$ per well in a 48-well plate.

(2) On the day of treatment, dilute purified +36 GFP protein in serumfree media to a final concentration 2 mM. Add 1 mg of plasmid DNA. Vortex to mix and incubate at room temperature for 10 min.

(3) During incubation, aspirate media from cells and wash once with PBS.

(4) Following incubation of +36 GFP and plasmid DNA, gently add the protein-DNA complexes to cells.

(5) Incubate cells with complexes at 37 C for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR-Cas system of the present invention.

Cell penetrating peptides. In yet another embodiment, cell penetrating peptides (CPPs) are contemplated for the delivery of the guide(s) or RNA(s) sgRNA(s) of the present invention. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, nanoparticles, liposomes, chromophores, small molecules and radioactive materials. In aspects of the invention, the cargo may also comprise any component of the CRISPR-Cas system or the entire functional CRISPR-Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intraarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951 provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery may be in U.S. Pat. Nos. 8,575,305; 8; 614,194 and 8,044,019.

That CPPs can be employed to deliver the CRISPR-Cas system is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged nanoparticles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Example 6: Generation of Chd8 Loss-of-Function Mutant Mouse Via Cas9-Mediated Germline Editing To study the role of heterozygous Chd8 loss-of-function in ASD, using CRISPR-Cas9 Applicants generated Chd8 germline mutant mice and proceeded with the molecular, cellular, and behavioral of these animals (FIG. 1A).

Figure 5:
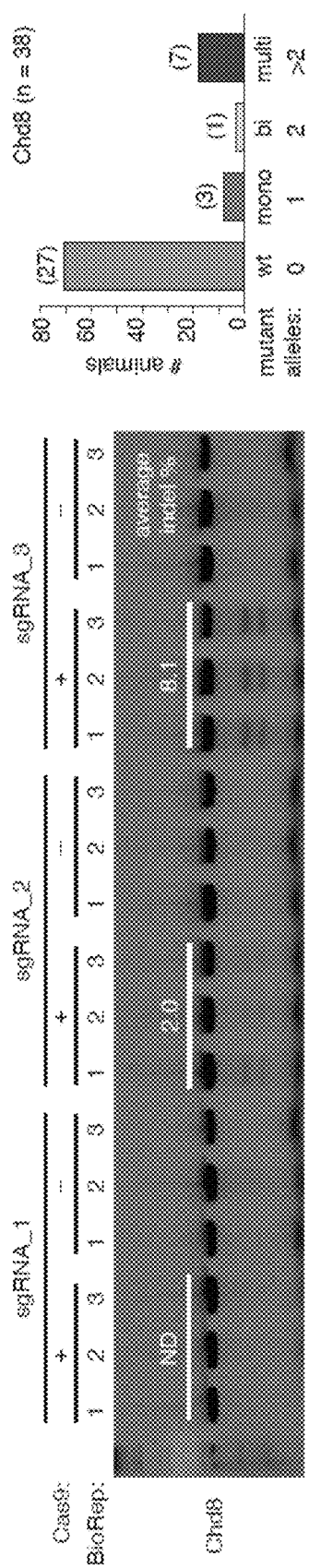
FIG. 5 illustrates in vitro validation of Chd8-targeted sgRNA and quantification of first generation gene edited progeny. (Left) In vitro validation and quantification of Chd8-targeted sgRNA efficiency in mouse N2a cells using the SURVEYOR assay for three biological replicates with and without Cas9 co-transfection. (Right) Classification and quantification of mosaic founder genotypes. Mice were classified by having no (WT), one (monoallelic), two (biallelic), or >2 (multiallelic) mutant allele(s). Data are (Left) mean indel percent and (Right) total number of animals.

Mutations in CHD8 identified in patients are most often LOF, and therefore Applicants reasoned that a Cas9-mediated indel causing a frameshift mutation within an early constitutive exon would be sufficient to disrupt protein expression and best model the LOF variants found in ASD patients (FIG. 1B). Applicants designed three sgRNAs targeted to the Chd8 gene and tested their efficiency by transient transfection in mouse N2A cells followed by the SURVEYOR assay (FIG. 5). The optimal sgRNA was identified, co-injected with Cas9 mRNA into the pronucleus of single cell zygotes, and implanted into recipient mothers at the two-cell stage (Wang et al., 2013). Progeny were born with a variety of mutant alleles harboring indels at the target site (FIG. 1C). Genotyping tail tissue revealed that individual animals had between 1 and 4 unique alleles, indicating that the first generation of gene edited progeny contained mosaics. These animals likely resulted from unique editing events after division of the single cell zygote. To characterize the distribution of genotypes, animals were classified as having zero (wild-type, n=27), one (monoallelic, n=3), two (biallelic, n=1), or more than two (multiallelic, n=7) mutant allele(s) (FIG. 1D and FIG. 5).

Figure 6A:
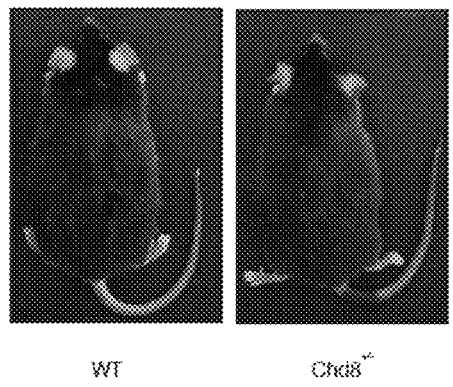
FIG. 6A-E. illustrates that Chd8$^{+/-}$ mice are smaller than their wild-type littermates and display ASD-like behavior. 6A. Representative images of adult Chd8$^{+/-}$ mice and wild-type littermates. 6B. Weights of adult Chd8$^{+/-}$ mice (n=18) compared to wild-type littermates (n=28). 6C. In the elevated plus maze, Chd8$^{+/-}$ mice (n=10) spent an equal amount of time in each region compared to wild-type littermates (n=10). 6D. In the open field test, Chd8$^{+/-}$ mice (n=8) traveled the same distance compared to wild-type littermates (n=9). 6E. In the rotarod performance test, Chd8$^{+/-}$ mice (n=10) spent more time on the rotating rod before falling off compared to wild-type littermates (n=10). One trial was performed per day for five days. Data are means±SEM; (B-D) two-tailed t-test and (E) two-way repeated measure ANOVA with post hoc two-tailed t-test. *$p<0.05$, $p<0.01$, *$p<0.001$.
Figure 6B:
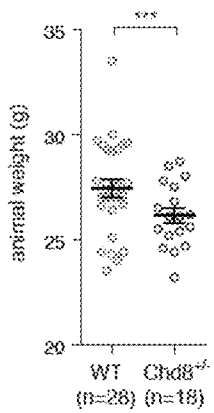

To establish a mouse line with a single, germline transmitted LOF mutation in Chd8, Applicants crossed all of the first generation Chd8 mutant progeny (n=11) to wild-type mice. Within each resulting litter at least one progeny harbored a mutant allele identified within the parent. Applicants also identified new alleles not found in the tail snips of parents. Therefore, Applicants refer to the first generation of germline edited progeny as 'mosaic founders' to distinguish them from true founders with germline transmission of a single unique allele. One founder with germline transmission of a Chd8 allele containing a 7-nucleotide deletion (FIG. 1C), and thus a frameshift mutation, was selected to establish the strain. As expected, homozygous mutant animals were not viable. Heterozygous mice showed approximately half the expression of CHD8 as compared to wild-type littermates (FIG. 1E). Chd8$^{+/-}$ mice were viable and fertile and did not display any apparent anatomical abnormality, but they did weigh less than their wild-type (WT) littermates (WT 27.4±0.4 g; Chd8$^{+/-}$ 26. 2±0.4 g) (FIG. 6A-B). Taken together our results demonstrate that Cas9-mediated zygote editing results in mosaic founders with potential for germline transmission of Chd8 LOF alleles, and that these mice resemble previously reported Chd8 mutant mice generated by traditional gene targeting methods (Nishiyama et al., 2004).

Example 7:Chd8$^{+/-}$ Mice Display Impaired Social Interaction and Increased Repetitive Behavior In the DSM-5 (Diagnostic and Statistical Manual of Mental Disorders), ASD is defined using two hallmark behaviors as diagnostic criteria: (i) persistent deficits in social interaction across multiple contexts and (ii) restrictive and repetitive patterns of behavior, interests or activities. Several ASD models have shown that mice carrying human autism risk factors recapitulate aspects of these hallmarks (Baudouin et al., 2012; Chadman et al., 2008; Kwon et al., 2006; Peca et al., 2011; Rothwell et al., 2014). To assess whether Chd8$^{+/-}$ mice exhibited behaviors similar to the ASD hallmarks Applicants utilized several established paradigms to evaluate behavioral phenotypes. The first test was a three chamber social interaction test, which involves a habituation and two social scenarios. In the first scenario, which tests sociability, experimental mice were given the option to interact with an unfamiliar mouse in a wire cup (Stranger 1) or an empty wire cup (Empty). Wild-type littermates spent more time with Stranger 1 (WT-Stranger 1: 66±6 sec SEM) over the empty cup (WT-Empty: 38±5 sec SEM), whereas Chd8$^{+/-}$ mice spent equal time with Stranger 1 (Chd8$^{+/-}$-Stranger 1: 56±8 sec SEM) and the empty cup (Chd8$^{+/-}$-Empty: 52±5 sec SEM) (FIG. 2A). In the second scenario, which tests social novelty, experimental mice were given the option of interacting with Stranger 1 or a new unfamiliar mouse (Stranger 2). In this scenario, both Chd8$^{+/-}$ mice and wild-type littermates preferred Stranger 2, but wild-type mice spent even more time with the new mouse (WT-Stranger 2: 52±5 sec SEM) compared to Chd8$^{+/-}$ mice (Chd8$^{+/-}$-Stranger 2: 45±5 sec SEM) (FIG. 2B-C). Further analysis of the two scenarios of the test showed that Chd8$^{+/-}$ mice demonstrated decreased sociability (time spent interacting with Stranger 1 as a fraction of the total time spent interacting with Stranger 1 and with the empty cup; WT 0.64±0.03 SEM; Chd8$^{+/-}$ 0.51±0.05 SEM) and preference for social novelty (time spent interacting with Stranger 2 as a fraction of the total time spent interacting with Stranger 2 and with Stranger 1; WT 0.75±0.03 SEM; Chd8$^{+/-}$ 0.62±0.05 SEM) (FIG. 2C).

Applicants then tested whether the reduced preference for social novelty was restricted to a social context by performing the novel object recognition test. The first phase of this test involves placing an experimental mouse in a novel arena with two novel objects. In this phase Applicants found that Chd8$^{+/-}$ mice spent less time interacting with both objects (0.4±0.2 sec SEM) compared to wild-type littermates (2.7±0.3 sec SEM) (FIG. 2D). In the second phase of the test, one of the familiar objects remained in the arena while the second was replaced with a new novel object. In this phase, Applicants found that Chd8$^{+/-}$ mice spent less time interacting with the novel object (WT 2.4±0.5 sec SEM; Chd8$^{+/-}$ 0.5±0.4 sec SEM) but the same amount of time with the familiar object compared to wild-type littermates (WT 0.9±0.4 sec SEM; Chd8$^{+/-}$ 0.3±0.2 sec SEM) (FIG. 2E). These data suggest that Chd8$^{+/-}$ mice are averse to social and novel interactions.

Figure 6C:
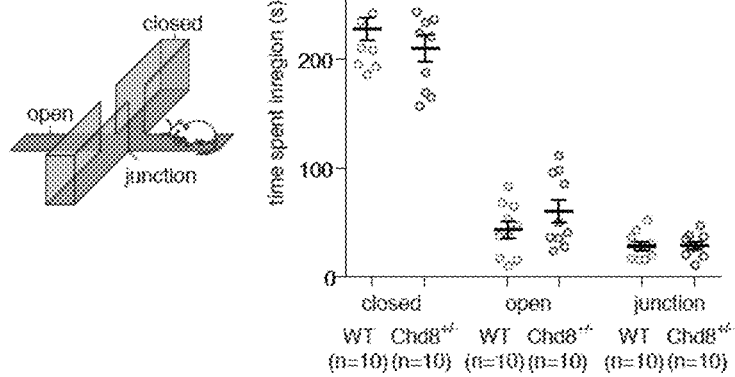
Figure 6D:
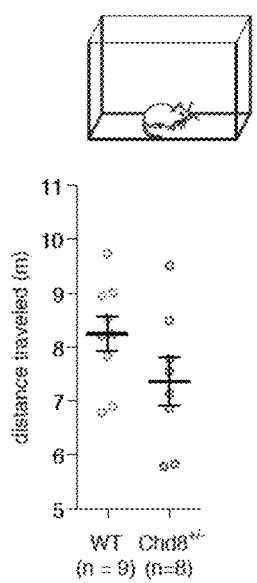

Anxiety is a common co-morbidity with autism, and as such Applicants wanted to assess how Chd8$^{+/-}$ mice respond to a novel environment and mild stressors. To do this, Applicants characterized the animals in the dark-light emergence test, elevated plus maze, and open field tests. In the dark-light emergence test, which takes place in a two-chamber arena with differential lighting, Applicants observed an increase in the latency to enter the light side of the arena from the dark side (WT 45±10 sec SEM; Chd8$^{+/-}$ 179±50 sec SEM)(FIG. 2F) but not in the total time spent in the light side of the arena (WT 127±22 sec SEM; Chd8$^{+/-}$ 91±25 sec SEM)(FIG. 2G). In the elevated plus maze, an elevated platform with two arms covered and two arms exposed, Applicants found that Chd8$^{+/-}$ mice and wild-type littermates spent equal amounts of time in each region (FIG. 6C). Finally, Applicants conducted the open field test, wherein mice are placed in a novel square arena, and found that although Chd8$^{+/-}$ mice and wild-type littermates traveled the same distance (FIG. 6D), Chd8$^{+/-}$ mice spent less time in the center (WT 483±56 sec SEM; Chd8$^{+/-}$ 222±30 sec SEM) (FIG. 2H). Collectively, these observations suggest Chd8$^{+/-}$ mice exhibit some increased levels of anxiety.

Figure 6E:
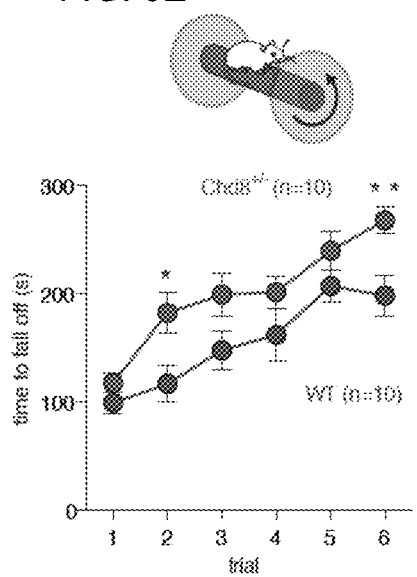

Applicants next asked whether Chd8$^{+/-}$ mice exhibited the second DSM hallmark, restrictive, repetitive patterns of behavior. To investigate this Applicants performed the rotarod performance test as a proxy for acquired repetitive motor learning (Rothwell et al., 2014) and found that Chd8$^{+/-}$ mice outperformed their wild-type littermates (FIG. 2I). Experimental conditions for rotarod vary widely across laboratories so to confirm our result Applicants reproduced the phenotype in a later generation of mice using different experimental conditions (FIG. 6E). This phenotype is a distinct feature shared among several other ASD mouse models, which include PTEN knockout (Kwon et al., 2006), NLGN3 R451C missense mutations, and NLGN3 knockout (Rothwell et al., 2014) among others (Etherton et al., 2009; Nakatani et al., 2009; Penagarikano et al., 2011). Taken together, these results are consistent with reduced social interaction, insistence on sameness, and restrictive interests similar to those commonly found in ASD patients.

Example 8: Synaptic Dysfunction of MSNs in the NAc of Chd8$^{+/-}$ Mice

Figure 7B:
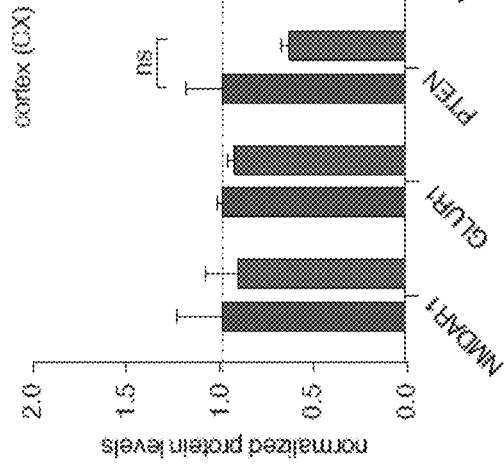
FIG. 7A-H. illustrates brain region-specific protein expression profiling. 7A-D. Protein expression profiling on adult tissue collected from the (A) hippocampus, (B) cortex, (C) cerebellum, and (D) amygdala. Each lane was loaded with 5 µg of protein with GAPDH and ACTB as loading controls and normalized to wild-type levels. Samples from three different animals for each genotype were compared. 7E-H. Comparison of (E) NR2A, (F) NR2B, (G) NMDAR1, and (H) GLUR1 protein expression throughout distinct brain regions. Each lane was loaded with 5 µg of protein with GAPDH and ACTB as loading controls and normalized to wild-type levels. Samples from three different animals for each genotype were compared. Data are means±SEM; two-tailed t-test. *$p<0.05$.
Figure 7A:
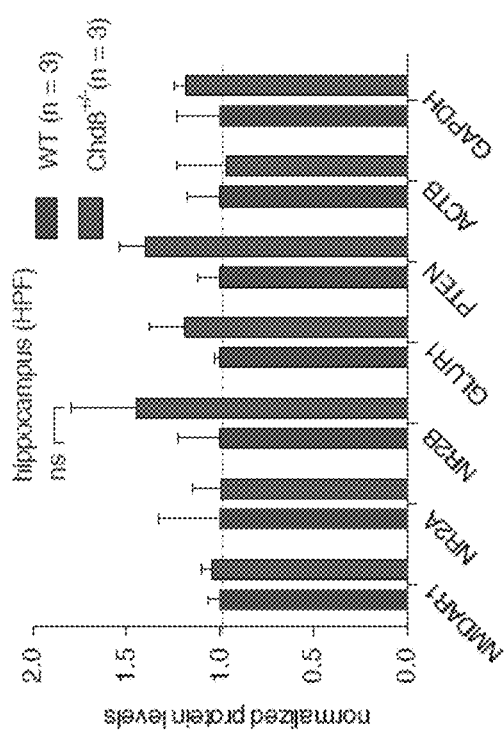
Figure 7D:
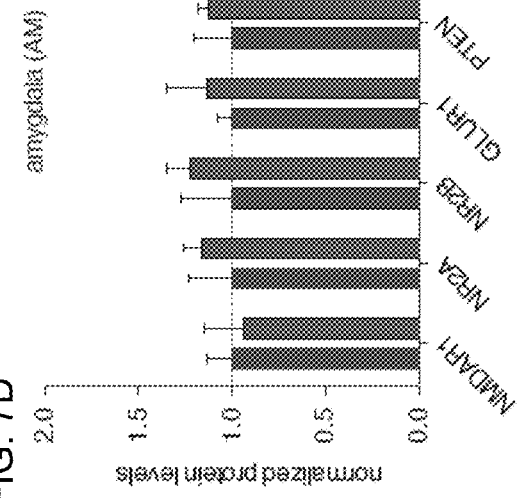
Figure 7C:
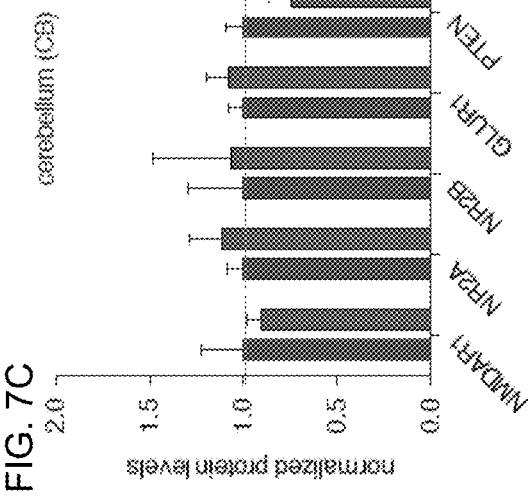
Figure 7E:
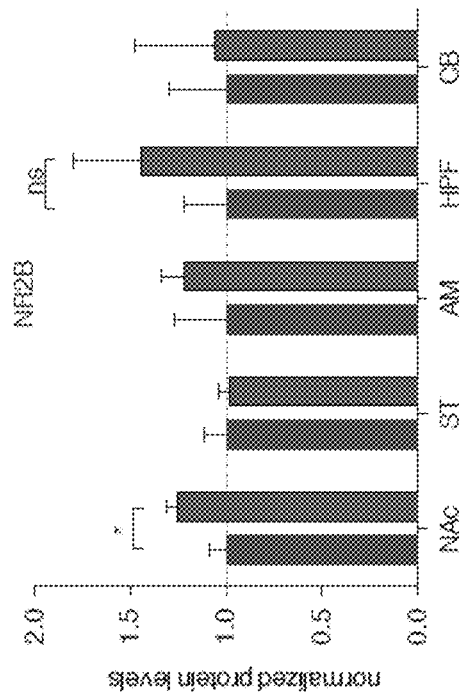
Figure 7F:
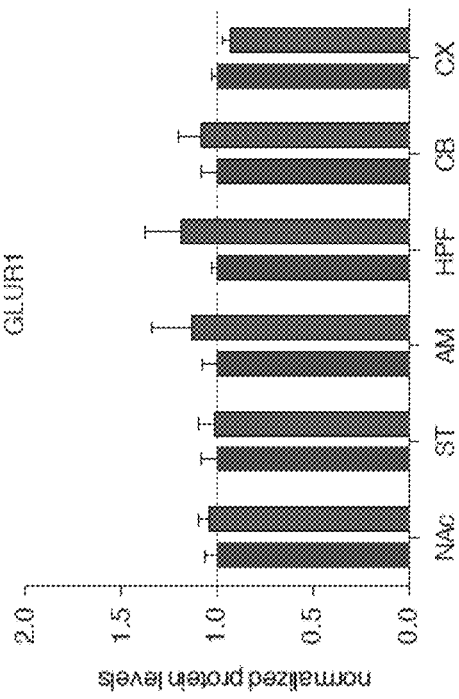
Figure 7G:
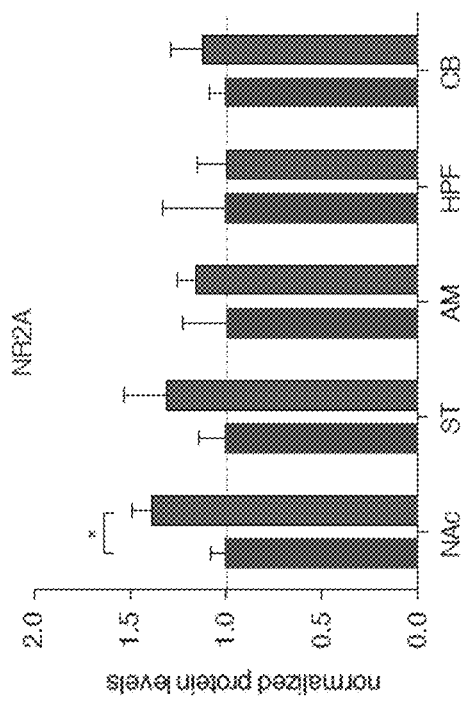
Figure 7H:
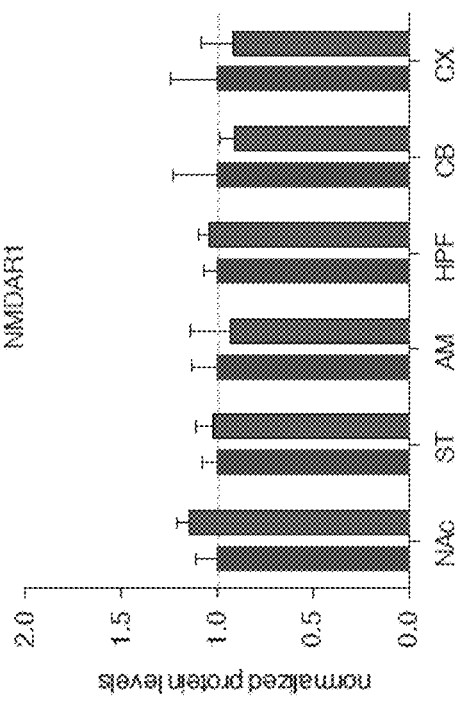

The next challenge was to determine the molecular mechanism underlying the behavior Applicants observed in Chd8$^{+/-}$ mice. Given that CHD8 is a chromatin modifier and transcription factor that binds to 2000 transcriptionally active genes (Subtil-Rodriguez et al., 2014), it may act by regulating downstream genes associated with ASD risk. Indeed, transcriptional profiling of human neural progenitor cells in which CHD8 was knocked down identified several dysregulated synaptic transcripts (Cotney et al., 2015; Talkowski et al., 2012; Wilkinson et al., 2015). To address performed brain region-specific western blots on a panel of proteins that are commonly dysregulated in ASD or commonly linked to ASD in the nucleus accumbens, dorsal striatum, hippocampus, cortex, cerebellum, and amygdala (FIG. 3A-B and FIG. 7A-H). Among the proteins assayed, Applicants found a significant increase in the expression of ionotropic glutamate receptor subunits (the NMDAR receptor subtypes NR2A and NR2B) in the nucleus accumbens (NAc). However, Applicants did not observe a change in NMDAR1, GLUR1, PTEN, or CTNNB1 (also known as beta-catenin)(FIG. 3A and FIG. 7E-F).

The observation that NR2A and NR2B expression levels are altered in the NAc, in combination with the specific ASD-like acquisition of repetitive behavior (Chadman et al., 2008; Kwon et al., 2006; Tabuchi et al., 2007) prompted us to further characterize neuronal function in this region. These repetitive and stereotyped behaviors are thought to be governed by the striatum and associated basal ganglia circuits (Balleine and O'Doherty, 2010; Graybiel, 2008; Yin and Knowlton, 2006; Costa et al., 2004; Dang et al., 2006; Yin et al., 2009). Furthermore, striatal dysfunction is frequently associated with ASD-like behavior, and in some ASD patients this part of the brain is abnormal (Di Martino et al., 2011; Hollander et al., 2005; Langen et al., 2009). Recent work utilizing two mouse models of ASD (NLGN3 KO and NLGN3 R451C) supports this idea, finding that repetitive motor learning was mediated by dopamine receptor (D1) medium spiny neurons (MSNs) in the NAc (Rothwell et al., 2014).

To determine whether $Chd8^{+/-}$ mice shared the striatal dysfunction found in other ASD models, Applicants recorded spontaneous excitatory postsynaptic current (sEPSC) of MSNs in the core region of the NAc by patch-clamp slice electrophysiology (FIG. 3C). Applicants observed that MSNs of the NAc in $Chd8^{+/-}$ mice had an increased sEPSC frequency (WT 5.0±0.4 Hz SEM; $Chd8^{+/-}$ 6.3±0.5 Hz SEM)(FIG. 3D) and amplitude (WT 16.3±0.5 pA SEM; $Chd8^{+/-}$ 19.2±0.8 pA SEM) (FIG. 3E) compared to wild-type littermates. Despite the increased spontaneous activity of the MSNs, Applicants found a decrease in spine density compared to control animals (WT 1.43±0.06 spines/μm SEM; $Chd8^{+/-}$ 1.25±0.05 spines/μm SEM), a pattern which has been found previously and was attributed to altered synapse composition (Penzes et al., 2011) or dendrite length (Ding et al., 2012) (FIG. 3F-G). Taken together these results suggest that reduction in CHD8 results in molecular dysfunction and increased excitatory inputs into the NAc.

Figure 8B:
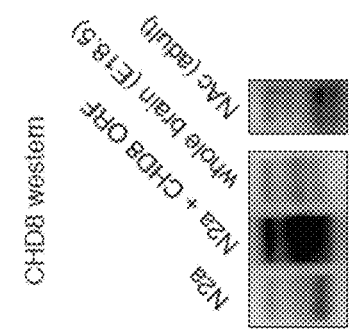
FIG. 8A-C. illustrates that CHD8 is differentially expressed throughout mouse development. 8A. Profiling of CHD8 protein expression throughout development in whole brain samples. Each lane was loaded with 5 µg of total protein with GAPDH as loading control and normalized. 8B. Validation of CHD8 antibody and protein expression in the NAc. (Left) Mouse N2a cells were transfected with a CHD8 ORF plasmid and used for western blot analysis with a mouse embryonic whole brain sample. (Right) CHD8 expression in the adult NAc. Each lane was loaded with 5 µg of protein. 8C. (Left) Schematic of a coronal brain section highlighting the NAc and DS. (Right) Representative fluorescence images within the NAc of wild-type adult brain slices probed for Chd8 or Gapdh mRNA using RNA-FISH. The dotted circle represents the anterior commissure and the enclosed region outlines the zoomed region. Scale bar represents 50 µm (5 µm for zoomed region).
Figure 8A:
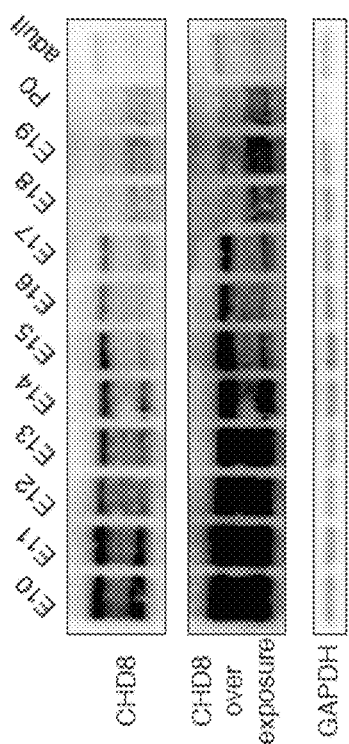
Figure 8C:
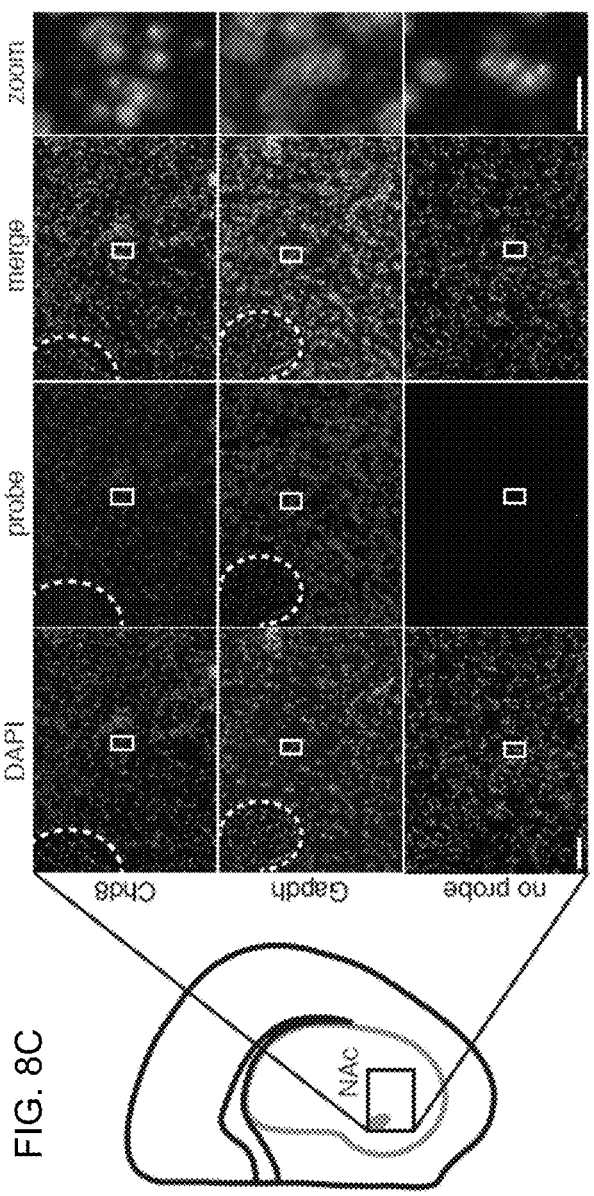

Example 9: Perturbation of Chd8 in Adult Mice Results in ASD-Like Repetitive Behavior ASD is generally viewed as a developmental disease (DiCicco-Bloom et al., 2006). However, recent reports challenge the entirely developmental hypothesis of ASD and suggest that ongoing molecular and physiological events also contribute to ASD pathology and that some ASD phenotypes can be induced or even corrected in adults (Rothwell et al., 2014; Baudouin et al., 2012; Peñagarikano et al., 2011; and Zoghbi and Bear, 2012; Guy et al., 2007). To determine the developmental expression profile of CHD8 protein in the adult mouse brain Applicants performed western blots on whole brain samples collected throughout embryonic development (E11.5-E19.5) as well as in neonates (P0) and adults (FIG. 8A). Applicants found that CHD8 protein was expressed strongly during embryonic development, but there remains a low level of expression in adults in the NAc and throughout the rest of the brain (FIG. 8B-C). These results are consistent with what has been observed in human and macaque brain (Bernier et al., 2014).

Figure 4D:
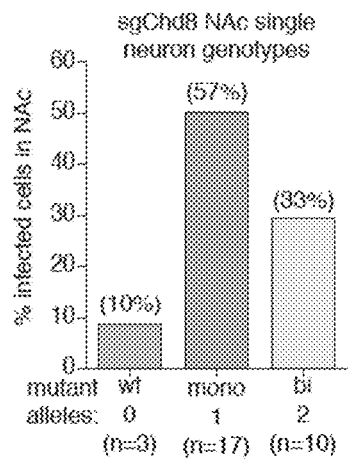
Figure 4E:
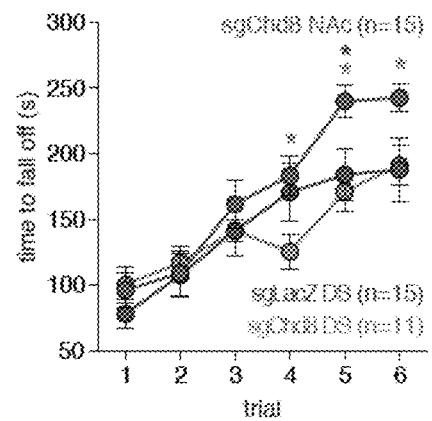
Figure 9A:
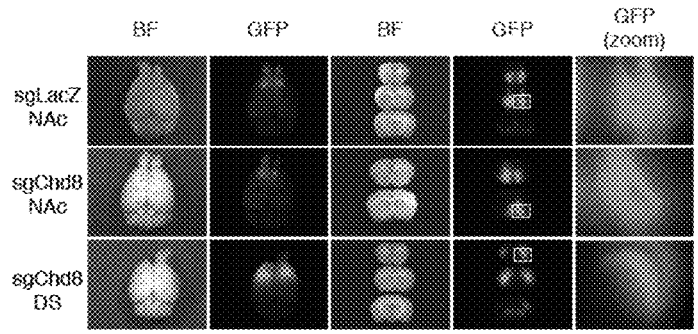
FIG. 9A-E. illustrates the perturbation of Chd8 in adult Cas9 knockin mice. 9A. Representative fluorescence images of whole brain and brain slices injected with AAV1/2 virus in the NAc or DS. The enclosed region outlines the zoomed region. 9B. In the rotarod performance test, AAV-sgChd8 NAc mice (n=15) learned at a faster rate compared to AAV-sgChd8 DS (n=11) but not AAV-sgLacZ NAc (n=15) control animals. 9C. In the rotarod performance test, AAV-sgChd8 NAc mice (n=15) had the same initial coordination compared to AAV-sgChd8 DS (n=11) and AAV-sgLacZ NAc (n=15) control animals. 9D-E. In the open field test, AAV-sgChd8 NAc (n=15), AAV-sgChd8 DS (n=11), and AAV-sgLacZ NAc (n=15) mice (D) traveled the same distance and (E) spent the same amount of time in the center. Data are means±SEM; two-tailed t-test and. *$p<0.05$.
Figure 9B:
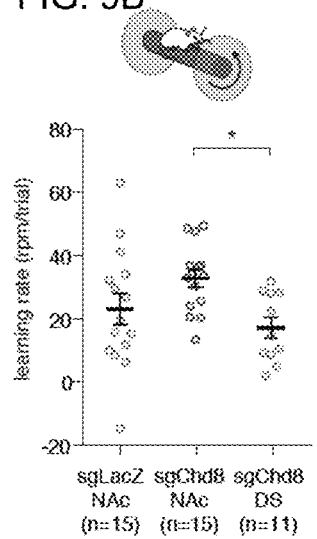
Figure 9C:
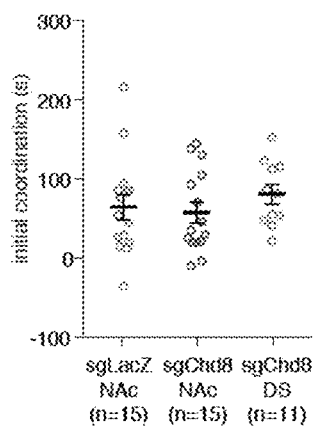
Figure 9D:
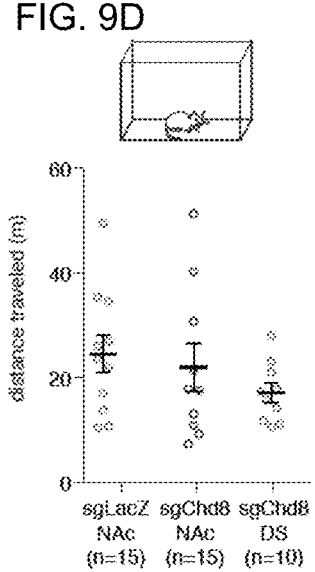
Figure 9E:
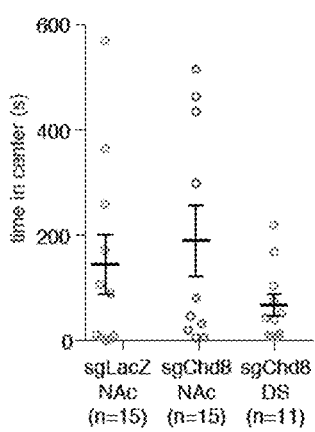

To test whether this residual CHD8 expression in the NAc of adults was required for the observed behavioral phenotypes, Applicants stereotactically injected adeno-associated virus (AAV) vectors containing Chd8-targeting sgRNA into either the NAc or the dorsal striatum of Cas9 knockin mice (Platt et al., 2014) (FIG. 4A-C, FIG. 9A). For control mice, Applicants injected an AAV carrying a non-targeting sgRNA (sgLacZ) into the NAc. Six weeks after injection Applicants dissected out the injected region and genotyped individual FACS sorted EGFP-KASH tagged fluorescent nuclei by Illumina sequencing. AAV-mediated delivery of Chd8-targeting sgRNA mediated robust mutagenesis of the Chd8 allele in the NAc. Applicants observed cells with zero (wild-type, 10%), one (monoallelic, 57%), or two (biallelic, 33%) mutant alleles (FIG. 4D). Applicants then performed the rotarod performance test on injected animals and found that perturbation of Chd8 in the NAc but not the dorsal striatum improved acquired repetitive motor learning (Figure and FIG. 9B-C). By contrast, in the open field test, perturbation of Chd8 in both the NAc and the dorsal striatum were similar to control mice (FIG. 9D-E). Taken together these results suggest that continual expression of CHD8 is required for the repetitive behavior phenotype, but not increased anxiety, highlighting a specific role for Chd8 in neurophysiology of adult mice.

Example 10: Discussion

The findings of the present invention were unexpected. CHD8 LOF mutations are strongly associated with ASD, and evidence is mounting to suggest CHD8 plays a causal role in ASD neuropathology (Bernier et al., 2014; Iossifov et al., 2014; O'Roak et al., 2012a; O'Roak et al., 2012b). Here Applicants describe ASD-like behavioral deficits in a Chd8 model system. Furthermore, Applicants identified physiological and molecular abnormalities consistent with other severe, monogenic forms of ASD. Finally, by taking advantage of the Cre-dependent Cas9 knockin mouse, Applicants demonstrated a brain region-specific role for Chd8 in neurons of the adult brain. Taken together, our findings demonstrate an important role of CHD8 in neurophysiology and establish a causal link between Chd8 mutations and ASD-like behavior in mice.

ASD presents as a range of phenotypes, and to date, more than 800 associated loci have been identified (Abrahams and Geschwind, 2008; Iossifov et al., 2012; Krumm et al., 2015; O'Roak et al., 2011; O'Roak et al., 2012a; O'Roak et al., 2012b; Parikshak et al., 2013). Many ASD risk alleles encode synaptic proteins (e.g., CNTNAP2, SHANK3, NRLGN1-4, and NRXN1), disruption of which results in synaptic and circuit dysfunction, but others have much broader functions, such as chromatin modification, DNA methylation, and transcriptional regulation (De Rubeis et al., 2014; Etherton et al., 2009; Peca et al., 2011; Penagarikano et al., 2011; Tabuchi et al., 2007). Our understanding of how these genes are related and collectively regulate normal cognitive processes is limited, but an emerging body of work suggests that loss-of-function of any of a number of these disparate proteins leads to a shared pathological mechanism (Krumm et al., 2015; O'Roak et al., 2012b; Parikshak et al., 2013). Testing this hypothesis will require careful phenotyping of relevant models to efficiently and systematically test the genotype-phenotype associations in vivo.

In this study Applicants have taken the first steps towards this goal through the generation of a heterozygous Chd8 mutant mouse reflective of mutations found in ASD patients. Applicants showed that these mice exhibit impaired social interactions, decreased preference for novelty and exploration, and acquired repetitive learning behavior. These behaviors are also found in well-established ASD mouse models (Chadman et al., 2008; Etherton et al., 2009; Kwon et al., 2006; Nakatani et al., 2009; Penagarikano et al., 2011).

Based on previous findings implicating the striatum (Di Martino et al., 2011; Hollander et al., 2005) and in particular the NAc (Dolen et al., 2013; Rothwell et al., 2014) in ASD, Applicants focused our analyses on these specific brain regions and identified an increase in spontaneous excitatory activity within MSNs of the NAc and an increase in the ionotropic glutamate receptors NR2A and NR2B specifically in the NAc. Interestingly, recent sequencing studies have identified NR2B (also known as GRIN2B) as an ASD-risk allele, and several established ASD models present with NMDA receptor dysfunction, highlighting the involvement of glutamatergic signaling within the striatum in ASD mouse models (O'Roak et al., 2011; Pan et al., 2015; Talkowski et al., 2012).

To further validate the importance of the NAc in ASD pathology and determine the function of CHD8 expression in the adult brain, Applicants utilized CRISPR-Cas9 knockin mice to perturb Chd8 directly in vivo. In these NAc-specific Chd8 perturbed mice, Applicants were able to recapitulate phenotypes observed in germline mutant animals, similar to what was recently reported for several other ASD mouse models (Michalon et al., 2012; Osterweil et al., 2013; Rothwell et al., 2014; Tian et al., 2015). These results highlight the importance of the NAc in orchestrating acquired repetitive motor learning and also highlight the role that CHD8 plays in neurophysiology. Moreover, our findings support an emerging hypothesis that puts into question the developmental nature of some ASD behaviors, thus raising the possibility for therapeutic intervention in human patients.

As discussed herein, the availability of multiple models is central to advancing our understanding of ASD and human disease in general. Although reports are beginning to detail the creation of such models via CRISPR-Cas9-based editing (Shen et al., 2013; Wang et al., 2013; Yang et al., 2013; Long et al., 2014) our understanding of the genotypic and phenotypic heterogeneity of first generation genome edited progeny and the subsequent progenies has been limited. In this study Applicants found that although the first generation of progeny gave rise to mutant mice when targeting Chd8 the number of alleles identified in a tail snip was highly variable. Furthermore, new alleles were found upon crossing the first generation progeny to wild-type animals, suggesting additional mutant germ and somatic cells. Due to the large genotypic and likely phenotypic variability that exists in the first generation progeny, Applicants refer to them as mosaic founders. To generate a non-mosaic line, Applicants crossed the mosaic founders to wild-type animals to establish a true founder strain with a single Chd8 variant. In this respect, our results highlight the heterogeneous nature of zygote editing and provide guidelines for characterizing the genotypic variation as well as a strategy to overcome this heterogeneity. Advanced methods to edit zygotes at only the single-cell stage, thus limiting the genotypic heterogeneity, will be advantageous for enabling the rapid generation of model systems for causally linking genotype to phenotype in first generation progeny.

This study provides a framework for the use of genome editing technology to interrogate neuropsychiatric disorders in both the germline and somatic cells in the brain. Together these two strategies enable rapid model generation as well as brain region-specific perturbations to test and refine hypotheses in a flexible and scalable way. Future work in this regard holds much potential for investigating the role of specific cell types in disease pathogenesis, whereby using cell type-specific Cas9 mice and viral manipulation it is possible to perturb the function of genetic elements within highly specialized cell types and understand their specific role in disease pathogenesis. Furthermore, comparative analysis of CHD8 loss-of-function and patient-specific mutations using additional model organisms, including isogenic human neurons and organoids, will further our understanding of its role in ASD. Our work here demonstrating a causal link between Chd8 mutations and ASD-like behavior in mice will help pave the way for systematic analysis of patient-derived risk loci and combinatorial manipulation of multiple genes, both of which will be necessary to untangle the complex etiology of ASD.

Experimental Procedures

In vitro validation of sgRNAs. sgRNAs were designed using the CRISPRtool (crispr.mit.edu), the sequences of which are listed in supplemental Table S1 along with genomic primers. U6-sgRNA PCR products were generated using Herculase II DNA polymerase (Agilent), purified using QIAquick PCR Purification Kit (Qiagen), and co-transfected with a Cas9 expression plasmid into mouse N2a cells (ATCC) using Lipofectamine 2000 (Life Technologies). Three days after transfection genomic DNA was extracted with QuickExtract DNA Extraction Solution (Epicenter) and used as a template for PCR amplification with Herculase II DNA polymerase (Agilent). PCR amplicons were purified, and 200 ng was used as an input into the SURVEYOR assay (Transgenomic), run on a 2% E-gel (Life Technologies), and quantified using relative band intensities. The sgRNA with the highest efficiency and least potential off target effects for each gene was chosen for mouse generation.

Preparation of Cas9 mRNA and sgRNA RNA for zygote injection. Human codon optimized Cas9 (from *Streptococcus pyogenes*) capped and polyadenylated mRNA was prepared by in vitro transcription using mMessage mMachine T7 ULTRA Transcription Kit (Ambion). sgRNA RNA was prepared by in vitro transcription using Megashortscript T7 Transcription Kit (Ambion) with an annealed partially double stranded template (Table S1). Both Cas9 mRNA and sgRNA RNA were purified by MEGAclear Transcription Clean-Up Kit (Ambion) and mixed to a final concentration of 200 ng/µl Cas9 mRNA and 50 ng/µl sgRNA RNA in $H_2O$ for injection.

Generation of germline mutant mice. Three-five week old C57BL/6N (Taconic) female mice (superovulation and plugged 0.5 dpc) were used as zygote donors and CD-1 (ICR) females were used as foster mothers. Three days prior to zygote injections, pregnant mare's serum (PMS) 5 IU was administered IP to each donor female. Forty-seven hours later hCG 5 IU was administered by IP injection and then females were paired with stud males. Donor females were sacrificed 0.5 pcd and ovaducts were collected and placed into 0.1% hyaluronidase/flushing holding media (FHM) (Millipore). Using two pairs of forceps the swollen ampulla was torn open releasing the eggs/cumulus cell bunch. The zygotes were washed in drops of FHM and the cumulus cells were removed and put into KSOM-aa culture medium (Millipore) for an hour before injection. 5 µl of Cas9/sgRNA RNA mixture was loaded into a microinjection needle (prepared by Needle puller Sutter P-97) and attached to the microinjector (Eppendorf microinjector 5242). Sets of eggs were placed into 100 µl FHM drops covered with mineral oil at room temperature. The larger pronucleus was injected until an obvious expansion occurred. Eggs were placed back into the warm and equilibrated KSOM-aa culture medium and incubated overnight. 12 hours later the two-cell stage embryos were surgically implanted bilaterally into the oviducts of 0.5 dpc CD-1 recipients. A maximum of 26 two-cell embryos were transferred into one recipient and monitored for pregnancy.

Genotyping germline mutant mice. Genomic DNA was extracted from tail snips collected from pups 10 days after birth. Genomic DNA was PCR amplified with Herculase II DNA polymerase (Agilent) to include HindIII and EcoRI restriction sites. The PCR amplicon was digested, purified, ligated into HindIII and EcoRI digested pUC19 vector, and transformed into Stb13 (Invitrogen) E. coli. Individual colonies were subjected to rolling circle amplification and Sanger sequencing using the M13R sequencing primer. Sequencing reads were mapped to the wild-type locus for mutation identification. Once the $Chd8^{+/-}$ mice (7-nucleotide deletion) were established, a qPCR-based genotyping service was used (Transnetyx).

Western blot. Protein lysates were prepared with 1× RIPA (Sigma) and 1× protease inhibitor cocktail (Roche) then quantified using the BCA Protein Assay Kit (Pierce) and equally loaded with 5 µg onto a 4%-20% Tris-HCL Criterion Gel (Bio-Rad). Proteins were transferred onto PVDF membrane (Bio-Rad), blocked with blocking solution (5% BLOT-QuickBlocker (G-Biosciences) in TBS-T (tris-buffered saline with 0.1% Tween-20)), and stained overnight at 4° C. on an orbital shaker using the following primary antibodies: anti-CHD8 (1:1000, Bethyl, A301-2214A), HRP conjugated anti-GAPDH (1:5000, Cell Signaling Technology, 3683), anti-NMDAR1 (1:1000, BD Pharmingen, 556308), anti-NR2A (1:1000, Millipore, 07-632), anti-NR2B (1:1000, Millipore, 05-920), anti-GLUR1 (1:1000, Millipore, MAB2263), anti-PTEN (1:1000, Cell Signaling Technologies, 9188), anti-beta-catenin (1:1000, Cell Signaling Technologies, 9562), and HRP conjugated anti-ACTB (1:1000, Cell Signaling Technologies, 5125). Membranes were washed three times with TBS-T and stained with secondary antibodies for 1 hr at room temperature. Applicants used HRP-conjugated secondary antibodies (1:10,000, Cell Signaling Technology, 7074 and 7076). Stained membranes were washed three times in TBS-T and then developed using SuperSignal West Femto Substrate (Pierce) and imaged on a gel imager (Bio-Rad).

Social interaction test. Experimenters and scorers were blinded to genotype throughout the study. Group housed male mice at least 6 weeks old were used for testing. Target subjects (Stranger 1 and Stranger 2) were habituated to being placed in wire cups for 5 days prior to the test. Test mice were also habituated to experimenter handling for 5 days prior to the test and on testing day the mice were habituated to the testing room for 1 hour. The test arena consisted of an acrylic box (60 cm×35 cm) with three chambers (side chambers: 20×35 cm, middle chamber: 10×35 cm) with 5 cm doors between each chamber that could be operated with a lever. The test day consisted of three scenarios: habituation, sociability and social novelty. The habituation scenario consisted of the test mouse being placed in the empty middle chamber (with both side chambers closed off) and allowed to freely explore over a 5 min session. Then, for the sociability scenario, Stranger 1 was placed in an empty wire cup in one of the side chambers and another wire cup was left empty in the other side chamber. The partitions were opened and the test mouse was allowed to freely explore the three chambers for 5 min. The test mouse remained in the chamber for another 5 minutes before the next scenario. For the social novelty scenario, Stranger 2 was added to the empty wire cup and the test mouse was allowed to freely explore for 5 min. Each scenario was recorded and manually scored for close interaction with the Stranger or the empty cup by an observer blinded to genotype.

Novel object recognition test. Experimenters and scorers were blinded to genotype throughout the study. Group housed male mice at least 6 weeks old were used for testing. Test animals were placed in an arena with a pair of identical objects and allowed to freely explore for 15 min. These two objects constitute the familiar objects. Mice were returned to their home cage for 20 min before being placed back in the arena for 5 min. In this case one of the familiar objects was replaced with a novel object. The time spent interacting with each object was manually scored by an observer blinded to genotype.

Dark-light emergence test. Experimenters and scorers were blinded to genotype throughout the study. Group housed male mice at least 6 weeks old were used for testing. The test arena consisted of a two chambers where one side is draped in black cloth (dark chamber) and the other left open (light chamber). With the opening between the two chambers closed the test mice were placed in the dark chamber. The opening between the two chambers was then opened and the mice were allowed to freely explore for 5 min. The latency to cross into the light side of the chamber and total time spent in the light side of the chamber were automatically scored by Noldus Ethovision software.

Open field test. Experimenters and scorers were blinded to genotype throughout the study. Group housed male mice at least 6 weeks old were used for testing. Test animals were placed in an empty, novel arena and allowed to freely explore for 30 minutes. The total duration moved and time spent in the middle of the arena were automatically scored by Noldus Ethovision software.

Rotarod performance test. Experimenters and scorers were blinded to genotype throughout the study. Group housed male mice at least 6 weeks old were used for testing. Animals were introduced to the apparatus (Med Associates) and the latency to fall off the rod was determined. The rotarod was set to accelerate from 4 to 40 rpm over 300 seconds. Before the first trial the animals were left on the rod for 1 min. Applicants used two sets of trial conditions on two cohorts of mice. In the first set of conditions animals were tested once a day for five days. In the second set of conditions animals were tested three times a day for two days.

Elevated plus maze. Experimenters and scorers were blinded to genotype throughout the study. Group housed male mice at least 6 weeks old were used for testing. The test arena consisted of an elevated platform with two open and two covered arms. Animals were placed in one of the covered arms and allowed to freely explore for 5 min. The amount of time in each region (open arm, closed arm, open junction) was automatically scored by Noldus Ethovision software.

Patch clamp slice electrophysiology. Slice preparation, data acquisition, and analysis were performed with experimenter blinded to mice genotype as described in previous reports (Peca et al., 2011; Rothwell et al., 2014). Briefly, 5-6 week old mice were deeply anesthetized by IP injection of avertin (1.25%, v/v) and transcardially perfused with carbogenated (95% $O_2$, 5% $CO_2$) ice-cold cutting solution that contained (in mM): 30 NaCl, 194 sucrose, 4.5 KCl, 10 glucose, 26 $NaHCO_3$, 1.2 $NaH_2PO_4$, 0.2 $CaCl_2$, and 8 $MgCl_2$. Acute parasagittal brain slices containing the core region of the NAc were sliced using a vibratome (Leica VT 1200S) in a chamber filled with ice-cold sucrose based cutting solution. 300 µm slices were cut in sucrose cutting solution and then transferred to recovery chamber at 32° C. for 12 min in ACSF. The ACSF contained (in mM): 119 NaCl, 2.3 KCl, 11 glucose, 26.2 NaHCO$_3$, 1 NaH$_2$PO$_4$, 2.5 CaCl$_2$) and 1.3 MgSO$_4$. After recovery, slices were transferred to ACSF at room temperature (25° C.) for at least 1 hr before recording. Whole-cell recordings of MSNs of the core region of the NAc were made under a DIC upright microscope (BX51WI, Olympus, Japan) using MultiClamp 700A amplifier (Molecular Device, USA). Recording electrodes with resistance of 3-4 MΩ were pulled from glass capillary (King Precision Glass, glass type 8250) using a Flaming/Brown micropipette puller (model P-97, Sutter Instrument, USA), and filled with internal solution containing (in mM): 120 CsMeSO$_4$, 15 CsCl, 10 TEA-Cl, 8 NaCl, 10 HEPES, 0.2-5 EGTA, 5 QX-314, 4 MgATP, and 0.3 NaGTP. MSNs were voltage-clamped at −70 mV. Series resistance typically ranging between 10~20 MΩ, was monitored and not compensated during the recording. Signals were sampled at frequency of 10K Hz and filtered at 2K Hz using pClamp software (Clampex 10.2, Molecular Device) via a Digidata-1440A interface (Molecular Device).

RNA-FISH. C57BL/6J male mice (Jackson Laboratories) adult (>6 weeks old) and day 17 (E17) embryonic brains were dissected and placed directly into either 10% neutral buffered formalin (NBF) or 4% paraformaldehyde (PFA)+ 0.5% acetic acid and fixed for 1, 3, or 12 hours. After fixation, brains were embedded in paraffin and sliced at 5 μm thickness and mounted on glass slides without coverslips. These slides were processed using QuantiGene ViewRNA ISH Tissue (Affymetrix). FISH probes targeting the 5th to the 12th exon of Chd8 transcripts were ordered from Affymetrix. Slides were processed according to the Quantigene ViewRNA ISH protocol. Brain slices on slides were baked at 60° C. for 30 min, then fixed at room temperature in 10% formaldehyde for 1 hour, then washed 2 times with phosphate buffered solution (PBS). To remove paraffin from the brains, slides were treated with xylenes for 5 min and dried for 5 min at room temperature. A hydrophobic barrier was drawn around the brains on each slide and dried for 20 min. Once dry, the slides were boiled in Pre-treatment Solution at 90-95° C. for 10 min then washed with PBS. Next, slides were treated with a protease solution at 40° C. for 5 min, washed with PBS then fixed in a 4% formaldehyde solution and washed once more in PBS. Chd8 or control (GAPDH) probes were diluted in vendor supplied buffer and hybridized with the sample at 40° C. for 2 hours at 85% humidity in Probe Set Diluent QT. After hybridization, slides were washed with Affymetrix Wash Solution. PreAmplifier Mix QT was added to the slide and slides were then incubated for at 40° C. for 25 min. Slides were then washed with Wash Buffer prior to incubation in Amplifier Mix QT for 15 min at 40° C. to amplify the probe signal and subsequently washed with Wash Buffer. The probe label (Label Probe 1-AP) was diluted in vendor supplied diluent and incubated on slide for 15 min at 40° C. Finally, slides were treated with Fast Red for 30 min at 40° C., fixed in 4% formaldehyde for 5 min to chromogenically label Chd8 transcripts, then washed and treated with DAPI and Gills Hematoxylin. Slides were imaged on a Zeiss Axio microscope under 20× or 40× objectives and fluorescent images were taken using a Cy3/TRITC filter for Fast Red and a DAPI filter for DAPI.

Neuron labeling and MSN dendritic spine counting. Male mice over 6 weeks of age were injected through the tail vein with 150 or 50 μl of AAV9-hSyn-EGFP-WPRE-bGH (University of Pennsylvania, Perlman School of Medicine Vector Core) titered at 8.88×10$^{13}$ GC/ml. Prior to dissection, 3 weeks after virus injection, control and Chd8$^{+/−}$ mice were assigned a code to blind the scorers to the genotype and not decoded until after data processing was complete. Mice were given a lethal dose of Ketamine/Xylazine and transcardially perfused with 4% PFA using a peristaltic pump (Gilson) 3 weeks after injection, Brains were removed and fixed overnight in 4% PFA. Tissue sectioning was performed on a vibratome (Leica VT1000S) at a thickness of 100 μm. Sections were rinsed three times in phosphate-buffered saline (PBS) with 0.1% Triton X-100 (PBS-Tx) and blocked with 5% normal goat serum (NGS) (Cell Signaling Technology) in PBS-Tx for 1 hr. Sections were incubated with anti-GIF (1:1,600, Nacalai Tesque, GF090R) primary antibodies diluted in PBS-Tx with 5% NGS overnight at 4° C. on an orbital shaker. The following day, sections were washed three times in PBS-Tx and then incubated in PBS-Tx with AlexaFluor-488 secondary antibody (1:400, Life Technologies) for 3 hours at room temperature on an orbital shaker. After the incubation, sections are rinsed with PBS-Tx three times and then mounted onto superfrost microscope slides (VWR). The sections were then coverslipped with VECTASHIELD HardSet Mounting Medium with DAPI (VECTOR Laboratories) and visualized under a confocal microscope (Zeiss LSM 710, A×10 ImagerZ2, Zen 2012 Software). MSN images were processed using a plug-in from Fiji (ImageJ, Simple Neurite Tracer) and spine density was scored manually while still blinded to genotype.

AAV1/2 production. AAV1/2 was produced as previously described (Platt et al., 2014). Briefly, low passage HEK293FT cells (Life Technologies) were transfected with the plasmid of interest, pAAV1 plasmid, pAAV2 plasmid, helper plasmid pDF6, and PEI Max (Polysciences, Inc. 24765-2) in Dulbecco's modified Eagle medium (DMEM from Life Technologies, 10569-010). At 72 hr post-transfection, the cell culture media was discarded, and the cells were rinsed and pelleted. Afterward, the viruses were applied to HiTrap heparin columns (GE Biosciences 17-0406-01) and washed with a series of salt solutions with increasing molarities. During the final stages, the eluates from the heparin columns were concentrated using molecular weight cutoff filter units (Millipore UFC910024). Titering of viral particles was performed using quantitative PCR with custom Cre-targeted Taqman probes (Life Technologies).

Stereotactic injection. Stereotactic injection was performed as previously described (Platt et al., 2014). Briefly, anesthetized male mice at least 6 weeks of age were injected with 1.25 μl of AAV virus bilaterally in the nucleus accumbens (AP +1.50, ML ±1.10, DV −4.40) or the dorsal striatum (AP +0.70, ML ±2.50, DV −2.40) at 100 nl/min. After injection the needle was left in place for 5 min before slowly being retracted.

Single nuclei preparation by FACS. Single nuclei experiments were performed as previously described (Platt et al., 2014). Briefly, 6 weeks post-injection the infected (EGFP+) regions were dissected, flash frozen on dry ice, and stored at −80° C. until use. The tissue was gently homogenized in 2 ml ice-cold homogenization buffer (HB) (320 mM Sucrose, 5 mM CaCl$_2$), 3 mM Mg(Ac)$_2$, 10 mM Tris [pH 7.8], 0.1 mM EDTA, 0.1% NP40, 0.1 mM PMSF, 1 mM β-mercaptoethanol) using a 2 ml Dounce homogenizer (Sigma Aldrich); 25 times with pestle A, followed by 25 times with pestle B. Another 3 ml of HB was added to the mixture and left on ice for 5 min. Next, gradient centrifugation was performed using 5 ml 50% OptiPrep density gradient medium (Sigma Aldrich) containing 5 mM CaCl$_2$), 3 mM Mg(Ac)$_2$, 10 mM Tris pH 7.8, 0.1 mM PMSF, 1 mM β-mercaptoethanol. The nuclei-containing mixture was gently added on the top of a 29% iso-osmolar OptiPrep solution in a centrifuge tube (Beckman Coulter, SW28 rotor). Samples were centrifuged at 10,000×g (7,500 rpm) for 30 min at 4° C. The nuclei pellet was resuspended in 65 mM β-glycerophosphate (pH 7), 2 mM $MgCl_2$, 25 mM KCl, 340 mM sucrose, and 5% glycerol. Intact nuclei were labeled with Vybrant DyeCycle Ruby Stain (Life Technologies) and sorted using a BD FACSAria III. EGFP+ nuclei were sorted into individual wells of a 96 well-plate containing 5 μl of QuickExtract DNA Extraction Solution (Epicenter). The target site was amplified by low cycle PCR to include a generic adapter that was then subjected to a second round of low cycle PCR to include sample-specific identifiers. The amplicons were pooled, gel purified using a QIAquick Gel Extraction Kit (Qiagen), quantified using Qubit (Life Technologies), and sequenced on a Miseq system (Illumina).

Animal work statement. All animal work was performed under the guidelines of Division of Comparative Medicine (DCM), with protocols (0414-024-17, 0414-027-17, and 0513-044-16) approved by Massachusetts Institute of Technology Committee for Animal Care (CAC), and were consistent with the Guide for Care and Use of Laboratory Animals, National Research Council, 1996 (institutional animal welfare assurance no. A-3125-01).

REFERENCES

Abrahams, B. S., and Geschwind, D. H. (2008). Advances in autism genetics: on the threshold of a new neurobiology. Nat Rev Genet 9, 341-355.

American Psychiatric Association. DSM-5 Task Force. (2013). Diagnostic and statistical manual of mental disorders: DSM-5, 5th edn (Washington, D.C.: American Psychiatric Association).

Baudouin, S. J., Gaudias, J., Gerharz, S., Hatstatt, L., Zhou, K., Punnakkal, P., Tanaka, K. F., Spooren, W., Hen, R., De Zeeuw, C. I., et al. (2012). Shared synaptic pathophysiology in syndromic and nonsyndromic rodent models of autism. Science 338, 128-132.

Bernier, R., Golzio, C., Xiong, B., Stessman, H. A., Coe, B. P., Penn, O., Witherspoon, K., Gerdts, J., Baker, C., Vulto-van Silfhout, A. T., et al. (2014). Disruptive CHD8 mutations define a subtype of autism early in development. Cell 158, 263-276.

Chadman, K. K., Gong, S., Scattoni, M. L., Boltuck, S. E., Gandhy, S. U., Heintz, N., and Crawley, J. N. (2008). Minimal aberrant behavioral phenotypes of neuroligin-3 R451C knockin mice. Autism Res 1, 147-158.

Cotney, J., Muhle, R. A., Sanders, S. J., Liu, L., Willsey, A. J., Niu, W., Liu, W., Klei, L., Lei, J., Yin, J., et al. (2015). The autism-associated chromatin modifier CHD8 regulates other autism risk genes during human neurodevelopment. Nat Commun 6, 6404.

De Rubeis, S., He, X., Goldberg, A. P., Poultney, C. S., Samocha, K., Cicek, A. E., Kou, Y., Liu, L., Fromer, M., Walker, S., et al. (2014). Synaptic, transcriptional and chromatin genes disrupted in autism. Nature 515, 209-215.

Di Martino, A., Kelly, C., Grzadzinski, R., Zuo, X. N., Mennes, M., Mairena, M. A., Lord, C., Castellanos, F. X., and Milham, M. P. (2011). Aberrant striatal functional connectivity in children with autism. Biol Psychiatry 69, 847-856.

Ding, J. B., Oh, W. J., Sabatini, B. L., and Gu, C. (2012). Semaphorin 3E-Plexin-D1 signaling controls pathway-specific synapse formation in the striatum. Nat Neurosci 15, 215-223.

Dolen, G., Darvishzadeh, A., Huang, K. W., and Malenka, R. C. (2013). Social reward requires coordinated activity of nucleus accumbens oxytocin and serotonin. Nature 501, 179-184.

Etherton, M. R., Blaiss, C. A., Powell, C. M., and Sudhof, T. C. (2009). Mouse neurexin-1alpha deletion causes correlated electrophysiological and behavioral changes consistent with cognitive impairments. Proc Natl Acad Sci USA 106, 17998-18003.

Geschwind, D. H. (2009). Advances in autism. Annu Rev Med 60, 367-380.

Guy, J., Gan, J., Selfridge, J., Cobb, S., and Bird, A. (2007). Reversal of neurological defects in a mouse model of Rett syndrome. Science 315, 1143-1147.

Hollander, E., Anagnostou, E., Chaplin, W., Esposito, K., Haznedar, M. M., Licalzi, E., Wasserman, S., Soorya, L., and Buchsbaum, M. (2005). Striatal volume on magnetic resonance imaging and repetitive behaviors in autism. Biol Psychiatry 58, 226-232.

Iossifov, I., O'Roak, B. J., Sanders, S. J., Ronemus, M., Krumm, N., Levy, D., Stessman, H. A., Witherspoon, K. T., Vives, L., Patterson, K. E., et al. (2014). The contribution of de novo coding mutations to autism spectrum disorder. Nature 515, 216-221.

Iossifov, I., Ronemus, M., Levy, D., Wang, Z., Hakker, I., Rosenbaum, J., Yamrom, B., Lee, Y. H., Narzisi, G., Leotta, A., et al. (2012). De novo gene disruptions in children on the autistic spectrum. Neuron 74, 285-299.

Jamain, S., Radyushkin, K., Hammerschmidt, K., Granon, S., Boretius, S., Varoqueaux, F., Ramanantsoa, N., Gallego, J., Ronnenberg, A., Winter, D., et al. (2008). Reduced social interaction and ultrasonic communication in a mouse model of monogenic heritable autism. Proc Natl Acad Sci USA 105, 1710-1715.

Kim, M. S., Chung, N. G., Kang, M. R., Yoo, N. J., and Lee, S. H. (2011). Genetic and expressional alterations of CHD genes in gastric and colorectal cancers. Histopathology 58, 660-668.

Krumm, N., Turner, T. N., Baker, C., Vives, L., Mohajeri, K., Witherspoon, K., Raja, A., Coe, B. P., Stessman, H. A., He, Z. X., et al. (2015). Excess of rare, inherited truncating mutations in autism. Nat Genet 47, 582-588.

Kwon, C. H., Luikart, B. W., Powell, C. M., Zhou, J., Matheny, S. A., Zhang, W., Li, Y., Baker, S. J., and Parada, L. F. (2006). Pten regulates neuronal arborization and social interaction in mice. Neuron 50, 377-388.

Long, C., McAnally, J. R., Shelton, J. M., Mireault, A. A., Bassel-Duby, R., and Olson, E. N. (2014). Prevention of muscular dystrophy in mice by CRISPR/Cas9-mediated editing of germline DNA. Science 345, 1184-1188.

Michalon, A., Sidorov, M., Ballard, T. M., Ozmen, L., Spooren, W., Wettstein, J. G., Jaeschke, G., Bear, M. F., and Lindemann, L. (2012). Chronic pharmacological mGlu5 inhibition corrects fragile X in adult mice. Neuron 74, 49-56.

Nakatani, J., Tamada, K., Hatanaka, F., Ise, S., Ohta, H., Inoue, K., Tomonaga, S., Watanabe, Y., Chung, Y. J., Banerjee, R., et al. (2009). Abnormal behavior in a chromosome-engineered mouse model for human 15q11-13 duplication seen in autism. Cell 137, 1235-1246.

Neale, B. M., Kou, Y., Liu, L., Ma'ayan, A., Samocha, K. E., Sabo, A., Lin, C. F., Stevens, C., Wang, L. S., Makarov, V., et al. (2012). Patterns and rates of exonic de novo mutations in autism spectrum disorders. Nature 485, 242-245.

Nestler, E. J., and Hyman, S. E. (2010). Animal models of neuropsychiatric disorders. Nat Neurosci 13, 1161-1169.

Nishiyama, M., Nakayama, K., Tsunematsu, R., Tsukiyama, T., Kikuchi, A., and Nakayama, K. I. (2004). Early embryonic death in mice lacking the beta-catenin-binding protein Duplin. Mol Cell Biol 24, 8386-8394.

Nishiyama, M., Oshikawa, K., Tsukada, Y., Nakagawa, T., Iemura, S., Natsume, T., Fan, Y., Kikuchi, A., Skoultchi, A. I., and Nakayama, K. I. (2009). CHD8 suppresses p53-mediated apoptosis through histone H1 recruitment during early embryogenesis. Nat Cell Biol 11, 172-182.

Nishiyama, M., Skoultchi, A. I., and Nakayama, K. I. (2012). Histone H1 recruitment by CHD8 is essential for suppression of the Wnt-beta-catenin signaling pathway. Mol Cell Biol 32, 501-512.

O'Roak, B. J., Deriziotis, P., Lee, C., Vives, L., Schwartz, J. J., Girirajan, S., Karakoc, E., Mackenzie, A. P., Ng, S. B., Baker, C., et al. (2011). Exome sequencing in sporadic autism spectrum disorders identifies severe de novo mutations. Nat Genet 43, 585-589.

O'Roak, B. J., Vives, L., Fu, W., Egertson, J. D., Stanaway, LB., Phelps, LG., Carvill, G., Kumar, A., Lee, C., Ankenman, K., et al. (2012a). Multiplex targeted sequencing identifies recurrently mutated genes in autism spectrum disorders. Science 338, 1619-1622.

O'Roak, B. J., Vives, L., Girirajan, S., Karakoc, E., Krumm, N., Coe, B. P., Levy, R., Ko, A., Lee, C., Smith, J. D., et al. (2012b). Sporadic autism exomes reveal a highly interconnected protein network of de novo mutations. Nature 485, 246-250.

Osterweil, E. K., Chuang, S. C., Chubykin, A. A., Sidorov, M., Bianchi, R., Wong, R. K., and Bear, M. F. (2013). Lovastatin corrects excess protein synthesis and prevents epileptogenesis in a mouse model of fragile X syndrome. Neuron 77, 243-250.

Pan, Y., Chen, J., Guo, H., Ou, J., Peng, Y., Liu, Q., Shen, Y., Shi, L., Liu, Y., Xiong, Z., et al. (2015). Association of genetic variants of GRIN2B with autism. Sci Rep 5, 8296.

Parikshak, N. N., Luo, R., Zhang, A., Won, H., Lowe, J. K., Chandran, V., Horvath, S., and Geschwind, D. H. (2013). Integrative functional genomic analyses implicate specific molecular pathways and circuits in autism. Cell 155, 1008-1021.

Peca, J., Feliciano, C., Ting, J. T., Wang, W., Wells, M. F., Venkatraman, T. N., Lascola, C. D., Fu, Z., and Feng, G. (2011). Shank3 mutant mice display autistic-like behaviours and striatal dysfunction. Nature 472, 437-442.

Penagarikano, O., Abrahams, B. S., Herman, E. I., Winden, K. D., Gdalyahu, A., Dong, H., Sonnenblick, L. I., Gruver, R., Almajano, J., Bragin, A., et al. (2011). Absence of CNTNAP2 leads to epilepsy, neuronal migration abnormalities, and core autism-related deficits. Cell 147, 235-246.

Penzes, P., Cahill, M. E., Jones, K. A., VanLeeuwen, J. E., and Woolfrey, K. M. (2011). Dendritic spine pathology in neuropsychiatric disorders. Nat Neurosci 14, 285-293.

Platt, R. J., Chen, S., Zhou, Y., Yim, M. J., Swiech, L., Kempton, H. R., Dahlman, J. E., Parnas, O., Eisenhaure, T. M., Jovanovic, M., et al. (2014). CRISPR-Cas9 knockin mice for genome editing and cancer modeling. Cell 159, 440-455.

Rosenberg, R. E., Law, J. K., Yenokyan, G., McGready, J., Kaufmann, W. E., and Law, P. A. (2009). Characteristics and concordance of autism spectrum disorders among 277 twin pairs. Arch Pediatr Adolesc Med 163, 907-914.

Rothwell, P. E., Fuccillo, M. V., Maxeiner, S., Hayton, S. J., Gokce, O., Lim, B. K., Fowler, S. C., Malenka, R. C., and Sudhof, T. C. (2014). Autism-associated neuroligin-3 mutations commonly impair striatal circuits to boost repetitive behaviors. Cell 158, 198-212.

Sanders, S. J., Murtha, M. T., Gupta, A. R., Murdoch, J. D., Raubeson, M. J., Willsey, A. J., Ercan-Sencicek, A. G., DiLullo, N. M., Parikshak, N. N., Stein, J. L., et al. (2012). De novo mutations revealed by whole-exome sequencing are strongly associated with autism. Nature 485, 237-241.

Schmeisser, M. J., Ey, E., Wegener, S., Bockmann, J., Stempel, A. V., Kuebler, A., Janssen, A. L., Udvardi, P. T., Shiban, E., Spilker, C., et al. (2012). Autistic-like behaviours and hyperactivity in mice lacking ProSAP1/Shank2. Nature 486, 256-260.

Shanks, M. O., Lund, L. M., Manni, S., Russell, M., Mauban, J. R., and Bond, M. (2012). Chromodomain helicase binding protein 8 (Chd8) is a novel A-kinase anchoring protein expressed during rat cardiac development. PLoS One 7, e46316.

Shen, B., Zhang, J., Wu, H., Wang, J., Ma, K., Li, Z., Zhang, X., Zhang, P., and Huang, X. (2013). Generation of gene-modified mice via Cas9/RNA-mediated gene targeting. Cell Res 23, 720-723.

Subtil-Rodriguez, A., Vazquez-Chavez, E., Ceballos-Chavez, M., Rodriguez-Paredes, M., Martin-Subero, J. I., Esteller, M., and Reyes, J. C. (2014). The chromatin remodeller CHD8 is required for E2F-dependent transcription activation of S-phase genes. Nucleic Acids Res 42, 2185-2196.

Tabuchi, K., Blundell, J., Etherton, M. R., Hammer, R. E., Liu, X., Powell, C. M., and Sudhof, T. C. (2007). A neuroligin-3 mutation implicated in autism increases inhibitory synaptic transmission in mice. Science 318, 71-76.

Talkowski, M. E., Rosenfeld, J. A., Blumenthal, I., Pillalamarri, V., Chiang, C., Heilbut, A., Ernst, C., Hanscom, C., Rossin, E., Lindgren, A. M., et al. (2012). Sequencing chromosomal abnormalities reveals neurodevelopmental loci that confer risk across diagnostic boundaries. Cell 149, 525-537.

Terriente-Felix, A., Molnar, C., Gomez-Skarmeta, J. L., and de Celis, J. F. (2011). A conserved function of the chromatin ATPase Kismet in the regulation of hedgehog expression. Dev Biol 350, 382-392.

Thompson, B. A., Tremblay, V., Lin, G., and Bochar, D. A. (2008). CHD8 is an ATP-dependent chromatin remodeling factor that regulates beta-catenin target genes. Mol Cell Biol 28, 3894-3904.

Tian, D., Stoppel, L. J., Heynen, A. J., Lindemann, L., Jaeschke, G., Mills, A. A., and Bear, M. F. (2015). Contribution of mGluR5 to pathophysiology in a mouse model of human chromosome 16p11.2 microdeletion. Nat Neurosci 18, 182-184.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Wilkinson, B., Grepo, N., Thompson, B. L., Kim, J., Wang, K., Evgrafov, O. V., Lu, W., Knowles, J. A., and Campbell, D. B. (2015). The autism-associated gene chromodomain helicase DNA-binding protein 8 (CHD8) regulates noncoding RNAs and autism-related genes. Transl Psychiatry 5, e568.

Won, H., Lee, H. R., Gee, H. Y., Mah, W., Kim, J. I., Lee, J., Ha, S., Chung, C., Jung, E. S., Cho, Y. S., et al. (2012). Autistic-like social behaviour in Shank2-mutant mice improved by restoring NMDA receptor function. Nature 486, 261-265.

Yang, H., Wang, H., Shivalila, C. S., Cheng, A. W., Shi, L., and Jaenisch, R. (2013). One-step generation of mice carrying reporter and conditional alleles by CRISPR/Cas-mediated genome engineering. Cell 154, 1370-1379.

Zahir, F., Firth, H. V., Baross, A., Delaney, A. D., Eydoux, P., Gibson, W. T., Langlois, S., Martin, H., Willatt, L., Marra, M. A., et al. (2007). Novel deletions of 14q11.2 associated with developmental delay, cognitive impairment and similar minor anomalies in three children. J Med Genet 44, 556-561.

The invention is further described by the following numbered paragraphs:

1. A vector containing nucleic acid molecule(s), whereby in vivo and/or ex vivo in a eukaryotic cell containing or expressing or that is able to be induced to express or that conditionally expresses Cas9: the vector expresses and provides a plurality of RNAs to guide the Cas9, and optionally delivers donor templates, and a plurality of neuronal cell-specific mutations or precise sequence substitutions in a plurality of target loci are introduced.
2. The vector of paragraph 1 wherein the cell contains Cas9 coding sequence capable of being expressed conditionally or inducibly and the vector expresses that which induces or gives rise to the condition of Cas9 expression in the cell containing Cas9.
3. The vector of paragraph 2 wherein the vector expresses Cre recombinase and Cre recombinase induces or gives rise to the condition of Cas9 expression in the cell containing Cas9.
4. The vector of any one of paragraphs 1-3 wherein the RNAs to guide Cas9 comprise CRISPR RNA and transactivating (tracr) RNA.
5. The vector of paragraph 4 wherein the RNAs to guide Cas9 comprise chimeric single guide RNA (sgRNA).
6. The vector of paragraph 5, wherein each sgRNA is driven by a single U6 promoter.
7. The vector of any one of paragraphs 1-6, wherein the vector is a viral vector.
8. The vector of paragraph 7, wherein the vector is an AAV vector.
9. The vector of any one of paragraphs 5-8, wherein each of the sgRNAs targets a different genetic locus associated with a neuronal cell/tissue-specific multigenic disease or disorder.
10. The vector of paragraph 9, wherein the multigenic disease or disorder is a psychiatric disease or disorder.
11. The vector of paragraph 9, wherein the multigenic disease is autism or an autism-spectrum disease or disorder or is obsessive compulsive disorder.
12. The vector of paragraph 9, wherein the mutagenic disease is selected from a neuronal-associated developmental disease including as epilepsy, anencephaly, encephalocele and other developmental problems.
13. The vector of any one of paragraphs 6-8, wherein each of the sgRNAs targets a different genetic locus associated with a neuronal developmental pathway or lineage.
14. The vector of any one of paragraphs 6-8, wherein the sgRNAs target one or more neuronal/nervous system genes so as to introduce a loss-of-function mutation.
15. The vector of any one of paragraphs 6-8, wherein the sgRNAs target one or more neuronal/nervous system genes so as to introduce a gain-of-function mutation.
16. The vector of any one of paragraphs 6-8, wherein the sgRNAs target one or more loci which are transcriptional control elements.
17. The vector of any one of paragraphs 1-16 wherein from 3 to 50 specific mutations or precise sequence substitutions in from 3 to 50 target loci are introduced.
18. The vector of any one of paragraphs 1-17 wherein the eukaryotic cell is a mammalian cell.
19. The vector of paragraph 18 wherein the eukaryotic cell is part of a non-human transgenic eukaryote having cells that express Cas9.
20. The vector of paragraph 19 wherein the non-human transgenic eukaryote having cells that express or that are able to be induced to express or that conditionally express Cas9 is an animal or a mammal or a primate, or a rodent, or a mouse, or a rat or a rabbit, or a canine or dog, or a cow or bovine, or a sheep or ovine or a goat or a pig, or fowl or poultry, or a chicken, or a fish, or an insect or an arthropod.
21. The vector of paragraph 18 wherein the mammalian cell is a mouse cell.
22. The vector of paragraph 21 wherein the mouse cell is part of a transgenic mouse having cells that express or that are able to be induced to express or that conditionally express Cas9.
23. A method for introducing multiple mutations ex vivo in a tissue, organ or a cell line of neuronal origin comprising Cas9-expressing eukaryotic cell(s) or cell(s) that are able to be induced to express or that conditionally express Cas9, or in vivo in a transgenic non-human mammal having cells that express or that are able to be induced to express or that conditionally express Cas9, comprising delivering to cell(s) of the tissue, organ, cell or mammal the vector of any one of paragraphs 1-22.
24. The method of paragraph 23, wherein the method comprises delivering to cells of the transgenic non-human mammal, and the transgenic non-human mammal is a transgenic mouse having cells that express or that are able to be induced to express or that conditionally express Cas9.
25. The method of paragraph 24, wherein transgenic mouse having cells that express or that are able to be induced to express or that conditionally express Cas9 comprises a mouse that has had a Cas9 transgene knocked into the Rosa26 locus.
26. The method of paragraph 25, wherein the Cas9 transgene further comprises a Lox-Stop-polyA-Lox (LSL) cassette thereby rendering Cas9 expression inducible by Cre recombinase.
27. A method for modeling a neuronal/nervous system related disease or disorder comprising introducing multiple mutations ex vivo in a tissue, organ or a cell line comprising Cas9-expressing eukaryotic cell(s) or cell(s) that are able to be induced to express or that conditionally express Cas9, or in vivo in a transgenic non-human mammal having cells that express or that are able to be induced to express or that conditionally express Cas9, comprising delivering to cell(s) of the tissue, organ, cell or mammal the vector of any one of paragraphs 1-22, wherein the specific mutations or precise sequence substitutions are or have been correlated to the neuronal/nervous system related disease or disorder.
28. A method for modeling a neuronal/nervous system related disease or disorder, comprising delivering to neuronal cells a vector containing nucleic acid molecule(s), whereby the neuronal cells contain or express or are able to be induced to express or conditionally express Cas9 and the vector expresses one or more RNAs (i) to guide the Cas9 to introduce mutations in one or more target genetic loci or (ii) to guide the Cas9 to activate or inhibit expression of a target gene in the neuronal cells, thereby modulating expression of one or more genes expressed in the neuronal cells, and wherein expression of the one or more genes is associated with the response or disease.

29. The method of paragraph 28, wherein the neuronal cells are derived from a non-human transgenic animal having cells that contain or express or are able to be induced to express or conditionally express Cas9, and the vector is delivered to the neuronal cells ex vivo.

30. The method of paragraph 27 or 28, wherein the method comprises delivering to cells of the transgenic non-human mammal the vector, and the transgenic non-human mammal is a transgenic mouse having cells that express or that are able to be induced to express or that conditionally express Cas9.

31. The method of paragraph 30, wherein transgenic mouse having cells that express or that are able to be induced to express or that conditionally express Cas9 comprises a mouse that has had a Cas9 transgene knocked into the Rosa26 locus.

32. The method of paragraph 31, wherein the Cas9 transgene further comprises a Lox-Stop-polyA-Lox (LSL) cassette thereby rendering Cas9 expression inducible by Cre recombinase.

33. The method of any one of paragraphs 27-32, wherein the disease is a psychiatric disease or disorder.

34. An individualized or personalized treatment of a neuronal/nervous system related disease or disorder in a subject in need of such treatment comprising:
  (a) introducing multiple mutations ex vivo in a tissue, organ or a cell line comprising Cas9-expressing eukaryotic cell(s) or cell(s) that are able to be induced to express or that conditionally express Cas9, or in vivo in a transgenic non-human mammal having cells that express or that are able to be induced to express or that conditionally express Cas9, comprising delivering to cell(s) of the tissue, organ, cell or mammal the vector of any one of paragraphs 1-22, wherein the specific mutations or precise sequence substitutions are or have been correlated to the neuronal/nervous system related disease or disorder;
  (b) testing treatment(s) for the neuronal/nervous system related disease or disorder on the cells to which the vector has been delivered that have the specific mutations or precise sequence substitutions correlated to the neuronal/nervous system related disease or disorder; and
  (c) treating the subject based on results from the testing of treatment(s) of step (b).

35. The method of paragraph 34 wherein the method comprises delivering to cells of the transgenic non-human mammal the vector, and the transgenic non-human mammal is a transgenic mouse having cells that express or that are able to be induced to express or that conditionally express Cas9, and the neuronal/nervous system related disease or disorder is a psychiatric disease or disorder.

36. The method of paragraph 35 wherein the psychiatric disorder is autism or an autism-spectrum disease or disorder or is obsessive compulsive disorder.

37. The method of any one of paragraphs 11, 33 or 36 wherein the sgRNA targets SHANK3, SAPAP3, MECP2, CHD8, DYRK1A, GRIN2B, KATNAL2, RIMS1, SCN2A, POGZ, ADNP, ARID1B, TBR1, NLRC5, STAC2, CRYBG3, SLC4A8, RAD54L2, MUC5B, MK167, POGZ, NEB, MYH9, TANC2, SCN2A, PIK3R3, ACO1, CAPN9, CTNNA2, GRIN2A, ASH1L, LRP1, STAG1, SYNGAP1 or any combination thereof.

38. A non-human transgenic eukaryote or mammal having cells that express or that are able to be induced to express or that conditionally express Cas9 and a neuronal/nervous system related disease or disorder.

39. A non-human transgenic eukaryote or mammal having cells that express or that are able to be induced to express or that conditionally express Cas9 and a neuronal/nervous system related disease or disorder, obtained or obtainable by or in a method of any one of paragraphs 23-37.

40. The non-human transgenic eukaryote or mammal of paragraph 38 or 39 which is an animal or a mammal or a primate, or a rodent, or a mouse, or a rat or a rabbit, or a canine or dog, or a cow or bovine, or a sheep or ovine or a goat or a pig, or fowl or poultry, or a chicken, or a fish, or an insect or an arthropod.

41. A kit comprising one or more vectors as paragraphed in any one of paragraphs 1-22 and a tissue, organ or a cell line comprising Cas9-expressing eukaryotic cell(s) or cell(s) that are able to be induced to express or that conditionally express Cas9, or in vivo in a transgenic non-human eukaryote or mammal having cells that express or that are able to be induced to express or that conditionally express Cas9; and optionally instructions for using the vector(s) and the tissue, organ or cell(s) or the eukaryote or mammal.

42. The kit of paragraph 31 wherein the kit includes the instructions.

43. The kit of paragraph 42 wherein the instructions provide for performing a method of any one of paragraphs 23-35.

44. The kit of any one of paragraphs 41-43 wherein the kit includes a non-human transgenic eukaryote or mammal having cells that express or that are able to be induced to express or that conditionally express Cas9 that is is an animal or a mammal or a primate, or a rodent, or a mouse, or a rat or a rabbit, or a canine or dog, or a cow or bovine, or a sheep or ovine or a goat or a pig, or fowl or poultry, or a chicken, or a fish, or an insect or an arthropod.

45. The kit of paragraph 44 wherein the kit includes a transgenic mouse having cells that express or that are able to be induced to express or that conditionally express Cas9.

46. A method for modulating neuronal cell activity, comprising delivering to the neuronal cell a vector containing nucleic acid molecule(s), whereby the neuronal cell contains or expresses or is able to be induced to express or conditionally expresses Cas9 and the vector expresses one or more RNAs to guide the Cas9 and optionally delivers donor template(s) to introduce one or more sequence alterations, wherein the sequence alteration(s) are selected from mutations and repair to wild type, in one or more target genetic loci in the neuronal cell, thereby modulating expression of one or more genes in the neuronal cell.

47. The method of any paragraph 46 wherein the RNAs to guide Cas9 comprise chimeric single guide RNA (sgRNA).

48. The method of paragraph 47, wherein each sgRNA is driven by a U6 promoter.

49. The method of any one of paragraphs 46-48, wherein the vector is a lentiviral vector.

50. The method of paragraph 49, wherein the vector is a U6-sgRNA lentiviral vector.

51. The method of any one of paragraphs 47-50, wherein the sgRNAs target one or more genes expressed in the neuronal cell so as to introduce loss-of-function or gain-of-function mutations.

52. The method of any one of paragraphs 46-51 wherein the neuronal cell is a mammalian neuronal cell.

53. The method of paragraph 52 wherein the neuronal cell is derived from a non-human transgenic animal having cells that contain or express or are able to be induced to express or conditionally express Cas9, and the vector is delivered to the neuronal cell ex vivo.

54. The method of paragraph 53 wherein the non-human transgenic animal having cells that contain or express or are able to be induced to express or conditionally express Cas9 is a mammal or a primate, or a rodent, or a mouse, or a rat or a rabbit, or a canine or dog, or a cow or bovine, or a sheep or ovine or a goat or a pig, or fowl or poultry, or a chicken, or a fish.

55. The method of paragraph 52 wherein the mammalian neuronal cell is a mouse neuronal cell.

56. The method of paragraph 55 wherein the mouse neuronal cell is from a transgenic mouse having cells that contain or express or are able to be induced to express or conditionally express Cas9.

57. The method of paragraph 56, wherein the transgenic mouse having cells that contain or express or are able to be induced to express or conditionally express Cas9 comprises a mouse that has had a Cas9 transgene knocked into the Rosa26 locus.

58. The method of any of paragraphs 46-52, wherein the vector is delivered to the neuronal cell in vivo.

59. The method of any one of paragraphs 46-58, wherein the vector is delivered to the neuronal cell using a cell-penetrating peptide (CPP).

60. An isolated neuronal cell comprising a vector containing a nucleic acid molecule(s), wherein the neuronal cell contains or expresses or is able to be induced to express or conditionally express Cas9 and the vector encodes one or more RNAs capable of (i) guiding the Cas9 and optionally delivering one or more donor template(s) to introduce one or more sequence alterations, wherein the sequence alteration(s) are selected from mutations and repair to wild type, in one or more target genetic loci or (ii) guiding the Cas9 to activate or inhibit expression of a target gene in the neuronal cell, and thereby modulating expression of one or more genes in the neuronal cell.

61. An isolated neuronal cell comprising a vector containing a nucleic acid molecule(s), wherein the neuronal cell contains or expresses or is able to be induced to express or conditionally express Cas9, (i) one or more target genetic loci in the neuronal cell comprise mutations derived from Cas9 activity guided by one or more RNAs encoded by the vector or (ii) expression of one or more target genes in the neuronal cells is activated or inhibited by Cas9 guided by one or more RNAs encoded by the vector, and wherein expression of one or more genes in the neuronal cell is modulated thereby.

62. The isolated neuronal cell of paragraph 60 or paragraph 61, wherein the RNAs to guide Cas9 comprise chimeric single guide RNA (sgRNA).

63. The isolated neuronal cell of paragraph 62, wherein each sgRNA is driven by a U6 promoter.

64. The isolated neuronal cell of any one of paragraphs 60 to 63, wherein the vector is a lentiviral vector.

65. The isolated neuronal cell of paragraph 64, wherein the vector is a U6-sgRNA lentiviral vector.

66. The isolated neuronal cell of any one of paragraphs 62-65, wherein the sgRNAs target one or more genes expressed in the neuronal cell so as to introduce loss-of-function or gain-of-function mutations.

67. The isolated neuronal cell of any one of paragraphs 60-66 wherein the neuronal cell is a mammalian neuronal cell.

68. The isolated neuronal cell of paragraph 67, wherein the neuronal cell is derived from a non-human transgenic animal having cells that contain or express or are able to be induced to express or conditionally express Cas9.

69. The isolated neuronal cell of paragraph 68, wherein the non-human transgenic animal having cells that contain or express or are able to be induced to express or conditionally express Cas9 is a mammal or a primate, or a rodent, or a mouse, or a rat or a rabbit, or a canine or dog, or a cow or bovine, or a sheep or ovine or a goat or a pig, or fowl or poultry, or a chicken, or a fish.

70. The isolated neuronal cell of paragraph 67, wherein the mammalian neuronal cell is a mouse neuronal cell.

71. The isolated neuronal cell of paragraph 70, wherein the mouse neuronal cell is from a transgenic mouse having cells that contain or express or are able to be induced to express or conditionally express Cas9.

72. The isolated neuronal cell of paragraph 71, wherein the transgenic mouse having cells that contain or express or are able to be induced to express or conditionally express Cas9 comprises a mouse that has had a Cas9 transgene knocked into the Rosa26 locus.

73. The isolated neuronal cell of any one of paragraphs 60-72, wherein the one or more genes is associated with a neuronal/nervous system related disease or disorder.

74. A non-human transgenic eukaryote or mammal having neuronal cells that express or that are able to be induced to express or that conditionally express Cas9, and one or more mutation(s) in one or more gene(s) associated with a neuronal/nervous system related disease or disorder.

75. A method of drug screening for therapeutic molecules or agents that alleviate symptoms of ASD comprising treating a transgenic animal that is a loss-of-function heterozygote for at least the CHD8 gene with at least one molecule or agent and determining changes in phenotype, wherein drug candidates are selected that alleviate symptoms.

76. A method of selecting candidate drug target genes comprising mutating at least one additional gene in a transgenic animal that is a loss-of-function heterozygote for the CHD8 gene and determining the phenotype, wherein the additional mutated gene is a drug target if the ASD phenotype is enhanced or decreased.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for modeling a neuronal/nervous system related disease or disorder, comprising:
   delivering a vector encoding a plurality of guides to a genetically-modified eukaryotic cell or a genetically-modified non-human animal,
   wherein the genetically-modified eukaryotic cell or genetically-modified non-human animal comprises a chromosomally integrated Cas9 gene that is constitutively expressed, or a chromosomally integrated Cas9 gene capable of being inducibly or conditionally expressed to produce a Cas9 protein,
   wherein, when the Cas9 gene and the plurality of guides are expressed in the cell or animal, the plurality of guides are capable of guiding the Cas9 protein to a plurality of neuronal cell-specific target loci, thereby introducing multiple neuronal cell-specific mutations or substitutions at the neuronal cell-specific target loci.

2. The method of claim 1, wherein the neuronal cell-specific mutations or substitutions are or have been correlated to the neuronal/nervous system related disease or disorder.

3. The method of claim 1, wherein each of the guides targets a different genetic locus associated with a neuronal cell/tissue-specific multigenic disease or disorder.

4. The method of claim 3, wherein the multigenic disorder is a psychiatric disease or disorder.

5. The method of claim 3, wherein the multigenic disorder is autism, an autism-spectrum disease or disorder, or obsessive compulsive disorder.

6. The method of claim 3, wherein the multigenic disorder is a neuronal-associated developmental disease, epilepsy, anencephaly, or ancephalocele.

7. The method of claim 1, wherein the guides target one or more neuronal/nervous system genes so as to introduce a loss-of-function mutation or a gain-of-function mutation.

8. The method of claim 1, wherein the guides target one or more loci which are transcriptional control elements.

9. The method of claim 1, wherein each of the guides targets a different genetic locus associated with a neuronal developmental pathway or lineage.

10. The method of claim 1, wherein from 3 to 50 neuronal cell-specific mutations or substitutions in from 3 to 50 target loci are introduced.

11. The method of claim 1, wherein the genetically-modified non-human animal is a non-human primate, a rodent, a canine, a bovine, an ovine, a mouse, a dog, a goat, a pig, a rabbit, a fowl or poultry.

12. The method of claim 1, wherein the genetically modified non-human animal comprises neuronal cells that comprise a Cas9 gene that is constitutively, or capable of being inducibly, or conditionally expressed.

13. The method of claim 1, wherein the plurality of guides comprises guides that target one or more of SHANK3, SAPAP3, MECP2, CHD8, DYRK1A, GRIN2B, KATNAL2, RIMS1, SCN2A, POGZ, ADNP, ARID1B, TBR1, NLRC5, STAC2, CRYBG3, SLC4A8, RAD54L2, MUC5B, MK167, NEB, MYH9, TANC2, PIK3R3, ACO1, CAPN9, CTNNA2, GRIN2A, ASH1L, LRP1, STAG1, and SYNGAP1.

14. The method of claim 1, further comprising screening for therapeutic molecules or agents that alleviate a symptom of the neuronal/nervous system related disease or disorder, wherein screening for the therapeutic molecules or agents comprises:
   treating the cell or the transgenic non-human animal with one of the therapeutic molecules or agents;
   determining a change in the symptom; and
   selecting a drug candidate based on the change in the symptom.

15. The method of claim 14, wherein the cell or the genetically modified non-human animal exhibits a loss-of-function or gain-of-function for at least one genetic locus associated with the neuronal/nervous system related disease or disorder.

16. The method of claim 15, wherein the neuronal/nervous system related disease or disorder is autism spectrum disorder (ASD) and the at least one genetic locus is CHD8.

17. The method of claim 14, comprising treating the genetically modified non-human animal with one of the therapeutic molecules or agents, wherein the transgenic non-human animal is a loss-of-function or gain-of-function heterozygote or homozygote.

18. The method of claim 1, further comprising delivering donor templates and a plurality of neuronal cell-specific mutations or substitutions.

19. The method of claim 1, wherein the Cas9 gene is present in the cell or animal prior to the vector is delivered.

* * * * *

UNITED STATES PATENT AND TRADEMARK OFFICE
CERTIFICATE OF CORRECTION

| | | |
|---|---|---|
| PATENT NO. | : 11,459,557 B2 | Page 1 of 1 |
| APPLICATION NO. | : 15/467949 | |
| DATED | : October 4, 2022 | |
| INVENTOR(S) | : Randall Jeffrey Platt et al. | |

It is certified that error appears in the above-identified patent and that said Letters Patent is hereby corrected as shown below:

In the Specification

In Column 18, Line 6, delete "nar." and insert -- http://nar. --.

In Column 18, Line 7, delete "html)" and insert -- html). --.

In Column 66, Line 7, delete "EMXI" and insert -- EMX1 --.

In Column 77, Line 15, delete "$CaCl_2$)" and insert -- $CaCl_2$ --.

In Column 77, Line 22, delete "$CaCl_2$)" and insert -- $CaCl_2$ --.

In Column 83, Line 1, delete "Mass." and insert -- M A --.

In Column 84, Line 54, delete "PARK5," and insert -- PARK8, --.

In Column 113, Line 4, delete "$CaCl_2$)" and insert -- $CaCl_2$ --.

In Column 114, Line 13, delete "GIF" and insert -- GFP --.

In Column 114, Line 59, delete "$CaCl_2$)," and insert -- $CaCl_2$, --.

In Column 114, Line 66, delete "$CaCl_2$)," and insert -- $CaCl_2$, --.

Signed and Sealed this
Eleventh Day of April, 2023

Katherine Kelly Vidal
*Director of the United States Patent and Trademark Office*

SEQUENCE LISTING

<160> NUMBER OF SEQ ID NOS: 51

<210> SEQ ID NO 1
<211> LENGTH: 137
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 1
nnnnnnnnnn nnnnnnnnnn gttttgtac tctcaagatt tagaaataaa tcttgcagaa      60
gctacaaaga taaggcttca tgccgaaatc aacaccctgt cattttatgg cagggtgttt     120
tcgttattta atttttt                                                   137

<210> SEQ ID NO 2
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 2
nnnnnnnnnn nnnnnnnnnn gttttgtac tctcagaaat gcagaagcta caaagataag      60
gcttcatgcc gaaatcaaca ccctgtcatt ttatggcagg gtgttttcgt tatttaattt    120
ttt                                                                  123

<210> SEQ ID NO 3
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 3
nnnnnnnnnn nnnnnnnnnn gttttgtac tctcagaaat gcagaagcta caaagataag      60
gcttcatgcc gaaatcaaca ccctgtcatt ttatggcagg gtgttttttt                110

<210> SEQ ID NO 4
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 4
nnnnnnnnnn nnnnnnnnnn gttttagagc tagaaatagc aagttaaaat aaggctagtc      60
cgttatcaac ttgaaaaagt ggcaccgagt cggtgctttt tt                        102
```

<210> SEQ ID NO 5
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 5
nnnnnnnnnn nnnnnnnnnn gttttagagc tagaaatagc aagttaaaat aaggctagtc    60
cgttatcaac ttgaaaaagt gttttttt                                       88

<210> SEQ ID NO 6
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 6
nnnnnnnnnn nnnnnnnnnn gttttagagc tagaaatagc aagttaaaat aaggctagtc    60
cgttatcatt tttttt                                                    76

<210> SEQ ID NO 7
<211> LENGTH: 20
<212> TYPE: DNA
<213> ORGANISM: Homo sapiens

<400> SEQUENCE: 7
gagtccgagc agaagaagaa                                                20

<210> SEQ ID NO 8
<211> LENGTH: 20
<212> TYPE: DNA
<213> ORGANISM: Homo sapiens

<400> SEQUENCE: 8
gagtcctagc aggagaagaa                                                20

<210> SEQ ID NO 9
<211> LENGTH: 20
<212> TYPE: DNA
<213> ORGANISM: Homo sapiens

<400> SEQUENCE: 9
gagtctaagc agaagaagaa                                                20

<210> SEQ ID NO 10
<211> LENGTH: 7
<212> TYPE: PRT
<213> ORGANISM: Simian virus 40

<400> SEQUENCE: 10

```
Pro Lys Lys Lys Arg Lys Val
1               5
```

<210> SEQ ID NO 11
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 11

```
Lys Arg Pro Ala Ala Thr Lys Lys Ala Gly Gln Ala Lys Lys Lys Lys
1               5                   10                  15
```

<210> SEQ ID NO 12
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 12

```
Pro Ala Ala Lys Arg Val Lys Leu Asp
1               5
```

<210> SEQ ID NO 13
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 13

```
Arg Gln Arg Arg Asn Glu Leu Lys Arg Ser Pro
1               5                   10
```

<210> SEQ ID NO 14
<211> LENGTH: 38
<212> TYPE: PRT
<213> ORGANISM: Homo sapiens

<400> SEQUENCE: 14

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35
```

<210> SEQ ID NO 15
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 15

```
Arg Met Arg Ile Glx Phe Lys Asn Lys Gly Lys Asp Thr Ala Glu Leu
1               5                   10                  15
```

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 16
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 16

Val Ser Arg Lys Arg Pro Arg Pro
1               5

<210> SEQ ID NO 17
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 17

Pro Pro Lys Lys Ala Arg Glu Asp
1               5

<210> SEQ ID NO 18
<211> LENGTH: 8
<212> TYPE: PRT
<213> ORGANISM: Homo sapiens

<400> SEQUENCE: 18

Pro Gln Pro Lys Lys Lys Pro Leu
1               5

<210> SEQ ID NO 19
<211> LENGTH: 12
<212> TYPE: PRT
<213> ORGANISM: Mus musculus

<400> SEQUENCE: 19

Ser Ala Leu Ile Lys Lys Lys Lys Met Ala Pro
1               5                   10

<210> SEQ ID NO 20
<211> LENGTH: 5
<212> TYPE: PRT
<213> ORGANISM: Influenza virus

<400> SEQUENCE: 20

Asp Arg Leu Arg Arg
1               5

<210> SEQ ID NO 21
<211> LENGTH: 7
<212> TYPE: PRT
<213> ORGANISM: Influenza virus

<400> SEQUENCE: 21

Pro Lys Gln Lys Lys Arg Lys

```
1               5

<210> SEQ ID NO 22
<211> LENGTH: 10
<212> TYPE: PRT
<213> ORGANISM: Hepatitis delta virus

<400> SEQUENCE: 22

Arg Lys Leu Lys Lys Lys Ile Lys Lys Leu
1               5                   10

<210> SEQ ID NO 23
<211> LENGTH: 10
<212> TYPE: PRT
<213> ORGANISM: Mus musculus

<400> SEQUENCE: 23

Arg Glu Lys Lys Lys Phe Leu Lys Arg Arg
1               5                   10

<210> SEQ ID NO 24
<211> LENGTH: 20
<212> TYPE: PRT
<213> ORGANISM: Homo sapiens

<400> SEQUENCE: 24

Lys Arg Lys Gly Asp Glu Val Asp Gly Val Asp Glu Val Ala Lys Lys
1               5                   10                  15

Lys Ser Lys Lys
            20

<210> SEQ ID NO 25
<211> LENGTH: 17
<212> TYPE: PRT
<213> ORGANISM: Homo sapiens

<400> SEQUENCE: 25

Arg Lys Cys Leu Gln Ala Gly Met Asn Leu Glu Ala Arg Lys Thr Lys
1               5                   10                  15

Lys

<210> SEQ ID NO 26
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
guuuuagagc ua                                                          12

<210> SEQ ID NO 27
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
gcagcctctg ttccacatac ac                                               22
```

<210> SEQ ID NO 28
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
accattctca gtggctcaac aa                                              22

<210> SEQ ID NO 29
<211> LENGTH: 26
<212> TYPE: DNA
<213> ORGANISM: Mus musculus

<400> SEQUENCE: 29
acaatggata cacctggtcg aaaggg                                          26

<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
caaauggaua caccggucg a                                                21

<210> SEQ ID NO 31
<211> LENGTH: 49
<212> TYPE: DNA
<213> ORGANISM: Mus musculus

<400> SEQUENCE: 31
aaacagctat gacaatggat acacctggtc gaaggggtgt accagtcag                 49

<210> SEQ ID NO 32
<211> LENGTH: 42
<212> TYPE: DNA
<213> ORGANISM: Mus musculus

<400> SEQUENCE: 32
aaacagctat gacaatggat acacctgggg tgtaccagtc ag                        42

<210> SEQ ID NO 33
<211> LENGTH: 40
<212> TYPE: DNA
<213> ORGANISM: Mus musculus

<400> SEQUENCE: 33
aaacagctat gacaatggat acaatgggtg taccagtcag                           40

<210> SEQ ID NO 34
<211> LENGTH: 40
<212> TYPE: DNA
<213> ORGANISM: Mus musculus

<400> SEQUENCE: 34
aaacagctat gacaatggat acacctggtg taccagtcag                           40

```
<210> SEQ ID NO 35
<211> LENGTH: 38
<212> TYPE: DNA
<213> ORGANISM: Mus musculus

<400> SEQUENCE: 35
aaacagctat gacaatggac aatgggtgta ccagtcag                             38

<210> SEQ ID NO 36
<211> LENGTH: 46
<212> TYPE: DNA
<213> ORGANISM: Mus musculus

<400> SEQUENCE: 36
aaacagctat gacaatggat acacctggtg ggggtgtacc agtcag                    46

<210> SEQ ID NO 37
<211> LENGTH: 42
<212> TYPE: DNA
<213> ORGANISM: Mus musculus

<400> SEQUENCE: 37
aaacagctat gacaatggat acacctgggg tgtaccagtc ag                        42

<210> SEQ ID NO 38
<211> LENGTH: 49
<212> TYPE: DNA
<213> ORGANISM: Mus musculus

<400> SEQUENCE: 38
aaacagctat gacaatggat acagtggtac aaagggtgt accagtcag                  49

<210> SEQ ID NO 39
<211> LENGTH: 40
<212> TYPE: DNA
<213> ORGANISM: Mus musculus

<400> SEQUENCE: 39
aaacagctat gacaatggat acacctggtg taccagtcag                           40

<210> SEQ ID NO 40
<211> LENGTH: 39
<212> TYPE: DNA
<213> ORGANISM: Mus musculus

<400> SEQUENCE: 40
aaacagctat gacaatggat acacctggtc accagtcag                            39

<210> SEQ ID NO 41
<211> LENGTH: 40
<212> TYPE: DNA
<213> ORGANISM: Mus musculus

<400> SEQUENCE: 41
aaacagctat gacaatggat acacctggtg taccagtcag                           40

<210> SEQ ID NO 42
<211> LENGTH: 49
<212> TYPE: DNA
<213> ORGANISM: Mus musculus

<400> SEQUENCE: 42
aaacagctat gacaatggat acacctggtc gaagggttgt accagtcag                 49
```

<210> SEQ ID NO 43
<211> LENGTH: 50
<212> TYPE: DNA
<213> ORGANISM: Mus musculus

<400> SEQUENCE: 43
aaacagctat gacaatggat acacctggtc cgaaggggtg taccagtcag          50

<210> SEQ ID NO 44
<211> LENGTH: 40
<212> TYPE: DNA
<213> ORGANISM: Mus musculus

<400> SEQUENCE: 44
aaacagctat gacaatggat acacctggtg taccagtcag                     40

<210> SEQ ID NO 45
<211> LENGTH: 42
<212> TYPE: DNA
<213> ORGANISM: Mus musculus

<400> SEQUENCE: 45
aaacagctat gacaatggat acacctgggg tgtaccagtc ag                  42

<210> SEQ ID NO 46
<211> LENGTH: 40
<212> TYPE: DNA
<213> ORGANISM: Mus musculus

<400> SEQUENCE: 46
aaacagctat gacaatggat acacctggtg taccagtcag                     40

<210> SEQ ID NO 47
<211> LENGTH: 53
<212> TYPE: DNA
<213> ORGANISM: Mus musculus

<400> SEQUENCE: 47
aaacagctat gacaatggat acacctgggt gtacgaaggg gtgtaccagt cag      53

<210> SEQ ID NO 48
<211> LENGTH: 40
<212> TYPE: DNA
<213> ORGANISM: Mus musculus

<400> SEQUENCE: 48
aaacagctat gacaatggat acacctggtg taccagtcag                     40

<210> SEQ ID NO 49
<211> LENGTH: 50
<212> TYPE: DNA
<213> ORGANISM: Mus musculus

<400> SEQUENCE: 49
aaacagctat gacaatggat acacctggtg cgaaggggtg taccagtcag          50

<210> SEQ ID NO 50
<211> LENGTH: 50
<212> TYPE: DNA
<213> ORGANISM: Mus musculus

<400> SEQUENCE: 50
aaacagctat gacaatggat acacctggtc cgaaggggtg taccagtcag          50

```
<210> SEQ ID NO 51
<211> LENGTH: 40
<212> TYPE: DNA
<213> ORGANISM: Mus musculus

<400> SEQUENCE: 51
aaacagctat gacaatggat acacctggtg taccagtcag                          40
```